(12) United States Patent
Bond et al.

(10) Patent No.: US 10,941,143 B2
(45) Date of Patent: Mar. 9, 2021

(54) IMIDAZO [1,5-A]PYRIDINE COMPOUNDS AND THEIR USE

(71) Applicant: Alterity Therapeutics Limited, Melbourne (AU)

(72) Inventors: Silas Bond, Melbourne (AU); Penelope Jane Huggins, Melbourne (AU); Jack Gordon Parsons, Melbourne (AU)

(73) Assignee: ALTERITY THERAPEUTICS LIMITED, Melbourne (AU)

( * ) Notice: Subject to any disclaimer, the term of this patent is extended or adjusted under 35 U.S.C. 154(b) by 0 days.

(21) Appl. No.: 16/818,641

(22) Filed: Mar. 13, 2020

(65) Prior Publication Data

US 2020/0291021 A1    Sep. 17, 2020

(30) Foreign Application Priority Data

Mar. 15, 2019    (AU) ................. 2019900867

(51) Int. Cl.
| | | |
|---|---|---|
| *C07D 471/04* | (2006.01) | |
| *C07D 487/04* | (2006.01) | |
| *A61P 25/24* | (2006.01) | |
| *A61P 25/28* | (2006.01) | |
| *A61P 25/16* | (2006.01) | |

(52) U.S. Cl.
CPC ......... *C07D 471/04* (2013.01); *C07D 487/04* (2013.01); *A61P 25/16* (2018.01); *A61P 25/24* (2018.01); *A61P 25/28* (2018.01)

(58) Field of Classification Search
CPC ................................................. C07D 471/04
See application file for complete search history.

(56) References Cited

FOREIGN PATENT DOCUMENTS

| | | |
|---|---|---|
| WO | 2005037836 | 4/2005 |
| WO | 2009143051 | 11/2009 |

OTHER PUBLICATIONS

Australian Search Report for Application No. 2019900867 dated Aug. 19, 2019 (22 pages).
Hu, Z. et al., 'Synthesis of imidazo[1,5-a]pyridines via I2-mediated sp3 C-H amination', Organic and Biomolecular Chemistry, 2018, vol. 16, pp. 5653-5660.
Khan, M. S. et al., 'Design, Synthesis, Evaluation and Thermodynamics of 1-Substituted Pyridylimidazo[1,5-a]Pyridine Derivatives as Cysteine Protease Inhibitors', PLOS One (2013), vol. 8, issue 8, e69982.
Muniyan, S. et al., 'Antiproliferative activity of novel imidazopyridine derivatives on castration-resistant human prostate cancer cells', Cancer Letters (2014), vol. 353, No. 1, pp. 59-67.
International Search Report and Written Opinion for Application No. PCT/AU2020/050235 dated May 7, 2020 (10 pages).

*Primary Examiner* — Susanna Moore
(74) *Attorney, Agent, or Firm* — Michael Best & Friedrich LLP

(57)    ABSTRACT

The present invention provides compounds that modulate biological metals and to pharmaceutical compositions containing such compounds. The invention particularly relates to imidazo[1,5-a]pyridine compounds of formula (I) that modulate iron and are useful for the treatment of diseases, particularly neurological diseases such as Parkinson's disease (PD), Alzheimer's disease (AD), Alzheimer-type dementia, Huntington's disease (HD), amyotrophic lateral sclerosis (ALS), frontotemporal dementia (FTD) and multiple system atrophy (MSA). The compounds of formula (I) being where variables are defined herein.

22 Claims, No Drawings

IMIDAZO [1,5-A]PYRIDINE COMPOUNDS AND THEIR USE

FIELD OF THE INVENTION

The present invention provides compounds that modulate biological metals and to pharmaceutical compositions containing such compounds. The invention particularly relates to compounds that modulate iron and to compounds for the treatment of diseases, particularly neurological diseases such as Parkinson's disease (PD), Alzheimer's disease (AD), Alzheimer-type dementia, Huntington's disease (HD), amyotrophic lateral sclerosis (ALS), frontotemporal dementia (FTD) and multiple system atrophy (MSA).

BACKGROUND OF THE INVENTION

Biological metals, including iron, are essential for living cell metabolism but must be held under extremely tight control in all physiological conditions. In certain disease conditions, metal ion management can be disrupted, resulting in elevated levels of metal that accumulate in tissues or organs. Excessive iron for example shows a wide range of toxic effects on tissues, depending on the metal's redox activity.

Oxidative stress has been described as very relevant to the physical damage observed in many neurodegenerative disorders, such as Parkinson's disease (PD) and Alzheimer's disease (AD). In the presence of molecular oxygen, iron can redox cycle between the two most stable oxidation states iron(II) and iron(III), generating oxygen-derived free radicals—such as hydroxyl radicals (.OR). These radicals are highly reactive species which are able to interact with multiple biological molecules, leading to tissue damage.

Cells adopt a number of protective strategies to prevent the formation or production of such highly reactive species, however a state of disease can overwhelm these processes. The brain, like all other tissues, protects itself against the deleterious effects of oxygen free radicals by protective enzymes such as glutathione peroxidase (GP), catalase and superoxide dismutase (SD). Protection is also afforded by relatively high amounts of glutathione and ascorbate.

Parkinson's disease is a progressive neurodegeneration of the dopaminergic neurons in the substantia nigra (SN) of patients' brains. PD patients are identified to have higher levels of iron in the SN of their brain, where the important neurotransmitter dopamine (DA) has a critical physiological function. Postmortem studies on brains from parkinsonian patients suggest the involvement of oxygen free radical-induced oxidative stress which results in lipid peroxidation of cell membranes, followed by increased membrane fluidity and finally cell death. Normally DA is metabolized in ways that lead to an excess of toxic oxygen species, such as .OH, which in the presence of a transient metal, such as iron, will produce cytotoxic oxygen free radicals, e.g. Superoxide and hydroxyl free radicals (.OR).

In PD, the above described brain defensive mechanisms against the formation of cytotoxic oxygen free radicals are defective. In the SN of parkinsonian brains there are reductions in activities of SD and GP and reduced tissue contents of glutathione and ascorbate. Moreover, iron concentrations are significantly elevated in parkinsonian SN within the dopamine neurons. The treatment of mice with the metal modulator Clioquinol has been shown to protect mice from the effects of 1-methyl-4-phenyl-1,2,3,6-tetrahydropyridine (MPTP) which causes Parkinson's symptoms. In further experiments, it has been shown that mice which are genetically engineered to express the natural iron-binding protein ferritin in the mouse SN have less available iron in their brains and are also protected from the effects of MPTP. Significantly, the mice tolerated the resulting reduction of available iron in their brains without serious side effects no matter how the iron levels were reduced.

Evidence suggests that whilst iron itself can induce oxidative processes, so too can proteins with iron binding sites. In AD, the plaque-forming Aβ peptide will redox cycle iron(III) and produce hydrogen peroxide ($H_2O_2$) by double electron transfer to $O_2$. $H_2O_2$ is a pro-oxidant molecule that reacts with reduced metal ions, such as iron(II) to generate the highly reactive hydroxyl radical (OH) via the Fenton reaction. This process in turn induces numerous adducts and protein modifications.

Critical to Alzheimer's Disease are extensive changes to all classes of macromolecules, along with apoptotic mechanisms of cell damage/death, which is partly mediated by $H_2O_2$. Principally, Aβ peptide Fenton redox activity is reliant on the iron metal binding site of Aβ peptide. The existence of this site suggests that compounds with the ability to modulate metals, including the concentration of intracellular metals or block metal binding sites will be a direct treatment for AD.

In turn, these conditions cause release of cytotoxic free radicals, resulting in neuronal death.

It would be highly desirable to find iron modulators that exhibit the remaining qualities necessary for the treatment of metal-associated disorders.

SUMMARY OF THE INVENTION

The present invention is predicated at least in part on the discovery that certain compounds are capable of modulating iron, thus making them suitable candidates for treatment of Parkinson's disease and other metal associated disorders.

In a first aspect, the present invention provides a compound of formula (I):

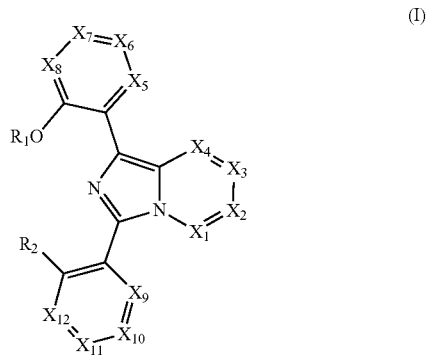

wherein
each of $X_1$ to $X_{12}$ are independently N and $CR_3$, wherein 0, 1, 2 or 3 of $X_1$ to $X_{12}$ are N;
$R_1$ is selected from the group consisting of hydrogen, alkyl, alkenyl, alkynyl, $C(O)R_4$ and $C(S)R_4$;
$R_2$ is selected from the group consisting of hydrogen, halo, $OR_5$, $SR_5$, $C(O)R_4$, $C(S)R_4$, $NO_2$, CN, $N(R_6)_2$, $S(O)_n N(R_6)_2$ and $S(O)_n R_4$;
each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mOC(S)R_4$, $(C(R_7)_2)_mSC(O)R_4$, $(C(R_7)_2)_mSC(S)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$;

$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;

$R_5$ is selected from the group consisting of hydrogen, alkyl, alkenyl, alkynyl, haloalkyl, cycloalkyl, cycloalkenyl, aryl, heterocyclyl, heteroaryl C(O)alkyl, C(O)alkenyl, C(O)alkynyl, $S(O)_nR_4$ and $S(O)_nN(R_6)_2$;

$R_6$ is selected from the group consisting of hydrogen, alkyl, alkenyl, alkynyl, haloalkyl, cycloalkyl, cycloalkenyl, aryl, heterocyclyl and heteroaryl;

each $R_7$ is independently selected from the group consisting of hydrogen, alkyl, alkenyl, alkynyl and haloalkyl;

m is 0 or an integer from 1 to 6;

n is 1 or 2;

wherein each alkyl, alkenyl, alkynyl, cycloalkyl, cycloalkenyl, aryl, heterocyclyl and heteroaryl is optionally substituted;

or a pharmaceutically acceptable salt or solvate thereof; with the proviso that when $R_1$ is methyl, $X_1$, $X_2$, $X_3$, $X_4$, $X_5$, $X_6$, $X_8$, $X_9$, $X_{10}$, $X_{11}$ and $X_{12}$ are each $CR_3$ where $R_3$ is hydrogen and $X_7$ is $CR_3$ where $R_3$ is $OCH_3$, $R_2$ is not hydrogen.

In another aspect of the invention there is provided a pharmaceutical composition comprising a compound of formula (I) or a pharmaceutically acceptable salt or solvate thereof and a pharmaceutically acceptable carrier and/or excipient.

In yet another aspect of the invention there is provided a method of treating or preventing a metal ion associated disorder comprising administering to a subject a compound of formula (I) or a pharmaceutically acceptable salt or solvate thereof. In some embodiments, the metal ion associated disorder is an iron ion associated disorder.

In yet another aspect of the invention there is provided a method of treating or preventing a metal ion associated neurological disorder comprising administering to a subject a compound of formula (I) or a pharmaceutically acceptable salt or solvate thereof.

In a further aspect of the invention, there is provided a compound of formula (I) or a pharmaceutically acceptable salt or solvate thereof for use in treating or preventing a metal ion associated disorder. In some embodiments, the metal ion associated disorder is an iron ion associated disorder. In a further embodiment, the metal ion associated disorder is a neurological disorder.

In yet a further aspect of the invention, there is provided a use of a compound of formula (I) or a pharmaceutically acceptable salt or solvate thereof in the manufacture of a medicament for treating or preventing metal ion associated disorder. In some embodiments, the metal ion associated disorder is an iron ion associated disorder. In a further embodiment, the metal ion associated disorder is a neurological disorder.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$ alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

The term "haloalkyl" as used herein refers to an alkyl group as defined above where one or more hydrogen atoms have been replaced with a halogen atom and includes perhalogenated alkyl groups. Examples of suitable haloalkyl groups include fluoromethyl, difluoromethyl, trifluoromethyl, chloromethyl, dichloromethyl, trichloromethyl, chlorofluoromethyl, difluorochloromethyl, dichlorofluoromethyl, bromomethyl, iodomethyl, 1-fluoroethyl, 2-fluoroethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-chloropropyl, 2-chloropropyl, 3-chloropropyl, and the like.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 10 membered cycloalkyl group includes 3, 4, 5, 6, 7, 8, 9 or 10 carbon atoms. Examples of suitable cycloalkyl groups include, but are not limited to, cyclopropyl, cyclobutyl, cyclopentyl, cyclohexyl, cycloheptyl, cyclooctyl, cyclononyl and cyclodecyl.

As used herein, the term "cycloalkenyl" refers to an unsaturated cyclic hydrocarbon. The cycloalkenyl ring may include a specified number of carbon atoms. For example, a 5 to 10 membered cycloalkenyl group includes 5, 6, 7, 8, 9 or 10 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl, cyclooctatrienyl, cyclononenyl, cyclononadienyl, cyclononatrienyl, cyclodecenyl, cyclodecadienyl and cyclodecatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon, such as a cycloalkyl or cycloalkenyl defined above, in which one to four carbon atoms have been replaced by heteroatoms independently selected from the group consisting of N, N(R), S, S(O), $S(O)_2$ and O. A heterocyclic ring may be saturated or unsaturated but not aromatic. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl and tetrazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$ alkyl, $C_{2-6}$ alkenyl, $C_{3-6}$ cycloalkyl, oxo (=O), —OH, —SH, $C_{1-6}$alkylO—, $C_{2-6}$ alkenylO—, $C_{3-6}$ cycloalkylO—, $C_{1-6}$ alkylS—, $C_{2-6}$ alkenylS—, $C_{3-6}$ cycloalkylS—, —$CO_2$H, —$CO_2C_{1-6}$ alkyl, —$NH_2$, —NH($C_{1-6}$ alkyl), —N($C_{1-6}$ alkyl)$_2$, —NH(phenyl), —N(phenyl)$_2$, oxo, —CN, —$NO_2$, -halogen, —$CF_3$, —$OCF_3$, —$SCF_3$, —$CHF_2$, —$OCHF_2$, —$SCHF_2$, -phenyl, -heterocyclyl, -heteroaryl, —Oheteroaryl, —Oheterocyclyl, —Ophenyl, —C(=O)phenyl, —C(=O)$C_{1-6}$ alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2$H, —$CO_2CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, malonic, malic (L), lactic (DL), mandelic (DL), gluconic, carbonic, benzoic, succinic, oxalic, phenylacetic, methanesulphonic, toluenesulphonic, camphorsulphonic, benzenesulphonic, salicylic, cinnamic, cyclamic, sulphanilic, aspartic, glutamic, glutaric, galactaric, gentisic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, aluminium, zinc, lysine, histidine, meglumine, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The compounds of the invention may also be in the form of solvates, including hydrates. The term "solvate" is used herein to refer to a complex of variable stoichiometry formed by a solute (a compound of formula (I)) and a solvent. Such solvents should not interfere with the biological activity of the solute. Solvents that may be included in a solvate include, but are not limited to, water, ethanol, propanol, and acetic acid. Methods of solvation are generally known within the art.

The term "pro-drug" is used in its broadest sense and encompasses those derivatives that are converted in vivo to the compounds of formula (I). Such derivatives would readily occur to those skilled in the art and include, for example, compounds where a free hydroxy group is converted into an ester derivative or a ring nitrogen is converted to an N-oxide. Examples of ester derivatives include alkyl esters, phosphate esters and those formed from amino acids. Conventional procedures for the preparation of suitable prodrugs are described in text books such as "Design of Prodrugs" Ed. H. Bundgaard, Elsevier, 1985.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

The compounds of the invention may also exist in the form of rotational isomers or conformers where there is restricted or hindered rotation about a single bond.

Any formula or structure given herein, including Formula I compounds are also intended to represent unlabelled forms as well as isotopically labelled forms of the compounds for use as medicaments or as a study tool. The may include metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labelled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to 2H (deuterium, D), 3H (tritium), 10B, 11C, 13C, 14C, 15N, 18F, 31P, 32P, 35S, 36Cl and 125I. Various isotopically labelled compounds of the present disclosure, for example those into which radioactive isotopes such as 3H, 13C and 14C are incorporated. In addition to use as pharmaceutical treatments, such isotopically labelled compounds may be useful.

Compounds of the Invention

The present invention provides metal ion modulating compounds, particularly iron selective ion modulating compounds. Such modulators may have one or more of the desirable properties of: orally deliverable; low liver extraction, non-toxicity and the ability to modulate metals, particularly iron in the central nervous system (CNS). Advantageous metal selectivity, affinity and kinetic stability of the complexes formed are also provided by preferred compounds.

In order for a modulating compound to exert its pharmacological effect, it must be able to reach the target sites at a sufficient concentration. Therefore, a preferred key property of an orally active iron modulator is its ability to be efficiently absorbed from the gastrointestinal tract (GI).

The metabolic properties of modulator agents play a critical role in determining both their efficacy and toxicity. Toxicity associated with iron originates from a number of factors, but critically on their ability to inhibit many iron-containing enzymes like tyrosine hydroxylase (the brain enzyme involved in the biosynthesis of L-DOPA) and ribonucleotide reductase. Thus, in a first aspect the present invention provides a compound of formula (I):

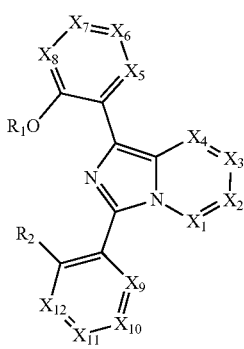

(I)

wherein
each of $X_1$ to $X_{12}$ are independently selected from the group consisting of N and $CR_3$, wherein 0, 1, 2 or 3 of $X_1$ to $X_{12}$ are N;
$R_1$ is selected from the group consisting of hydrogen, alkyl, alkenyl, alkynyl, $C(O)R_4$ and $C(S)R_4$;
$R_2$ is selected from the group consisting of hydrogen, halo, $OR_5$, $SR_5$, $C(O)R_4$, $C(S)R_4$, $NO_2$, CN, $N(R_6)_2$, $OS(O)_n N(R_6)_2$ and $OS(O)_n R_4$;
each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(R_7)_2)_m SC(S)R_4$, $(C(R_7)_2)_m OC(S)R_4$, $(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)/R_4$, $(C(R_7)_2)_m N(R_6)C(O)N(R_6)_2$ and $(C(R_7)_2)_m N(R_6)C(S)N(R_6)_2$;
$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;
$R_5$ is selected from the group consisting of hydrogen, alkyl, alkenyl, alkynyl, haloalkyl, cycloalkyl, cycloalkenyl, aryl, heterocyclyl, heteroaryl $C(O)$alkyl, $C(O)$alkenyl, $C(O)$alkynyl, $S(O)R_4$ and $S(O)_n N(R_6)_2$;
$R_6$ is selected from the group consisting of hydrogen, alkyl, alkenyl, alkynyl, haloalkyl, cycloalkyl, cycloalkenyl, aryl, heterocyclyl and heteroaryl;
each $R_7$ is independently selected from the group consisting of hydrogen, alkyl, alkenyl, alkynyl and haloalkyl;
m is 0 or an integer from 1 to 6;
n is 1 or 2;
wherein each alkyl, alkenyl, alkynyl, cycloalkyl, cycloalkenyl, aryl, heterocyclyl and heteroaryl is optionally substituted;
or a pharmaceutically acceptable salt or solvate thereof;
with the proviso that when $R_1$ is methyl, $X_1$, $X_2$, $X_3$, $X_4$, $X_5$, $X_6$, $X_8$, $X_9$, $X_{10}$, $X_{11}$ and $X_{12}$ are each $CR_3$ where $R_3$ is hydrogen and $X_7$ is $CR_3$ where $R_3$ is $OCH_3$, $R_2$ is not hydrogen.

In some embodiments, $X_1$ to $X_{12}$ are each independently $CR_3$. In other embodiments, one of $X_1$ to $X_{12}$ is N and the remainder are $CR_3$. In yet other embodiments, two of $X_1$ to $X_{12}$ are N and the remainder are $CR_3$. In yet other embodiments, three of $X_1$ to $X_{12}$ are N and the remainder are $CR_3$.

In some embodiments, one of $X_1$ to $X_4$ is N. In other embodiments, one of $X_5$ to $X_8$ is N. In yet other embodiments, one of $X_9$ to $X_{12}$ is N. In particular embodiments one of $X_1$, $X_4$, $X_5$, $X_6$, $X_7$, $X_8$, $X_9$ and $X_{11}$ is N.

In yet other embodiments, one of $X_1$ to $X_4$ and one of $X_5$ to $X_8$ are N or one of $X_5$ to $X_8$ and one of $X_9$ to $X_{12}$ are N or one of $X_1$ to $X_4$ and one of $X_9$ to $X_{12}$ are N. In some embodiments, two of $X_1$, $X_3$, $X_4$, $X_5$ and $X_{10}$ are N. In particular embodiments, $X_1$ and $X_5$, $X_1$ and $X_7$, $X_3$ and $X_7$, $X_4$ and $X_7$ or $X_5$ and $X_{10}$ are N. In some embodiments, one of $X_1$ to $X_4$, one of $X_5$ to $X_8$ and one of $X_9$ to $X_{12}$ are N. In other embodiments, one of $X_1$ to $X_4$ and two of $X_5$ to $X_8$ are N. In yet other embodiments, two of $X_5$ to $X_8$ are N and one of $X_9$ to $X_{12}$ are N. In some embodiments, three of $X_1$, $X_5$, $X_7$ and $X_9$ are N.

In some embodiments, where 2 or 3 of $X_1$ to $X_{12}$ are N, no more than two nitrogen atoms are located adjacent to each other in a ring. For example, if $X_5$ and $X_7$ are both N, $X_6$ could not be N or if $X_1$, located adjacent to the ring junction N, is N, $X_2$ could not be N.

In some embodiments, when $X_3$ is N, $X_4$ is not $CR_3$ where $R_3$ is $NH_2$.

In some embodiments, when $X_1$ to $X_{12}$ are each $CR_3$, $R_2$ is not H.

In particular embodiments, one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, SH, fluoro, chloro, bromo, $OC_{1-6}$ alkyl, $SC_{1-6}$alkyl, $C(O)$ $OC_{1-6}$ alkyl, $NO_2$, CN, $NH_2$, $OS(O)_2NH_2$, $OS(O)_2NH(C_{1-6}$ alkyl), $OS(O)_2N(C_{1-6}$alkyl$)_2$ and $OS(O)_nC_{1-6}$ alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

Each $R_3$ is selected from the group consisting of hydrogen, halo, $C_{1-6}$ alkyl, $C_{2-6}$ alkenyl, $C_{1-6}$ haloalkyl, cycloalkyl, cycloalkenyl, aryl, heterocyclyl, heteroaryl, OH, $CH_2OH$, SH, $CH_2SH$, $OC_{1-6}$ alkyl, $SC_{1-6}$alkyl, $CH_2OC_{1-6}$ alkyl, $CH_2SC_{1-6}$ alkyl, $OC(O)C_{1-6}$ alkyl, $CH_2OC(O)C_{1-6}$ alkyl, $C(O)C_{1-6}$ alkyl, $CH_2C(O)C_{1-6}$ alkyl, $CO_2H$, $CH_2CO_2H$, $C(O)OC_{1-6}$ alkyl, $CH_2C(O)OC_{1-6}$ alkyl, $CONH_2$, $CH_2CONH_2$, CN, $CH_2CN$, $NO_2$, $CH_2NO_2$, $NH_2$, $NH(C_{1-6}$ alkyl), $N(C_{1-6}$alkyl$)_2$, $CH_2NH_2$, $CH_2NH(C_{1-6}$alkyl), $CH_2N(C_{1-6}$ alkyl$)_2$, $SO_2H$, $CH_2SO_2H$, $SO_3H$, $CH_2SO_3H$, $S(O)_2C_{1-6}$ alkyl, $CH_2S(O)_2C_{1-6}$ alkyl, $S(O)_2$ $OC_{1-6}$alkyl, $CH_2S(O)_2OC_{1-6}$ alkyl, $S(O)_2NH_2$, $S(O)_2NH(C_{1-6}$ alkyl), $S(O)_2N(C_{1-6}$alkyl$)_2$, $CH_2S(O)_2NH_2$, $CH_2S(O)_2$ $NH(C_{1-6}$ alkyl), $CH_2S(O)_2N(C_{1-6}$ alkyl$)_2$, $NHC(O)NH_2$, $NHC(O)NH(C_{1-6}$ alkyl), $NHC(O)N(C_{1-6}$alkyl$)_2$ $CH_2NHC(O)NH_2$, $CH_2NHC(O)NH(C_{1-6}$alkyl) and $CH_2NHC(O)N(C_{1-6}$alkyl$)_2$; especially hydrogen, halo, $C_{1-6}$ alkyl, $C_{1-6}$ haloalkyl, OH, $CH_2OH$, $OC_{1-6}$ alkyl, $SC_{1-6}$ alkyl, $CH_2OC_{1-6}$ alkyl, $CH_2SC_{1-6}$ alkyl, $OC(O)C_{1-6}$ alkyl, $CH_2OC(O)C_{1-6}$ alkyl, $C(O)C_{1-6}$ alkyl, $CH_2C(O)C_{1-6}$ alkyl, $C(O)OC_{1-6}$alkyl, $CH_2C(O)OC_{1-6}$ alkyl, CN, $CH_2CN$, $NO_2$, $CH_2NO_2$, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$; more especially hydrogen, halo, $C_{1-3}$ alkyl, $C_{1-3}$ haloalkyl, OH, $OC_{1-3}$ alkyl, $SC_{1-3}$ alkyl, $CH_2OC_{1-3}$ alkyl, $CH_2SC_{1-3}$alkyl, $C(O)C_{1-3}$alkyl, $CH_2C(O)C_{1-3}$alkyl, $C(O)OC_{1-3}$ alkyl, $CH_2C(O)OC_{1-3}$ alkyl, CN, $CH_2CN$, $NO_2$, $CH_2NO_2$, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$.

$R_4$ is selected from the group consisting of hydrogen, $C_{1-6}$ alkyl, $C_{1-6}$ haloalkyl, $OC_{1-6}$ alkyl and $OC_{1-6}$haloalkyl, especially hydrogen, $C_{1-3}$ alkyl, $C_{1-3}$ haloalkyl, $OC_{1-3}$ alkyl and $OC_{1-3}$ haloalkyl, more especially $CH_3$, $CF_3$, $OCH_3$ and $OCF_3$;

$R_5$ is selected from hydrogen, $C_{1-6}$ alkyl, $C_{1-6}$ haloalkyl, $C(O)C_{1-6}$ alkyl, $S(O)_2C_{1-6}$ alkyl, $S(O)_2OC_{1-6}$ alkyl, $S(O)_2$ $NH_2$, $S(O)_2NH(C_{1-6}$ alkyl) and $S(O)_2N(C_{1-6}$ alkyl$)_2$, especially $C_{1-3}$ alkyl, $C_{1-3}$ haloalky and $C(O)C_{1-3}$alkyl; and $R_6$ is selected from hydrogen and $C_{1-6}$ alkyl; especially hydrogen and $C_{1-3}$ alkyl; and each $R_7$ is independently selected from the group consisting of hydrogen, alkyl and haloalkyl, especially hydrogen.

In some embodiments, the compound of formula (I) is a compound of formula (II):

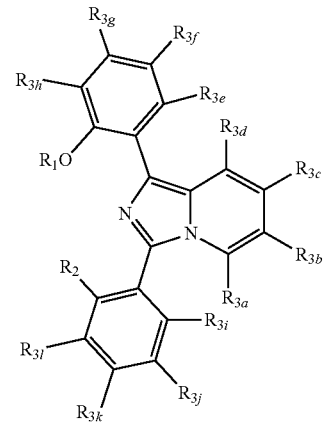

(II)

wherein $R_1$ and $R_2$ are as defined for formula (I) and $R_{3a}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$ aryl, $(C(R_7)_2)_m$heterocyclyl, $(C(R_7)_2)_m$heteroaryl, $(C(R_7)_2)_m$ $OR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)$ $R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)$ $N(R_6)_2$ and $(C(R_7)_2)_mN(R_6)C(S)N(R_6)_2$, wherein $R_4$, $R_5$, $R_6$, $R_7$ and m are as defined for formula (I);

or a pharmaceutically acceptable salt or solvate thereof; with the proviso that when $R_1$ is methyl, $R_{3a}$, $R_{3b}$, $R_{3c}$, $R_{3d}$, $R_{3e}$, $R_{3f}$, $R_{3h}$, $R_{3i}$, $R_{3j}$, $R_{3k}$ and $R_{3l}$ are each hydrogen and $R_{3g}$ is $OCH_3$, $R_2$ is not hydrogen.

In some embodiments, when $R_2$ is hydrogen, then one or more of $R_{3i}$, $R_{3j}$, $R_{3k}$ and $R_{3l}$ are not hydrogen.

In some embodiments, $R_2$ is not hydrogen.

In particular embodiments of formula (II), one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_nC_{1-6}$ alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$;

$R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl)$_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl)$_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl)$_2$, $CH_2NH_2$, $CH_2NH(C_{1-6}$ alkyl) and $CH_2N(C_{1-6}$ alkyl)$_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl) and $N(C_{1-3}$ alkyl)$_2$, $CH_2NH_2$, $CH_2NH(C_{1-3}$ alkyl) and $CH_2N(C_{1-3}$ alkyl)$_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (II) are compounds 1, 2, 5 to 51, 62 to 78, 86 to 91, 96 to 101, 109, 124 and 131 as shown in Table 2.

In some embodiments, the compound of formula (I) is a compound of formula (III):

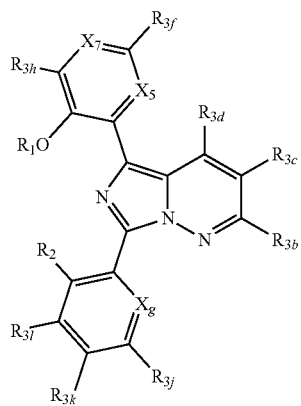
(III)

wherein $X_5$ is N or $CR_{3e}$; $X_7$ is N or $CR_{3g}$; $X_9$ is N or $CR_{3i}$; wherein none, one or two of $X_5$, $X_7$ and $X_9$ is N;

$R_1$ and $R_2$ are as defined for formula (I) and $R_{3b}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (III), one or more of the following applies:

$X_5$ is N or $X_7$ is N;

$X_5$ and $X_7$ are both N and $X_9$ is $CR_{3i}$;

$X_5$ and $X_9$ are both N and $X_7$ is $CR_{3g}$;

$X_7$ and $X_9$ are both N and $X_5$ is $CR_{3e}$;

$X_5$ is $CR_{3e}$;

$X_7$ is $CR_{3g}$;

$X_9$ is $CR_{3i}$;

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$ alkyl), $OS(O)_2N(C_{1-6}$ alkyl)$_2$ and $OS(O)_nC_{1-6}$ alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl$)_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl$)_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl), $N(C_{1-3}$alkyl$)_2$, $CH_2NH_2$, $CH_2NH(C_{1-3}$ alkyl) and $CH_2N(C_{1-3}$ alkyl$)_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (III) are compounds 102 to 106, 115 to 123 and 181 to 184 as shown in Table 2.

In some embodiments, the compound of formula (I) is a compound of formula (IV):

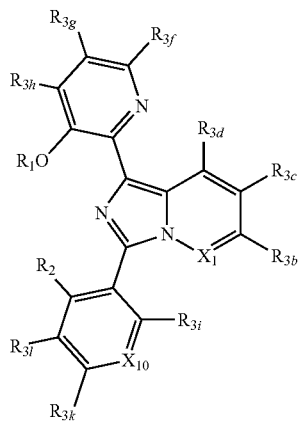

(IV)

wherein $X_1$ is N or $CR_{3a}$; $X_{10}$ is N or $CR_{3j}$;

$R_1$ and $R_2$ are as defined for formula (I) and $R_{3a}$ to $R_{3d}$ and $R_{3f}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$ aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_m$ $C(S)R_4$, $(C(R_7)_2)_mOC(O)R_4$, $(C(R_7)_2)_mSC(S)R_4$, $(C(R_7)_2)_m$ $OC(S)R_4$, $(C(R_7)_2)_mSC(O)R_4$, $(C(R_7)_2)_mCN$, $(C(R_7)_2)_m$ $NO_2$, $(C(R_7)_2)_mN(R_6)_2$, $(C(R_7)_2)_mS(O)_nR_4$, $(C(R_7)_2)_mN(R_6)$ $C(O)N(R_6)_2$ and $(C(R_7)_2)_mN(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (IV), one or more of the following applies:

$X_1$ is N or $X_{10}$ is N;

$X_1$ is $CR_{3a}$;

$X_{10}$ is $CR_{3j}$;

$R_1$ is selected from the group consisting of hydrogen, $C_{1-6}$alkyl, $C_{2-6}$ alkenyl, $C(O)C_{1-6}$ alkyl and $C(O)OC_{1-6}$ alkyl; especially, hydrogen, $C_{1-6}$alkyl and $C(O)C_{1-6}$alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_nC_{1-6}$ alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl$)_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl$)_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl), $N(C_{1-3}$alkyl$)_2$, $CH_2NH_2$, $CH_2NH(C_{1-3}$ alkyl) and $CH_2N(C_{1-3}$ alkyl$)_2$ more especially hydrogen, fluoro, chloro, CN, $CH_3$, $OCH_3$ and $CH_2N(CH_3)_2$;

or a pharmaceutically acceptable salt or solvate thereof.

Particular compounds of formula (IV) are compounds 3, 4, 52 to 61, 79 to 85, 92 to 94, 115 to 123 and 126 to 130 as shown in Table 2.

In some embodiments, the compound of formula (I) is a compound of formula (V):

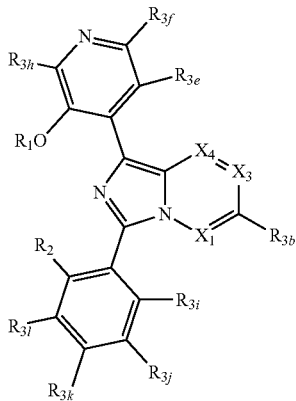

(V)

wherein $X_1$ is N or $CR_{3a}$; $X_3$ is N or $CR_{3c}$; $X_4$ is N or $CR_{3d}$; wherein none, one or two of $X_1$, $X_3$ and $X_4$ is N;

$R_1$ and $R_2$ are as defined for formula (I) and $R_{3a}$ to $R_{3f}$ and $R_{3h}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$, wherein $R_4$, $R_5$, $R_6$, $R_7$ and m are as defined for formula (I);

or a pharmaceutically acceptable salt or solvate thereof.

In particular embodiments of formula (V), one or more of the following applies:

$X_1$ is N or $X_3$ is N or $X_4$ is N;
$X_1$ is $CR_{3a}$;
$X_3$ is $CR_{3c}$;
$X_4$ is $CR_{3d}$;
$X_1$ and $X_4$ are N and $X_3$ is $CR_{3c}$;
when $X_1$ is $CR_{3a}$ where $R_{3a}$ is hydrogen and $X_3$ is N, $X_4$ is not $CR_{3d}$ where $R_{3d}$ is NH$_2$;

$R_1$ is selected from the group consisting of hydrogen, $C_{1-6}$alkyl, $C_{2-6}$ alkenyl, $C(O)C_{1-6}$alkyl and $C(O)OC_{1-6}$ alkyl; especially, hydrogen, $C_{1-6}$alkyl and $C(O)C_{1-6}$alkyl, more especially hydrogen and $C_{1-3}$alkyl, most especially hydrogen and CH$_3$;

$R_2$ is selected from the group consisting of hydrogen, OH, fluoro, chloro, bromo, $OC_{1-6}$alkyl, $SC_{1-6}$alkyl, $C(O)OC_{1-6}$ alkyl, NO$_2$, CN, NH$_2$, $OS(O)_2$NH$_2$, $OS(O)_2$NH(C$_{1-6}$alkyl), $OS(O)_2$N(C$_{1-6}$alkyl)$_2$ and $OS(O)_n$C$_{1-6}$ alkyl; especially hydrogen, OH, halo, CN, NO$_2$, $OC_{1-6}$alkyl and CO$_2$C$_{1-6}$ alkyl; more especially hydrogen, OH, halo, CN, NO$_2$, $OC_{1-6}$ alkyl and CO$_2$C$_{1-6}$ alkyl; even more especially hydrogen, OH, halo, CN, NO$_2$, OCH$_3$ and CO$_2$CH$_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, CF$_3$ and CH$_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and CH$_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and CH$_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$alkyl, $C_{1-6}$haloalkyl and $CO_2C_{1-6}$alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, CH$_3$ and CO$_2$CH$_3$, $R_{3k}$ is selected from the group consisting of hydrogen, halo, $C_{1-6}$ alkyl, $C_{1-6}$ haloalkyl, $CO_2C_{1-6}$ alkyl, CN, NH$_2$, NH($C_{1-6}$ alkyl) and N($C_{1-6}$ alkyl)$_2$, especially hydrogen, fluoro, chloro, bromo, $C_{1-3}$ alkyl, $C_{1-3}$haloalkyl, $CO_2C_{1-3}$ alkyl, CN, NH$_2$, NH($C_{1-3}$ alkyl) and N($C_{1-3}$ alkyl)$_2$, more especially hydrogen, chloro, CH$_3$, CN, CO$_2$CH$_3$, N(CH$_3$)$_2$ and N(CH$_2$CH$_3$)$_2$;

$R_{3l}$ is selected from the group consisting of hydrogen, halo, $C_{1-6}$ alkyl, $C_{1-6}$ haloalkyl, $OC_{1-6}$ alkyl, CN, NH$_2$, NH($C_{1-6}$ alkyl), N($C_{1-6}$ alkyl)$_2$, CH$_2$NH$_2$, CH$_2$NH($C_{1-6}$ alkyl) and CH$_2$N($C_{1-6}$ alkyl)$_2$, especially hydrogen, fluoro, chloro, bromo, $C_{1-3}$alkyl, $C_{1-3}$haloalkyl, $OC_{1-3}$alkyl, CN, NH$_2$, NH($C_{1-3}$alkyl), N($C_{1-3}$alkyl)$_2$, CH$_2$NH$_2$, CH$_2$NH($C_{1-3}$ alkyl) and CH$_2$N($C_{1-3}$ alkyl)$_2$, more especially hydrogen, fluoro, chloro, CN, CH$_3$, OCH$_3$ and CH$_2$N(CH$_3$)$_2$;

or a pharmaceutically acceptable salt or solvate thereof.

Particular compounds of formula (V) are compounds 110 to 114 and 174 to 186 as shown in Table 2.

In some embodiments, the compound of formula (I) is a compound of formula (VI):

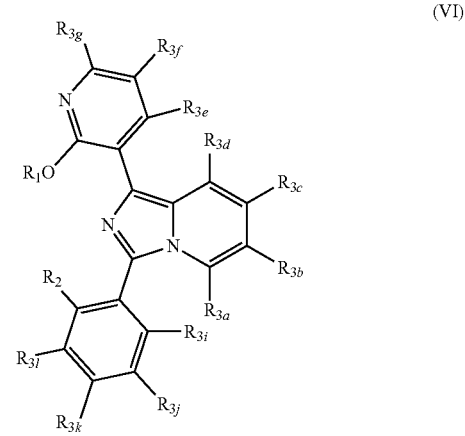

(VI)

wherein $R_1$ and $R_2$ are as defined for formula (I) and $R_{3a}$ to $R_{3g}$ and $R_{3i}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$, wherein $R_4$, $R_5$, $R_6$, $R_7$ and m are as defined for formula (I); or a pharmaceutically acceptable salt or solvate thereof.

In particular embodiments of formula (VI), one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$ alkyl), $OS(O)_2N(C_{1-6}$ alkyl)$_2$ and $OS(O)_nC_{1-6}$alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$alkyl, $C_{1-6}$haloalkyl and $CO_2C_{1-6}$alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl)$_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl)$_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl)$_2$, $CH_2NH_2$, $CH_2NH(C_{1-6}$ alkyl) and $CH_2N(C_{1-6}$ alkyl)$_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl), $N(C_{1-3}$alkyl)$_2$, $CH_2NH_2$, $CH_2NH(C_{1-3}$ alkyl) and $CH_2N(C_{1-3}$ alkyl)$_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (VI) are compounds 132 to 152 and 168 as shown in Table 2.

In some embodiments, the compound of formula (I) is a compound of formula (VII):

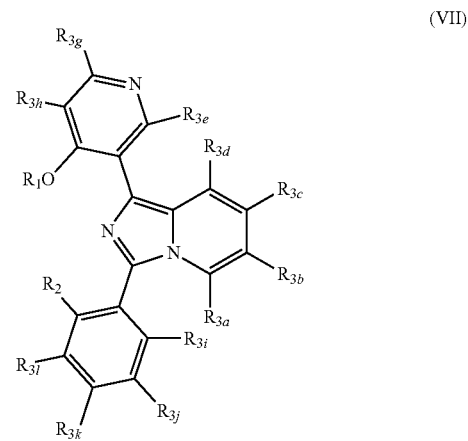

(VII)

wherein $R_1$ and $R_2$ are as defined for formula (I) and $R_{3a}$ to $R_{3e}$ and $R_{3g}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (VII), one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$ alkyl), $OS(O)_2N(C_{1-6}$ alkyl)$_2$ and $OS(O)_nC_{1-6}$alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$alkyl, $C_{1-6}$haloalkyl and $CO_2C_{1-6}$alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl)$_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl)$_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl)$_2$, $CH_2NH_2$, $CH_2NH(C_{1-6}$ alkyl) and $CH_2N(C_{1-6}$ alkyl)$_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl), $N(C_{1-3}$alkyl)$_2$, $CH_2NH_2$, $CH_2NH(C_{1-3}$ alkyl) and $CH_2N(C_{1-3}$ alkyl)$_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (VII) are compounds 153 to 167 and 169 to 173 as shown in Table 2.

In some embodiments, the compound of formula (I) is a compound of formula (VIII):

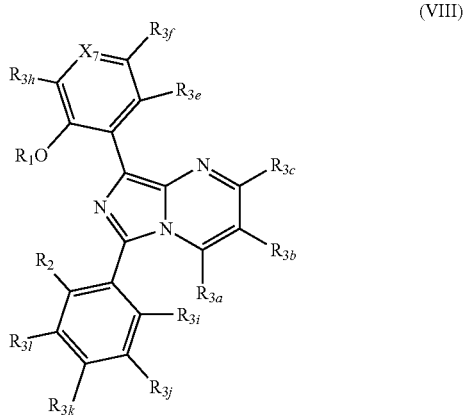

(VIII)

wherein $X_7$ is N or $CR_{3g}$, $R_1$ and $R_2$ are as defined for formula (I) and $R_{3a}$ to $R_{3c}$ and $R_{3e}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (VIII), one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$ alkyl), $OS(O)_2N(C_{1-6}$ alkyl)$_2$ and $OS(O)_n C_{1-6}$alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl)$_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl)$_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$alkyl, $C_{1-6}$haloalkyl, $OC_{1-6}$alkyl, CN, $NH_2$, $NH(C_{1-6}$alkyl), $N(C_{1-6}$alkyl$)_2$, $CH_2NH_2$, $CH_2NH(C_{1-6}$alkyl) and $CH_2N(C_{1-6}$alkyl$)_2$, especially hydrogen, fluoro, chloro, bromo, $C_{1-3}$alkyl, $C_{1-3}$haloalkyl, $OC_{1-3}$ alkyl, CN, $NH_2$, $NH(C_{1-3}$alkyl), $N(C_{1-3}$alkyl$)_2$, $CH_2NH_2$, $CH_2NH(C_{1-3}$alkyl) and $CH_2N(C_{1-3}$alkyl$)_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (VIII) are compounds 107, 108. 185 and 186 as shown in Table 2.

In some embodiments, the compound of formula (I) is a compound of formula (IX):

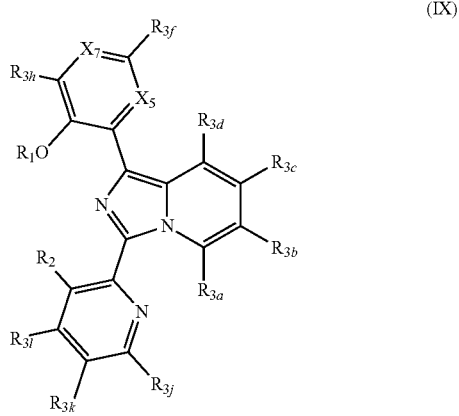

(IX)

wherein $X_5$ is N or $CR_{3e}$; $X_7$ is N or $CR_{3g}$; $R_1$ and $R_2$ are as defined for formula (I) and $R_{3a}$ to $R_{3h}$ and $R_{3j}$ to $R_{3l}$ are each independently selected from the group consisting of hydrogen, halo, alkyl, alkenyl, alkynyl, haloalkyl, $(C(R_7)_2)_m$ cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (IX), one or more of the following applies:

$X_5$ is N and $X_7$ is $CR_{3g}$;
$X_7$ is N and $X_5$ is $CR_{3e}$;
$X_5$ and $X_7$ are N;

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_n C_{1-6}$alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3j}$ is selected from the group consisting of hydrogen, halo, $C_{1-6}$alkyl, $C_{1-6}$haloalkyl and $CO_2C_{1-6}$alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl$)_2$, especially hydrogen, fluoro, chloro, bromo, $C_{1-3}$ alkyl, $C_{1-3}$haloalkyl, $CO_2C_{1-3}$ alkyl, CN, $NH_2$, $NH(C_{1-3}$ alkyl) and $N(C_{1-3}$ alkyl$)_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$, especially hydrogen, fluoro, chloro, bromo, $C_{1-3}$ alkyl, $C_{1-3}$ haloalkyl, $OC_{1-3}$ alkyl, CN, $NH_2$, $NH(C_{1-3}$ alkyl) $N(C_{1-3}$alkyl$)_2$, $CH_2NH_2$, $CH_2NH(C_{1-3}$ alkyl) and $CH_2N(C_{1-3}$ alkyl$)_2$, more especially hydrogen, fluoro, chloro, CN, $CH_3$, $OCH_3$ and $CH_2N(CH_3)_2$;

or a pharmaceutically acceptable salt or solvate thereof.

A particular compound of formula (IX) is compound 95 as shown in Table 2.

In some embodiments, the compound of formula (I) is a compound of formula (X):

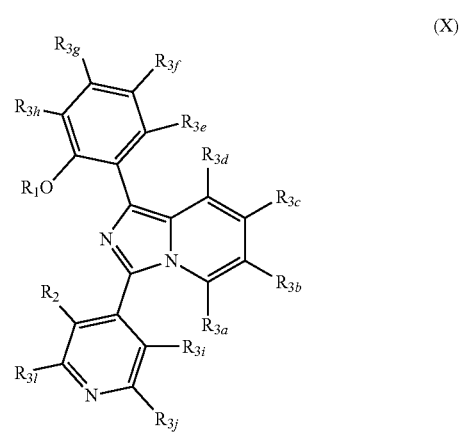

(X)

wherein $R_1$ and $R_2$ are as defined for formula (I) and $R_{3a}$ to $R_{3j}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (X), one or more of the following applies:

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$ alkyl), $OS(O)_2N(C_{1-6}$ alkyl$)_2$ and $OS(O)_n C_{1-6}$ alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_3$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro, bromo and $CH_3$;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3i}$ is selected from the group consisting of hydrogen, halo, $C_{1-6}$alkyl and $C_{1-6}$haloalkyl, especially hydrogen, fluoro, chloro, bromo, $C_{1-3}$ alkyl and $C_{1-3}$ haloalkyl, more especially hydrogen, fluoro and chloro;

$R_{3j}$ is selected from the group consisting of hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$, especially hydrogen, fluoro, chloro, bromo, $C_{1-3}$alkyl, $C_{1-3}$haloalkyl, $OC_{1-3}$alkyl, CN, $NH_2$, $NH(C_{1-3}$alkyl), $N(C_{1-3}$alkyl$)_2$, $CH_2NH_2$, $CH_2NH(C_{1-3}$ alkyl) and $CH_2N(C_{1-3}$ alkyl$)_2$, more especially hydrogen, fluoro, chloro, CN, $CH_3$, $OCH_3$ and $CH_2N(CH_3)_2$;

or a pharmaceutically acceptable salt or solvate thereof. A particular compound of formula (X) is compound 125 as shown in Table 2.

In some embodiments, the compound of formula (I) is a compound of formula (XI):

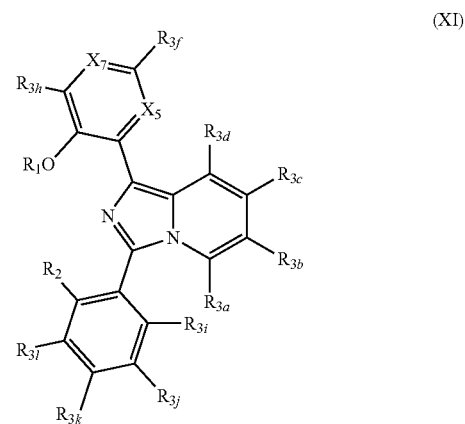

(XI)

wherein $X_5$ is N and $X_7$ is $CR_{3g}$; or $X_5$ is $CR_{3e}$ and $X_7$ is N; $R_1$ and $R_2$ are as defined for formula (I) and $R_{3a}$ to $R_{3l}$ are each independently selected from the group consisting of hydrogen, halo, alkyl, alkenyl, alkynyl, haloalkyl, $(C(R_7)_2)_m$ cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_u S(O)_1 R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I);

or a pharmaceutically acceptable salt or solvate thereof.

In particular embodiments of formula (IX), one or more of the following applies:

$X_5$ is N and $X_7$ is $CR_{3g}$;

$R_1$ is selected from the group consisting of hydrogen, $C_{1-6}$ alkyl, $C_{2-6}$ alkenyl, $C(O)C_{1-6}$ alkyl and $C(O)OC_{1-6}$ alkyl; especially, hydrogen, $C_{1-6}$ alkyl and $C(O)C_{1-6}$ alkyl, more especially hydrogen and $C_{1-3}$alkyl, most especially hydrogen and $CH_3$;

$R_2$ is selected from the group consisting of hydrogen, OH, fluoro, chloro, bromo, $OC_{1-6}$ alkyl, $SC_{1-6}$alkyl, $C(O)OC_{1-6}$ alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_n C_{1-6}$alkyl; especially hydrogen, OH, halo, CN, $NO_2$, $OC_{1-6}$ alkyl and $CO_2C_{1-6}$ alkyl; more especially hydrogen, OH, halo, CN, $NO_2$, $OC_{1-6}$ alkyl and $CO_2C_{1-6}$ alkyl; even more especially hydrogen, OH, halo, CN, $NO_2$, $OCH_3$ and $CO_2CH_3$; most especially OH;

$R_{3a}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3b}$ is selected from the group consisting of hydrogen $C_{1-6}$ alkyl and $C_{1-6}$ haloalkyl, especially hydrogen, $C_{1-3}$ alkyl and $C_{1-3}$ haloalkyl, more especially hydrogen, $CF_3$ and $CH_3$;

$R_{3c}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen and $CH_3$;

$R_{3d}$ is selected from the group consisting of hydrogen, $C_{1-6}$ alkyl and $C_{1-6}$ haloalkyl, especially hydrogen, $C_{1-3}$ alkyl and $C_{1-3}$ haloalkyl, more especially hydrogen;

$R_{3e}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen and fluoro;

$R_{3f}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3g}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and $CF_3$;

$R_{3h}$ is selected from the group consisting of hydrogen, halo, $C_{1-6}$ alkyl and $C_{1-6}$ haloalkyl, especially hydrogen, fluoro, chloro, bromo, $C_{1-3}$ alkyl and $C_{1-3}$ haloalkyl, more especially hydrogen, fluoro and bromo;

$R_{3j}$ is selected from the group consisting of hydrogen, halo, $C_{1-6}$ alkyl, $C_{1-6}$ haloalkyl and $CO_2C_{1-6}$ alkyl, especially hydrogen, fluoro, chloro, bromo, $C_{1-3}$ alkyl, $C_{1-3}$ haloalkyl and $CO_2C_{1-3}$ alkyl, more especially hydrogen, fluoro, chloro, $CH_3$ and $CO_2CH_3$, $R_{3k}$ is selected from the group consisting of hydrogen, halo, $C_{1-6}$ alkyl, $C_{1-6}$ haloalkyl, $CO_2C_{1-6}$ alkyl, CN, $NH_2$, $NH(C_{1-6}$ alkyl) and $N(C_{1-6}$ alkyl$)_2$, especially hydrogen, fluoro, chloro, bromo, $C_{1-3}$ alkyl, $C_{1-3}$ haloalkyl, $CO_2C_{1-3}$ alkyl, CN, $NH_2$, $NH(C_{1-3}$ alkyl) and $N(C_{1-3}$ alkyl$)_2$, more especially hydrogen, chloro, $CH_3$, CN, $CO_2CH_3$, $N(CH_3)_2$ and $N(CH_2CH_3)_2$;

$R_{3l}$ is selected from the group consisting of hydrogen, halo, $C_{1-6}$ alkyl, $C_{1-6}$ haloalkyl, $OC_{1-6}$ alkyl, CN, $NH_2$, $NH(C_{1-6}$ alkyl), $N(C_{1-6}$ alkyl$)_2$, $CH_2NH_2$, $CH_2NH(C_{1-6}$ alkyl) and $CH_2N(C_{1-6}$ alkyl$)_2$, especially hydrogen, fluoro, chloro, bromo, $C_{1-3}$ alkyl, $C_{1-3}$ haloalkyl, $OC_{1-3}$ alkyl, CN, $NH_2$, $NH(C_{1-3}$ alkyl) $N(C_{1-3}$ alkyl$)_2$, $CH_2NH_2$, $CH_2NH(C_{1-3}$ alkyl) and $CH_2N(C_{1-3}$ alkyl$)_2$, more especially hydrogen, fluoro, chloro, CN, $CH_3$, $OCH_3$ and $CH_2N(CH_3)_2$;

or a pharmaceutically acceptable salt or solvate thereof.

Particular compounds of formula (XI) are compounds 52 to 61, 79 to 85, 92 to 94, 110 to 114, 126 to 128 and 130 as shown in Table 2.

The compounds of formula (I) may be made by methods known in the art. For example, Scheme 1 shows the preparation of key Intermediates I to III. Representative methodology for Method A is described in Tao X. et al. J. Org. Chem. 2012, 77, pp 612-616, Method B in Azzouz, R. Synlett, 2006, 12, pp 1908-1912 and Method C in Deane K. J. et al., ACS Med. Chem. Lett., 2014, 5, pp 576-581 and Shi J. et al, ACS Omega, 2017, 2, 3406-3416. The general transformations Methods D and G are well known and have been described generally in references such as Protective Groups in Organic Synthesis, Green T. W. and Wuts P. G. M. John Wiley & Sons, New York, 1999 and Comprehensive Organic Transformations: A Guide to Functional Group Preparations, Larock, R. C. John Wiley & Sons, New York, 2018. Method E has been adapted from that described in Muller-Janssen, D. et al. Angew. Chem. Int. Ed. 2017, 56, pp 6276-6279. Starting materials may be commercially available or prepared by known methods.

Scheme 1

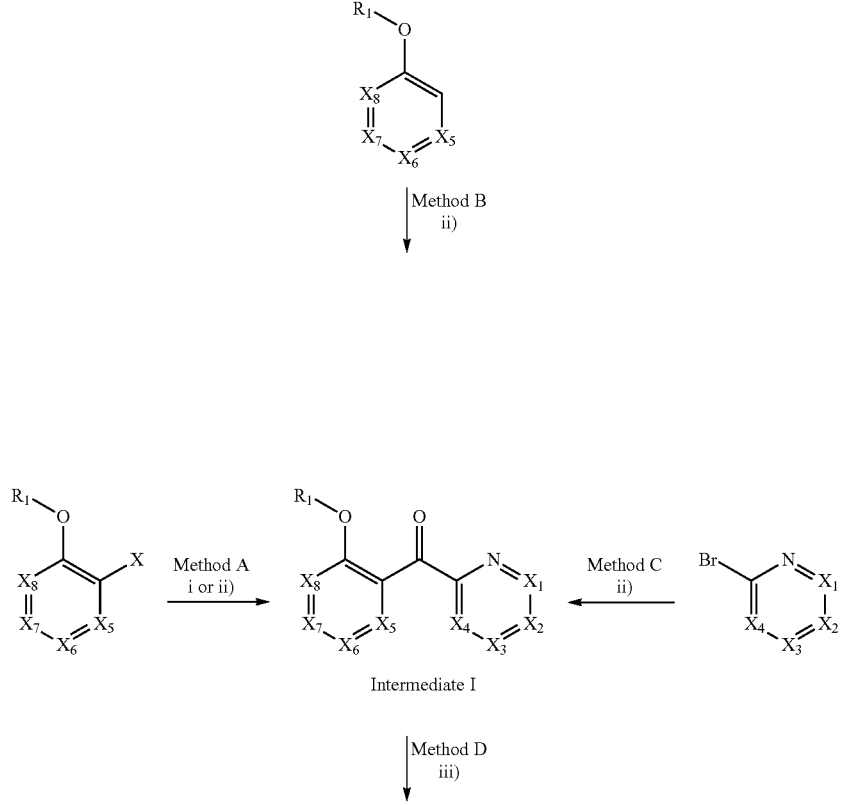

-continued

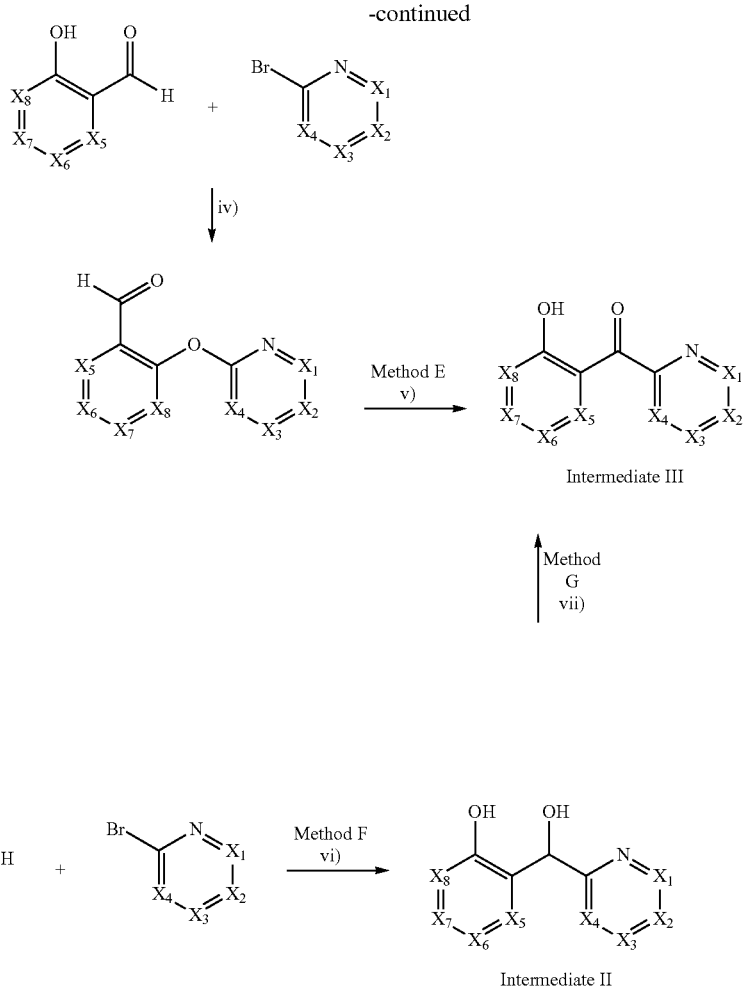

i) Mg, 0° C.-reflux, 0° C. nitrile, ester or amide; ii) BuLi, -100 to -78° C., nitrile, ester or amide; iii) BBr$_3$ or HX or TFA; iv) K$_3$PO$_4$, Pd(OAc)$_2$, CuI, picolinic acid; v) K$_3$PO$_4$, 2-4-dimethyl-1,2,4-triazolium iodide; vi) MgCl$_2$, N-methylmorpholine; vii) SeO$_2$.

These intermediates may then be formed into compounds of formula (I) as shown in Scheme 2 by methodology adapted from literature, for example, Wu, J. et al. Chem. Commun. 2010, 46, pp 3687-3689.

Scheme 2

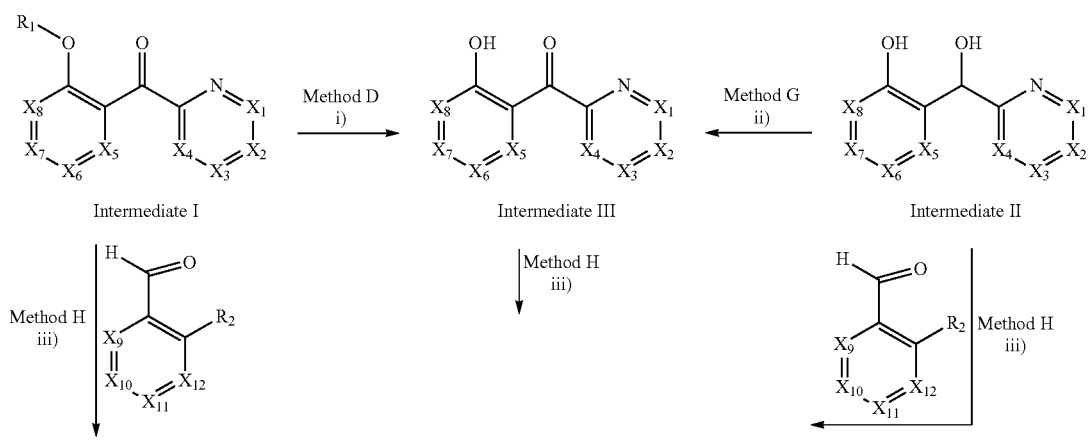

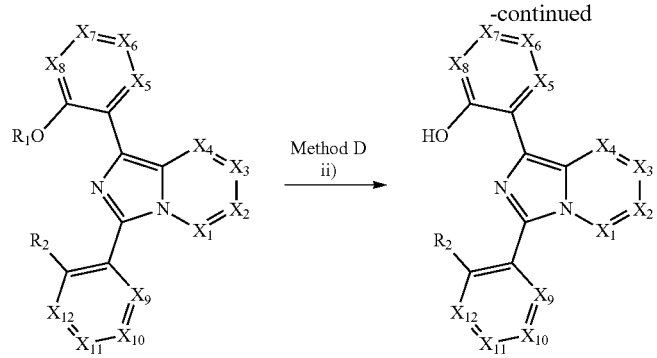

Formula IB → Formula IA i) HBr or BBr$_3$, ii) SeO$_2$, iii) NH$_4$OAc, aldehyde.

Methods of the Invention

For the treatment of metal-associated neurological disorders such as Parkinson's disease, it is highly desirable to find iron modulators. It has now been found in accordance with the present invention that certain iron modulators are capable of removing iron from cells, thus making them suitable candidates for treatment of Parkinson's disease and other metal ion associated neurological disorders.

In one aspect of the invention there is provided a method of treating or preventing a metal ion associated disorder comprising administering to a subject a compound of formula (I) or a pharmaceutically acceptable salt or solvate thereof. In some embodiments, the metal ion associated disorder is an iron ion associated disorder. In a particular embodiment, the metal ion associated disorder or iron ion associated disorder is a neurological disorder.

In a further aspect of the invention, there is provided a compound of formula (I) or a pharmaceutically acceptable salt or solvate thereof for use in treating or preventing a metal ion associated neurological disorder. In some embodiments, the metal ion associated disorder is an iron ion associated disorder. In a particular embodiment, the metal ion associated disorder or iron ion associated disorder is a neurological disorder.

In yet a further aspect of the invention, there is provided a use of a compound of formula (I) or a pharmaceutically acceptable salt or solvate thereof in the manufacture of a medicament for treating or preventing a metal ion associated disorder. In some embodiments, the metal ion associated disorder is an iron ion associated disorder. In a particular embodiment, the metal ion associated disorder or iron ion associated disorder is a neurological disorder.

Excess iron in vital organs increases the risk of many diseases, liver disease (cancer, cirrhosis), heart attack or heart failure, cardiotoxicity, diabetes mellitus, osteoarthritis, osteoporosis, metabolic syndrome, hypothyroidism, hypogonadism and is associated with onset of or acceleration of neurodegenerative diseases such as Alzheimer's disease, Parkinson's disease, Huntington's disease, epilepsy and multiple sclerosis.

In particular embodiment, the metal associated neurological disease is Parkinson's disease, Alzheimers disease, Huntington's disease, amylotrophic lateral sclerosis (ALS), fronto temporal dementia (FTD), multiple system atrophy (MSA), tardive dyskinesia (TD), Hallervorden-Spatz syndrome, Friedreichs ataxia, epilepsy and multiple sclerosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include amelioration or alleviation of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body. Other therapies may include: a MAO-B inhibitor such as selegiline, rasagiline, lazabemide, and caroxazone; a dopamine agonist such as bromocriptine, cabergoline, lisuride, pergolide; levodopa; carbidopa; inirole; apomorphine, sumanirole; rotigotine; talipexole; dihydroergocriptine or; a catechol-O-methyltransferase inhibitor such as tolcapone or entacapone. Further therapies may also include those administered for ALS, such as Riluzole or Edaravone.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt or solvate thereof and at least one pharmaceutically acceptable carrier.

The carrier(s) and/or excipients must be "acceptable" in the sense of being compatible with the other ingredients of the composition and not deleterious to the recipient thereof.

Pharmaceutical formulations include those suitable for oral, rectal, nasal, topical (including buccal and sub-lingual) or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to 1000 milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "composition" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a Hydrofluoroalkane (HFA) or chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler In formulations intended for administration to the respiratory tract, including intranasal formulations, the compound will generally have a small particle size for example of the order of 1 to 50 microns or less. Such a particle size may be obtained by means known in the art, for example by micronization.

When desired, formulations adapted to give sustained release of the active ingredient may be employed.

The pharmaceutical compositions are preferably in unit dosage forms. In such form, the composition is subdivided into unit doses containing appropriate quantities of the active component. The unit dosage form can be a packaged composition, the package containing discrete quantities of composition, such as packeted tablets, capsules, and powders in vials or ampoules. Also, the unit dosage form can be a capsule, tablet, cachet, or lozenge itself, or it can be the appropriate number of any of these in packaged form.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations

| ACN | acetonitrile | i-PrOH | isopropanol |
|---|---|---|---|
| AcOH | Acetic acid | KOAc | Potassium acetate |
| Bn | benzyl | MeOH | methanol |
| Conc. | concentrated | min | minute |
| CV | Column volume | ms | Mass spectrometry |
| DCM | dichloromethane | n-BuLi | n-butyl lithium |
| DMSO | dimethylsulfoxide | O/N | overnight |
| eq | equivalent | RBF | Round bottom flask |
| $Et_2O$ | diethylether | RT | Room temperature |
| EtOAc | ethyl acetate | sat | saturated |
| h | Hour/s | TFA | Trifluoroacetic acid |
| HBSS | Hanks' balanced salt solution | THF | tetrahydrofuran |
| HPLC | High performance liquid chromatography | $t_R$ | Retention time |

HPLC

HPLC were carried out using Column: Alltech Hypersil BD S C18 5 μm, 4.6 mm×150 mm using water/ACN eluents with both containing 0.1% TFA. Two gradient methods were employed specified as HPLC1 or HPLC2 and detailed in the protocols below.

| Time | 0.1% TFA in $H_2O$ | 0.1% TFA in ACN | Flow (mL/min) |
|---|---|---|---|
| HPLC1 gradient protocol ||||
| 0 | 95 | 5 | 1.0 |
| 0.5 | 95 | 5 | 1.0 |
| 6.5 | 0 | 100 | 1.0 |
| 7.5 | 0 | 100 | 1.0 |
| 8.0 | 95 | 5 | 1.0 |
| 12 | 95 | 5 | 1.0 |
| HPLC2 gradient protocol ||||
| 0 | 100 | 0 | 1.0 |
| 20 | 0 | 100 | 1.0 |
| 21 | 0 | 100 | 1.0 |
| 21.1 | 100 | 0 | 1.0 |
| 25 | 100 | 0 | 1.0 |

The following generalised methods were used to prepare compounds of Intermediates I to III as referred to in Schemes 1 and 2.

Method A (Scheme 1)

i) Grignard:

Magnesium (1.1 eq) was placed into a RBF and just covered with THF before a crystal of iodine was added followed by a small portion of the neat bromoanisole. The mixture was alternatively sonicated and heated until the Grignard formation initiated. Once initiated, the remaining bromoanisole in THF was added and the resultant mixture heated to reflux for 0.5 h. The Grignard solution was cooled to 0° C. before the appropriate nitrile, ester or amide (0.9 eq) in THF was added dropwise before quenching either after 1-2 h or after storing at 4° C. overnight. The reaction was quenched with sat. $NH_4Cl_{(aq)}$ and extracted with DCM. The combined organic extracts were dried and concentrated under reduced pressure to afford the crude ketone. Where a nitrile was used, the isolated imine intermediate was suspended/dissolved in ether and conc. HCl (3:1). The mixture was stirred for 0.5 h then neutralised using 2M $NaOH_{(aq)}$ before extraction with EtOAc. The combined organic extracts were dried ($Na_2SO_4$) and concentrated under reduced pressure to afford the crude ketone. The crude ketone was used as is or purified by crystallisation or flash chromatography.

ii) Organolithium:

Aryl iodide (1-2 eq) in $Et_2O$ or THF was cooled to ~−70° C. before 1M n-BuLi in hexanes was slowly added to the mixture keeping the temperature below −65° C. The resultant solution was stirred for 15 min before the nitrile, ester or amide (1-2 eq) in $Et_2O$ or THF was added. The reaction was either kept cool or, in the case of nitriles, allowed to warm to −10° C. over 2 h before quenching with sat. $NH_4Cl_{(aq)}$ and extraction with DCM. The combined extracts were dried and the solvent evaporated to yield the crude ketone (Intermediate I). Where a nitrile was used the imine was treated as described in i) to yield the crude ketone. The crude ketone was used as is or was purified by crystallisation or flash chromatography.

Method B (Scheme 1)

3-(Ethoxymethoxy)pyridine (1 eq) was dissolved in THF and cooled to −78° C. before n-BuLi in hexanes (1 eq) was added keeping the temperature at or below −78° C. The reaction was stirred for 0.5 h then the ester or amide (1 eq) dissolved in THF was added keeping temperature at or below −70° C. Whilst keeping cold the reaction was stirred for 1.5 h after which time it was quenched with i-PrOH followed by sat. $NH_4Cl_{(aq)}$. The reaction was allowed to warm to RT before being extracted with EtOAc (3×), dried and the solvent evaporated to yield the crude ketone (Intermediate I). The crude ketone was used as is or was purified by crystallisation or flash chromatography.

Method C (Scheme 1)

These methods are based on those described in the literature as represented by Deane K. J. et al., ACS Med. Chem. Lett., 2014, 5, pp 576-581 and Shi J. et al, ACS Omega, 2017, 2, pp 3406-3416.

i) n-BuLi in hexanes (1.17 eq) was added to a solution of 2-bromopyridine (1.0 eq) in THF and ether (1:1) at −110° C. The reaction was warmed to −10° C. over 0.5 h. The flask was again cooled to −110° C. and a solution/suspension of the ester (1.0 eq) in toluene (1.3 mL/mmol) was added. The reaction was stirred at room temperature for 17 h, after which it was quenched with sat. $NH_4Cl_{(aq)}$, followed by water. The mixture was extracted with EtOAc (3×) and the combined layers were washed with water, brine and then dried ($Na_2SO_4$). After concentration under reduced pressure the crude product was adsorbed onto $SiO_2$ and purified by flash chromatography.

ii) 2-Bromopyridine (1.0 eq) in THF (5.5 mL/mmol) was added dropwise to a solution of n-BuLi in hexane (1.0 eq) over 1 h at −78° C. The reaction was stirred at −78° C. for a further 1 h before a concentrated solution of the ester (1.0 eq) in THF was added and the reaction slowly allowed to warm to −20° C. then being maintained at this temperature for 2 h or until MS showed no sign of starting material. When complete, the reaction was quenched with a 10% $HCl_{(aq)}$ and the pH adjusted to pH6 using a 2M $HCl_{(aq)}$. The mixture was extracted with DCM (3×), dried and concentrated under reduced pressure to yield the crude ketone. The crude ketone (Intermediate I) was used as is or was purified by crystallisation or flash chromatography.

Method D (Scheme 1 or Scheme 2)

Standard techniques as described in Protective Groups in Organic Synthesis, Green, T. W. and Wuts P. G. M. John Wiley & Sons, New York, 1999 were employed to convert Intermediate I to Intermediate III or Formula IB or IA. In general, HBr or $BBr_3$ were employed to remove methyl and benzyl ether whilst either HCl or TFA was used to remove acetals.

i) Ether was suspended in 48% $HBr_{(aq)}$ and heated at 110-130° C. for 0.5-5 d. The reaction was cooled then concentrated under reduced pressure to afford a solid. The solid was treated with a sat. $NaHCO_{3(aq)}$ and extracted with EtOAc (3×). The combined organic extracts were washed with brine, dried and concentrated under reduced pressure to afford the crude product. Alternatively, the reaction may be diluted with water and neutralised with conc. $NH_{3(aq)}$ (re-buffering with AcOH if required) before being extracted with EtOAc. If required, samples were further purified by flash chromatography or crystallisation.

ii) Ether was dissolved in DCM and cooled to 0° C. before boron tribromide (6-12.0 eq) was added dropwise and the reaction warmed to room temperature. The mixture was stirred at for 17-48 h before MeOH was added and the solvent evaporated. MeOH was again added and the solvent evaporated (2×) before the residue was dissolved in EtOAc and washed with water (1×). The organic extract was dried and concentrated under reduced pressure to yield the crude product. Further purification may be achieved by trituration, crystallisation or chromatography.

Method E (Scheme 1)

2-(Pyridin-2-yloxy)benzaldehyde (1 eq), 2,4-dimethyl-1,2,4-triazolium iodide (0.2 eq) and $K_3PO_4$ (1 eq) were placed under Argon before adding THF. The reaction was heated to reflux under Argon and stirred for 18 h after which time the reaction was cooled, $SiO_2$ added and the solvent evaporated to yield Intermediate III adsorbed on the $SiO_2$. The sample was dry loaded onto a $SiO_2$ column and purified by flash chromatography.

Method F (Scheme 1)

Adaption of method described by Gale E. M., et al, JACS, 2016, 138 (49), 15861-15864 and Whiting M., et al, Synlett, 2009, 10, 1609-1613.

A substituted phenol (2 eq) and N-methylmorpholine (1 eq) were stirred in DCM (0.5 mL/mmol). Magnesium chloride (3.5 eq) was added to the reaction followed by the dropwise addition of 2-pyridinecarboxaldehyde (1.0 eq) dissolved in DCM (0.3 mL/mmol). The aldehyde was added over 3 h and the reaction was stirred at room temperature for between 48-120 h. Water was added to the reaction (1 mL/mmol) and the pH adjusted to pH1 using conc. $HCl_{(aq)}$. The pH was then adjusted to pH9 using sat. $Na_2CO_{3(aq)}$. The organic layer was removed and the aqueous phase was extracted with DCM (2×). The combined organic extracts were dried ($Na_2SO_4$) and concentrated under reduced pressure to afford the crude alcohol (Intermediate II) which was adsorbed on $SiO_2$, dry loaded onto a $SiO_2$ column and purified by flash chromatography.

Method G (Scheme 1 and Scheme 2)

Standard techniques as described in Comprehensive Organic Transformations: A Guide to Functional Group Preparations, Larock, R. C. John Wiley & Sons, New York, 2018 were employed to convert Intermediate II to Intermediate III if required. In general, mild oxidants such as $SeO_2$ were used.

Synthesis of Condensation Precursors (2-Methoxyphenyl)(pyridine-2-yl)methanone (H)

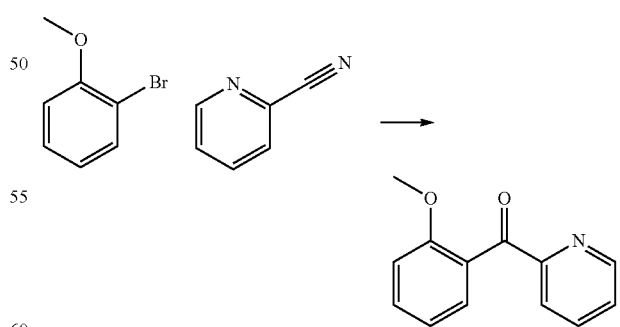

This compound was prepared from 2-bromoanisole (6.0 g, 32 mmol), 2-pyridylcarbonitrile (3.0 g) and magnesium (0.86 g) following the Method Ai). The title compound was isolated as pale yellow crystals (1.76 g, 26%). $^1$H NMR ($d_6$-DMSO, 600 MHz) δ 8.63 (1H, d, J 3.6 Hz), 7.97 (1H, d, J 7.8 Hz), 7.84 (1H, t, J 7.8 Hz), 7.52 (1H, d, J 7.2 Hz), 7.47

(1H, d, J 7.8 Hz), 7.41 (1H, t, J 4.8 Hz), 7.04 (1H, t, J 7.2 Hz), 7.96 (1H, d, J 8.4 Hz), 3.64 (3H, s).

(3-Methoxypyridin-2-yl)(pyridin-2-yl)methanone
(L)

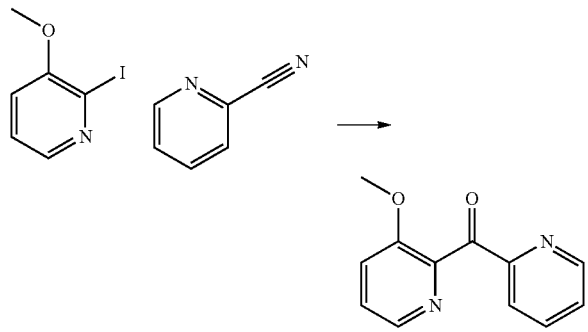

The title compound was prepared using 2-iodo-3-methoxypyridine (500 mg), picolinonitrile (390 mg) with Et$_2$O as the solvent and 1M n-BuLi in hexanes (3.8 mL) using Method A ii). The crude product was purified on 12 g SiO$_2$ using MeOH/DCM gradient 0-0% 3 CV, 0-10% 20 CV. The product fractions were combined and evaporated to yield the title compound as an oil (244 mg) which was used without further manipulation. $^1$H NMR (CDCl$_3$, 600 MHz) δ 8.28 (1H, ddd, J 4.8, 1.8, 0.9 Hz), 8.28 (1H, dd, J 4.6, 1.4 Hz), 8.13 (1H, dt, J 7.9, 1.1 Hz), 7.86 (1H, dt, J 7.9, 1.5 Hz), 7.43 (1H, ddd, J 7.6, 4.8, 1.3 Hz), 7.38 (1H, dd, J 8.5, 4.7 Hz), 7.33 (1H, dd, J 8.5, 1.3 Hz), 3.77 (3H, s).

(3-Hydroxypyridin-4-yl)(pyridazin-3-yl)methanone
(C)

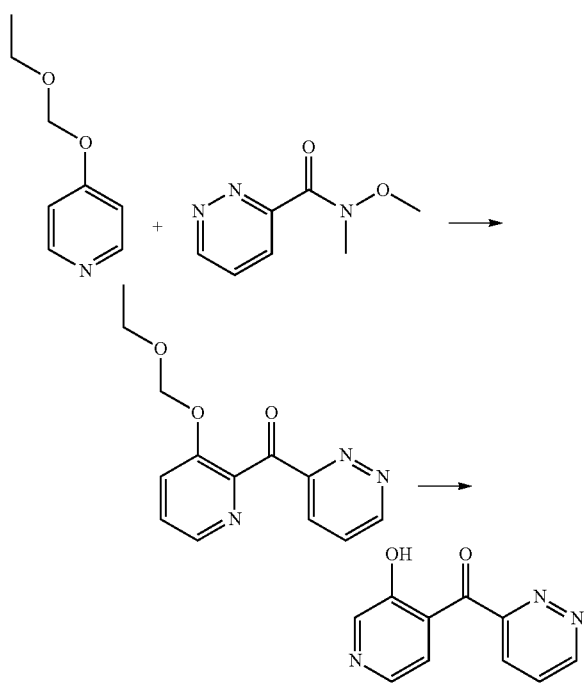

Synthesis of (3-(ethoxymethoxy)pyridin-2-yl)(pyridazin-3-yl)methanone

The title compound was prepared using 3-(ethoxymethoxy)pyridine (180 mg), N-methoxy-N-methyl pyridazine-3-carboxamide (196 mg) and 2.37M n-BuLi in hexanes (495 μL) using Method B. The crude product was purified by flash chromatography using 12 g SiO$_2$ and a MeOH/DCM gradient 0-0% 3 CV, 0-10% 30 CV. The product fractions were combined and evaporated to yield the title compound (162 mg) contaminated with amide SM (2:1). The sample was used without further manipulation. $^1$H NMR (CDCl$_3$, 600 MHz) δ 9.33 (1H, dd, J 5.1, 1.9 Hz), 8.70 (1H, s), 8.47 (1H, d, J 4.9 Hz), 8.20 (1H, dd, J 8.5, 1.8 Hz), 7.72 (1H, dd, J 8.5, 5.1 Hz), 7.43 (1H, d, J 4.7 Hz), 5.09 (2H, s), 3.52 (2H, q, J 7.1 Hz), 1.14 (3H, t, J 7.1 Hz).

Synthesis of (3-hydroxypyridin-4-yl)(pyridazin-3-yl)methanone (3-(Ethoxymethoxy)pyridin-2-yl)(pyridazin-3-yl)methanone (~2:1 (ketone:amide), 162 mg) was dissolved in MeOH (2 mL) and treated with TFA (500 μL) before heating at 60° C. for 1.5 h after which time the reaction was diluted with MeOH and the solvent evaporated. The residue was treated with aqueous MeOH and again evaporated before being evaporated from toluene to yield the crude product. The sample was purified on 12 g SiO$_2$ using MeOH/DCM gradient 0-0% 3 CV, 0-10% 40 CV and the product fractions combined and evaporated to yield the title compound as an oil (91 mg). 1H NMR (CDCl$_3$, 600 MHz) δ 11.75 (1H, bs), 9.42 (1H, dd, J 5.0, 1.7 Hz), 8.72 (1H, s), 8.28 (1H, dd, J 8.5, 1.7 Hz), 8.26 (1H, d, J 5.6 Hz), 8.15 (1H, d, J 5.5 Hz), 7.85 (1H, dd, J 8.5, 5.1 Hz).

(3-Methoxypyridin-4-yl)(pyridin-2-yl)methanone
(B)

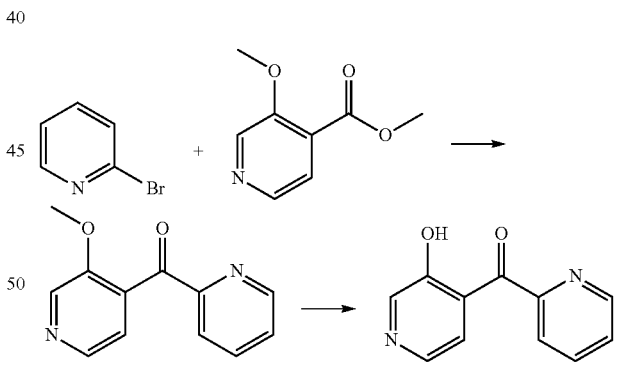

Synthesis of (3-methoxypyridin-4-yl)(pyridin-2-yl)methanone

The ketone was formed according to the general Method C i) using 2-bromopyridine (560 mg) in THF (4 mL) and ether (4 mL) followed by 2.28M $_n$-BuLi in hexane (1.8 mL) then methyl 3-methoxyisonicotinate (590 mg). The brown gum was dry loaded onto silica and run through a 12 g SiO$_2$ column eluting with EtOAc/hexane gradient 0-100%, 50 CV. The desired product eluted from the column last to afford a pale yellow solid (0.30 g, 42%). $^1$H NMR (CDCl$_3$, 600 MHz) δ8.63 (1H, dd, J 4.8, 0.6 Hz), 8.43 (1H, s), 8.39

(1H, d, J 4.8 Hz), 8.09 (1H, d, J 7.8 Hz), 7.89 (1H, td, J 7.8, 1.2 Hz), 7.47 (1H, dd, J 7.8, 4.8 Hz), 7.31 (1H, d, J 4.8 Hz), 3.79 (3H, s).

(3-Hydroxypyridin-4-yl)(pyridin-2-yl)methanone (3-Methoxypyridin-4-yl)(pyridin-2-yl)methanone (300 mg) was treated with conc. HBr$_{(aq)}$ (4 mL) and heated at 120° C. for 48 h. The reaction was cooled then concentrated under reduced pressure to afford a solid. The solid was treated with a sat. NaHCO$_{3(aq)}$ (10 mL) and extracted with EtOAc (3×). The combined organic extracts were washed with brine, dried (Na$_2$SO$_4$) and concentrated under reduced pressure to afford the title compound as yellow solid (0.24 g, 86%). $^1$H NMR (d$_6$-DMSO, 600 MHz) δ 8.64 (1H, d, J 4.8 Hz), 8.32 (1H, d, J 6.6 Hz), 8.32 (1H, d, J 4.8 Hz), 8.08 (1H, d, J 6.6 Hz), 8.08 (1H, d, J 7.8 Hz), 7.70 (1H, d, J 4.8 Hz), 7.00 (1H, s).

(2-Methoxypyridin-3-yl)(pyridin-2-yl)methanone (J)

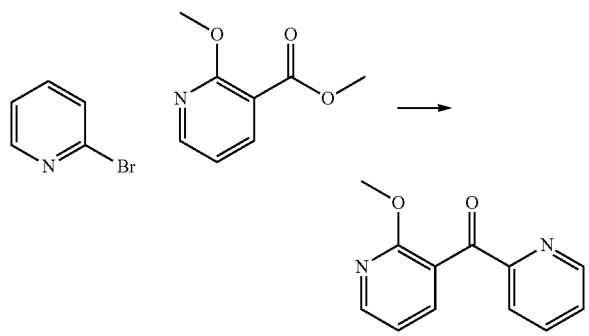

The ketone was formed using Method C ii) using 2-bromopyridine (1.86 g) in THF (50 mL) and a 2.37M n-BuLi solution in hexane (5.0 mL) then methyl 2-methoxynicotinate (1.8 g) in THF (3 mL). The green solid was used without further purification (1.86 g, 74%). $^1$H NMR (CDCl$_3$, 600 MHz) δ 8.62 (1H, dq, J 1.2, 5.4 Hz), 8.31 (1H, dd, J 1.8, 4.8 Hz), 8.01 (1H, td, J 7.8, 1.2 Hz), 7.86 (2H, dd, J 7.2, 1.8 Hz), 7.44 (1H, ddd, J 7.2, 4.2, 1.2 Hz), 6.99 (1H, dd, J 7.2, 5.4 Hz), 3.81 (3H, s).

(2-Hydroxyphenyl)(pyridin-2-yl)methanone (A)

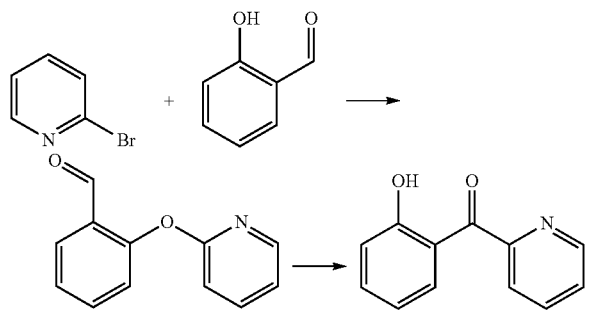

An adaption of the methods described by Janssen-Muller, D. et al. Angwe. Chem. Int. Ed. 2017, 56, pp 6276-6279.

Synthesis of 2-(pyridin-2-yloxy)benzaldehyde

Ground potassium phosphate (4.25 g), CuI (95 mg) and picolinic acid (123 mg) were suspended in DMSO (25 mL) before salicylaldehyde (1.27 mL) followed by 2-bromopyridine (954 μL) were added. The initial bright yellow mixture rapidly turned to a brown colour on stirring, then after 10 mins heating became green. The reaction was placed under Ar and heated to 80° C. for 70 h after which time the reaction was cooled and poured into water before extraction with EtOAc (4×). The combined extracts were dried and the solvent evaporated to yield the crude product which was purified on 40 g SiO$_2$ using an EtOAc/hexanes gradient 0-0% 3 CV, 0-20% 20 CV. The target fractions were collected and combined to yield the title compound (366 mg). $^1$H NMR (CDCl$_3$, 600 MHz) δ 10.31 (1H, s), 8.17 (1H, dd, J 5.5, 2.0 Hz), 7.97 (1H, dd, J 7.7, 1.7 Hz), 7.78-7.74 (1H, m), 7.65-7.60 (1H, m), 7.33 (1H, t, J 7.6 Hz), 7.17 (1H, d, J 8.2 Hz), 7.07-7.03 (2H, m).

Synthesis of (2-hydroxyphenyl)(pyridin-2-yl)methanone (A)

Method E was employed using 2-(pyridine-2-yloxy)benzaldehyde (800 mg), 2,4-dimethyl-1,2,4-triazolium iodide (181 mg) and K$_3$PO$_4$ (341 mg). The sample was purified on 12 g SiO$_2$ using an EtOAc/hexanes gradient 0-0% 3 CV, 0-25% 20 CV. The target fractions were combined and evaporated to yield the title compound (614 mg). $^1$H NMR (CDCl$_3$, 600 MHz) δ 12.36 (1H, bs), 8.74 (1H, d, J 4.8 Hz), 8.12 (1H, dd, J 8.2, 1.8 Hz), 7.95-7.91 (2H, m), 7.53-7.49 (2H, m), 7.06 (1H, dd, J 8.5, 1.0 Hz), 6.90 (1H, ddd, J 8.1, 7.0, 1 Hz)

2-Fluoro-6-(hydroxy(pyridin-2-yl)methyl)phenol (N)

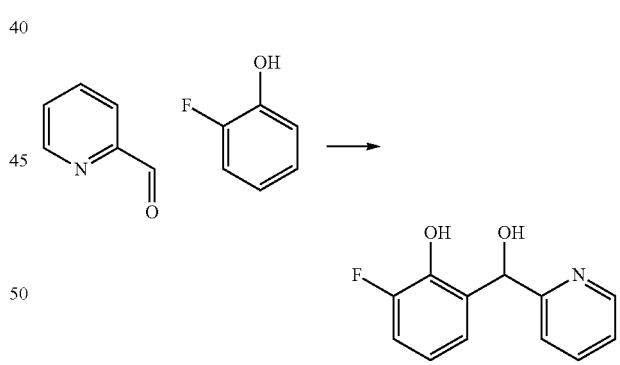

2-Fluorophenol (5.2 g) and magnesium chloride (7.1 g) were stirred in DCM. N-Methylmorpholine (4.2 g) was added to this solution to maintain a temperature below 30° C. 2-Pyridinecarboxaldehyde (3.0 g) in DCM (15 mL) was then added over 3 h and the rest of the reaction was conducted according to Method F to afford a green oil. Purification on silica (80 g) using an EtOAc/hexanes gradient 0-50% 10 CV, 50-80% 10 CV afforded the title compound as a pale yellow solid (0.22 g, 5%). $^1$H NMR (CDCl$_3$, 600 MHz) δ 8.52 (1H, dd, J 6.0, 0.6 Hz), 7.78 (1H, td, J 9.6, 2.4 Hz), 7.53 (1H, d, J 9.0 Hz), 7.28 (1H, dd, J 7.2, 6.0 Hz), 7.14 (1H, d, J 9.0 Hz), 7.03 (1H, td, J 9.6, 1.8 Hz), 6.82 (1H, td J 9.6, 5.4 Hz), 6.07 (1H, bs), OHs not seen.

(2-Hydroxy-4-(trifluoromethyl)phenyl)(pyridin-2-yl)methanone (R)

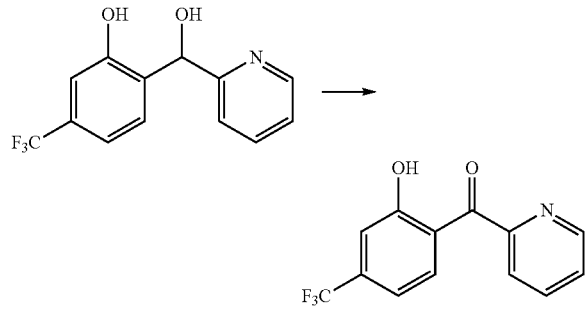

2-(Hydroxy(pyridine-2-yl)methyl)-5-(trifluoromethyl)phenol (220 mg) was heated in 1,4,-dioxane (5 mL) with selenium dioxide (50 mg) for 4 h after which time the reaction was filtered through a small pad of Celite®, eluting with EtOAc and concentrated to afford the crude product. This was purified on 12 g $SiO_2$ using an EtOAc/hexanes gradient 0-50% over 30 CV to yield the title compound as a yellow solid (190 mg, 87%). $^1$H NMR ($CDCl_3$, 500 MHz) δ 12.82 (1H, s), 8.75 (1H, ddd, J 5.0, 1.5, 1.9 Hz), 8.35 (1H, dd, J 8.0, 0.5 Hz), 8.09 (1H, dd, J 8.0, 1.0 Hz), 8.00 (1H, td, J 7.5, 1.5 Hz), 7.60 (1H, ddd, J 8.0, 5.0, 1.5 Hz), 7.33 (1H, dd, J 1.0, 0.5 Hz), 7.15 (1H, ddd, J 8.0, 1.5, 0.5 Hz).

The general methodology described above was used to prepare the compounds depicted in Table 1 employing the method indicated and using the appropriate starting materials.

TABLE T1

Intermediates I, II and IKII.

| ID | Intermediate | Mthd | NMR Data |
|---|---|---|---|
| A | | A, D or E | $^1$H NMR ($CDCl_3$, 600 MHz) δ 12.36 (1H, bs), 8.74 (1H, d, J 4.8 Hz), 8.12 (1H, dd, J 8.2, 1.8 Hz), 7.95-7.91 (2H, m), 7.53-7.49 (2H, m), 7.06 (1H, dd, J 8.5, 1.0 Hz), 6.90 (1H, ddd, J 8.1, 7.0, 1 Hz) |
| B | | C, D | $^1$H NMR ($d_6$-DMSO, 600 MHz) δ 8.64 (1H, d, J 4.8 Hz), 8.32 (1H, d, J 6.6 Hz), 8.32 (1H, d, J 4.8 Hz), 8.08 (1H, d, J 6.6 Hz), 8.08 (1H, d, J 7.8 Hz), 7.70 (1H, d, J 4.8 Hz), 7.00 (1H, s), OH not observed. |
| C | | AD | $^1$H NMR ($CDCl_3$, 600 MHz) δ 11.95 (1H, bs), 9.34 (1H, d, J 4.4 Hz), 8.21 (1H, d, J 8.0 Hz), 8.03 (1H, d, J 8.3 Hz), 7.72 (1H, dd, J 8.1, 5.0 Hz), 7.53 (1H, t, J 8.0 Hz), 7.05 (1H, d, J 8.4 Hz), 6.91 (1H, t, J 7.7 Hz) |
| D | | A, D | $^1$H NMR ($CDCl_3$, 500 MHz) δ 11.9 (1H, bs), 8.95 (2H, d, J 5.3 Hz), 7.73 (1H, dd, J 9.7, 1.8 Hz), 7.54 (1H, ddd, J 8.2, 7.1, 1.8 Hz), 7.50 (1H, t, J 5.3 Hz), 7.08 (1H, dd, J 8.8, 1.2 Hz), 6.88 (1H, ddd, J 8.2, 7.6, 1.8 Hz). |
| F | | B,D | $^1$H NMR ($CDCl_3$, 600 MHz) δ 11.75 (1H, bs), 9.42 (1H, dd, J 5.0, 1.7 Hz), 8.72 (1H, s), 8.28 (1H, dd, J 8.5, 1.7 Hz), 8.26 (1H, d, J 5.6 Hz), 8.15 (1H, d, J 5.5 Hz), 7.85 (1H, dd, J 8.5, 5.1 Hz). |
| G | | B, D | $^1$H NMR ($CDCl_3$, 600 MHz) δ 11.8 (1H, bs), 8.99 (2H, d, J 4.8 Hz), 8.78 (1H, bs), 8.25 (1H, d, J 5.3 Hz), 7.97 (1H, bd, J 4.5 Hz), 7.58 (1H, t, J 4.9 Hz). |
| H | | A | $^1$H NMR ($CDCl_3$, 600 MHz) δ 8.65 (1H, bd, 4.7 Hz), 7.99 (1H, d, J 7.8 Hz), 7.86 (1H, dt, J 7.7, 1.8 Hz), 7.54 (1H, dd, J 7.5, 1.7 Hz), 7.49 (1H, ddd, J 8.5, 7.5, 1.8 Hz), 7.43 (1H, ddd, J 7.5, 4.7, 1.3 Hz), 7.06 (1H, dt, J 7.5, 0.8 Hz), 6.98 (1H, d, J 8.4 Hz), 3.65 (3H, s). |

TABLE T1-continued

Intermediates I, II and IK/II.

| ID | Intermediate | Mthd | NMR Data |
|---|---|---|---|
| I | (pyridin-2-yl)(2-hydroxy-5-methylphenyl)methanol | F | ¹H NMR (CDCl₃, 600 MHz) δ 8.47 (1H, d, J 4.2 Hz), 7.10 (1H, t, J 7.2 Hz), 7.43 (1H, d, J 7.8 Hz), 7.21 (1H, t, J 5.4 Hz), 7.10 (1H, s), 6.98 (1H, d, J 8.4 Hz), 6.83 (1H, d, J 8.4 Hz), 5.91 (1H, s), 2.25 (3H, s), OHs not seen. |
| J | pyridin-2-yl(2-methoxypyridin-3-yl)methanone | C | ¹H NMR (CDCl₃, 600 MHz) δ 8.62 (1H, dq, J 5.4, 1.2 Hz), 8.31 (1H, dd, J 4.8, 1.8 Hz), 8.01 (1H, td, J 7.8, 1.2 Hz), 7.87-7.85 (2H, m), 7.44 (1H, ddd, J 7.2, 4.2, 1.2 Hz), 6.99 (1H, dd, J 7.2, 5.4 Hz), 3.81 (3H, s). |
| K | pyridin-2-yl(4-methoxypyridin-3-yl)methanone | C | ¹H NMR (CDCl₃, 600 MHz) δ 8.62 (1H, dq, J 4.8, 0.6 Hz), 8.61 (1H, s), 8.60 (1H, d, J 6.0 Hz), 8.05 (1H, td, J 7.8, 1.2 Hz), 7.87 (1H, td, J 7.8, 1.2 Hz), 7.45 (1H, ddd, J 7.8, 4.8, 1.2 Hz), 6.90 (1H, d, J 5.4 Hz), 3.75 (3H, s) |
| L | pyridin-2-yl(3-methoxypyridin-2-yl)methanone | A | ¹H NMR (CDCl₃, 600 MHz) δ 8.28 (1H, ddd, J 4.8, 1.8, 0.9 Hz), 8.28 (1H, dd, J 4.6, 1.4 Hz), 8.13 (1H, dt, J 7.9, 1.1 Hz), 7.86 (1H, dt, J 7.9, 1.5 Hz), 7.43 (1H, ddd, J 7.6, 4.8, 1.3 Hz), 7.38 (1H, dd, J 8.5, 4.7 Hz), 7.33 (1H, dd, J 8.5, 1.3 Hz), 3.77 (3H, s). |
| M | pyridazin-3-yl(3-methoxypyridin-2-yl)methanone | A, D | ¹H NMR (CDCl₃, 600 MHz) δ 9.30 (1H, dd, J 5.1, 1.8 Hz), 8.31 (1H, dd, J 4.6, 1.2 Hz), 8.22 (1H, dd, J 8.4, 1.7 Hz), 7.69 (1H, dd, J 8.4, 5.1 Hz), 7.44 (1H, dd, J 8.6, 4.5 Hz), 7.38 (1H, dd, J 8.3, 1.1 Hz), 3.78 (3H, s). |
| N | (pyridin-2-yl)(3-fluoro-2-hydroxyphenyl)methanol | F | ¹H NMR (CDCl₃, 600 MHz) δ 8.52 (1H, dd, J 6.0, 0.6 Hz), 7.78 (1H, td, J 9.6, 2.4 Hz), 7.53 (1H, d, J 9.0 Hz), 7.28 (1H, dd, J 7.2, 6.0 Hz), 7.14 (1H, d, J 9.0 Hz), 7.03 (1H, td, J 9.6, 1.8 Hz), 6.82 (1H, td J 9.6, 5.4 Hz), 6.07 (1H, bs), OHs not seen. |
| O | (pyridin-2-yl)(4-fluoro-2-hydroxyphenyl)methanol | F | ¹H NMR (CDCl₃, 600 MHz) δ 8.53 (1H, ddd, J 6.0, 2.4, 1.2 Hz), 7.79 (1H, td, J 9.6, 2.4 Hz), 7.46 (1H, dd, J 10.2, 1.8 Hz), 7.27-7.30 (2H, m), 6.67 (1H, dd, J 9.6, 2.4 Hz), 6.60 (1H, td J 10.2, 3.6 Hz), 5.95 (1H, s), OHs not seen. |
| Q | (5-(trifluoromethyl)pyridin-2-yl)(2-hydroxyphenyl)methanone | E | ¹H NMR (d₆-DMSO, 600 MHz) δ 10.46 (1H, bs), 9.05 (1H, s), 8.43 (1H, d J 7.8 Hz), 8.03 (1H, d, J 7.8 Hz), 7.57 (1H, d, J 7.8 Hz), 7.47 (1H, t, J 7.8 Hz), 6.92 (2H, m). |
| R | pyridin-2-yl(2-hydroxy-4-(trifluoromethyl)phenyl)methanone | F, G | ¹H NMR (CDCl₃, 500 MHz) δ 12.82 (1H, s), 8.75 (1H, ddd, J 5.0, 1.5, 1.0 Hz), 8.35 (1H, dd, J 8.0, 0.5 Hz), 8.09 (1H, dd, J 8.0, 1.0 Hz), 8.00 (1H, td, J 7.5, 1.5 Hz), 7.60 (1H, ddd, J 5.0, 8.0, 5.0, 1.5 Hz), 7.33 (1H, dd, J 1.0, 0.5 Hz), 7.15 (1H, ddd, J 8.0, 1.5, 0.5 Hz). |

TABLE T1-continued

Intermediates I, II and IKII.

| ID | Intermediate | Mthd | NMR Data |
|---|---|---|---|
| S | (structure: pyridine-C(O)-phenol-Br) | F, G | $^1$H NMR (CDCl$_3$, 600 MHz) δ 8.72 (1H, d, J 4.8 Hz), 8.15 (1H, dd, J 8.4, 1.8 Hz), 8.01 (1H, d, J 8.4 Hz), 7.96 (1H, td, J 7.2, 1.2 Hz), 7.77 (1H, dd, J 7.8, 1.2 Hz), 7.55 (1H, ddd, J 7.8, 4.8, 1.2 Hz), 6.18 (1H, t, J 7.8 Hz), OH not observed. |
| T | (structure: pyridine-CH(OH)-phenol with F and Br) | F | $^1$H NMR (CDCl$_3$, 600 MHz) δ 8.48 (1H, d, J 4.2 Hz), 7.80 (1H, td, J 7.8, 1.8 Hz), 7.53 (1H, d, J 6.6 Hz), 7.52 (1H, d, J 7.2 Hz), 7.29 (1H, ddd, J 6.0, 5.4, 1.2 Hz), 6.72 (1H, d, J 9.6), 5.95 (1H, s), OHs not seen. |
| U | (structure: pyridine-CH(OH)-phenol with Br and F) | F | $^1$H NMR (CDCl$_3$, 600 MHz) δ 8.53 (1H, d, J 4.8 Hz), 7.66 (1H, td, J 7.8, 1.8 Hz), 7.42 (1H, d, J 7.8 Hz), 7.21-7.24 (2H, m), 6.69 (1H, d, J 11.4 Hz), 6.00 (1H, s), OHs not seen. |

Synthesis of Compounds of Formula I.

The following generalised method was used to prepare compounds of formulae IA and IB.

Method H

This methodology is widely described in the literature and is exemplified by that described by Wu, J. Chem. Commun., 2010, 46, pp 3687-3689.

Intermediates I, II or III (1.0 eq), aldehyde (1.5-3 eq) and ammonium acetate (5-10 eq) were suspended in acetic acid in a sealed vial. The contents were heated at between 80-110° C. for 16-24 h then cooled. The reaction mixture was poured onto iced water and the product isolated either by filtration or extraction and the crude product further purified, if required, by trituration, crystallisation or flash chromatography.

2-((Dimethylamino)methyl)-6-(1-(2-hydroxyphenyl)imidazo[1,5-a]pyridin-3-yl)phenol (124)

The title compound was prepared employing the general Method H using (2-hydroxyphenyl)(pyridin-2-yl)methanone (50 mg) and 3-((dimethylamino)methyl)-2-hydroxybenzaldehyde (120 mg) along with ammonium acetate (800 mg) in acetic acid (2 mL). The reaction was heated at 110° C. for 17 h before pouring the reaction into ice water. The crude product was isolated by extraction with EtOAc and further purified by flash chromatography on 12 g SiO$_2$ using EtOAc as the eluent. The target fractions were combined and evaporated to yield a solid which was sonicated in ethanol, filtered, washed with ethanol and air dried to yield the title compound (37 mg) as a yellow solid. t$_R$ 7.52 min (99%, HPLC2); $^1$H NMR (CDCl$_3$, 600 MHz) δ 7.97 (1H, dt, J 9.6, 0.6 Hz), 7.84 (1H, dt, J 7.2, 1.2 Hz), 7.81 (1H, dd, J 7.8, 1.2 Hz), 7.56 (1H, dd, J 7.8, 1.8 Hz), 7.16 (1H, ddd, J 9.0, 7.2, 1.8 Hz), 7.13 (1H, dt, J 7.2, 1.2 Hz), 7.04 (1H, dd, J 8.4, 1.2 Hz), 6.94 (2H, td, J 7.8, 1.8 Hz), 6.87 (1H, ddd, J 9.0, 6.0, 0.6 Hz), 6.66 (1H, td, J 6.6, 1.2 Hz), 3.78 (2H, s), 2.37 (6H, s); m/z (MH$^+$) 360.17.

2-(3-(3,5-Difluoro-2-hydroxyphenyl)imidazo[1,5-a]pyridin-1-yl)pyridin-3-ol (84)

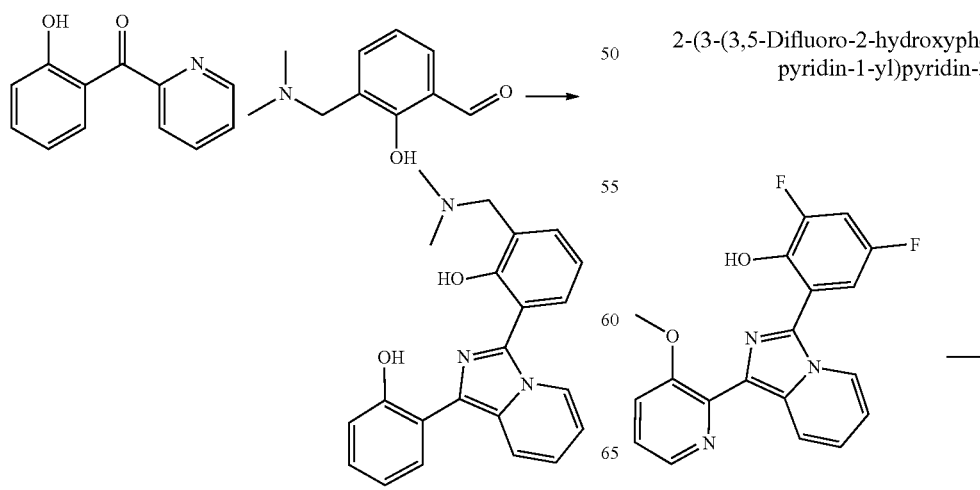

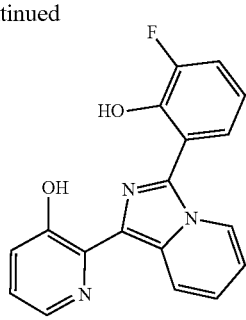

2,4-Difluoro-6-(1-(3-methoxypyridin-2-yl)imidazo[1,5-a]pyridin-3-yl)phenol (60 mg) was deprotected using the general Method Di) employing 48% HBr$_{(aq)}$ and heating at 120° C. for approximately 5 d. The product was isolated by extraction after neutralisation with NH$_{3(aq)}$ to yield a crude product. The crude product was purified by reverse phase flash chromatography on C18 SiO$_2$ using a 0.1% HCO$_2$H in ACN/water gradient 0-0% 3 CV, 0-50% 2 CV, 50-100% 20 CV. The desired fractions were combined and the resultant solid recrystallised from EtOH$_{(aq)}$ to yield the title compound as a light brown solid (5.9 mg). t$_R$ 5.42 min (>95%, HPLC1); $^1$H NMR (d$_6$-DMSO, 600 MHz) δ 12.17 (1H, s), 10.46 (1H, s), 8.69 (1H, d, J 9.3 Hz), 8.20 (1H, d, J 3.7 Hz), 8.04 (1H, d, J 7.1 Hz), 7.52 (1H, t, J 9.0 Hz), 7.33 (1H, s), 7.31 (1H, s), 7.25-7.15 (2H, m), 7.00 (1H, t, J 6.4 Hz); m/z (MH$^+$) 340.09.

4-(3-(3,5-Difluoro-2-hydroxyphenyl)imidazo[1,5-a]pyridin-1-yl)pyridin-3-ol (114)

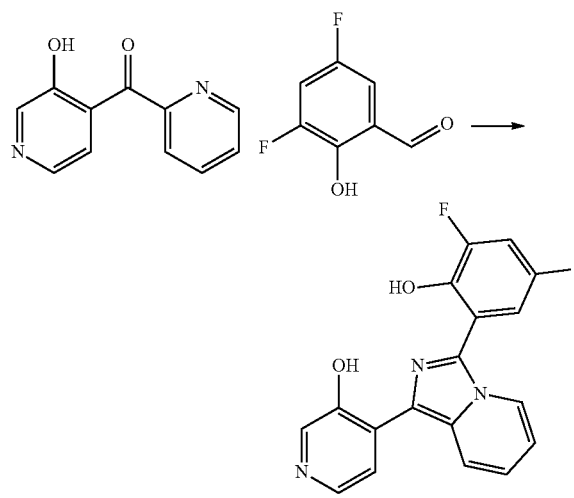

(3-Hydroxypyridin-4-yl)(pyridin-2-yl)methanone. (50 mg), 3,5-difluorosalicylaldehyde (110 mg) and ammonium acetate (90 mg) were suspended in acetic acid (2.5 mL) and reacted according to Method H at 110° C. and the crude product was recrystallised (ACN) to afford the title compound as a yellow solid (45 mg, 55%). t$_R$ 9.11 min (98%, HPLC2); (d$_6$-DMSO, 600 MHz) δ 11.70 (1H, bs), 8.25 (1H, s), 8.21 (1H, d, J 9.0 Hz), 8.09 (1H, d, J 5.4 Hz), 8.01 (1H, d, J 7.2 Hz), 7.82 (1H, d, J 4.8 Hz), 7.47 (1H, t, J 7.8 Hz), 7.27 (1H, d, J 8.4 Hz), 7.15 (1H, dd, J 9.6, 6.6 Hz), 6.92 (1H, t, J 6.6 Hz); m/z (MH$^+$) 340.09.

2-(3-(2-Hydroxyphenyl)imidazo[1,5-a]pyridin-1-yl)pyridin-3-ol (4)

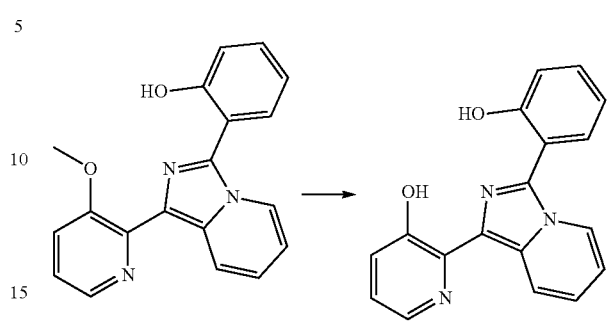

2-(1-(3-Methoxypyridin-2-yl)imidazo[1,5-a]pyridin-3-yl)phenol (118 mg) in DCM (10 mL) was cooled to 0° C. and BBr$_3$ (~210 μL) using the general Method Di). The residue was partitioned between sat. NaHCO$_{3(aq)}$ and EtOAc. The EtOAc layer was separated and the aqueous layer extracted further with EtOAc (2×). The combined extracts were dried and the solvent evaporated to yield the crude product. The sample was purified on 12 g SiO$_2$ using MeOH/DCM gradient 0-0% 3 CV, 0-10% 20 CV which only partially separated the target compound. The pure fractions were combined and evaporated to yield the title compound (49 mg) as a pale yellow solid. $^1$H NMR (d$_6$-DMSO, 600 MHz) δ 12.44 (1H, s), 10.34 (1H, s), 8.66 (1H, dtd, J 9.2, 1.3, 0.5 Hz), 8.19 (1H, ddd, J 3.1, 1.4, 0.5 Hz), 7.93 (1H, dtd, J 7.2, 1.1, 0.5 Hz), 7.55 (1H, ddd, J 7.6, 1.8, 0.4 Hz), 7.44 (1H, ddd, J 7.4, 1.7, 0.5 Hz), 7.30 (1H, ddd, J 8.1, 1.4, 0.5 Hz), 7.17-7.14 (2H, m), 7.11 (1H, dd, J 8.3, 1.2 Hz), 7.04 (1H, tdd, J 7.5, 1.2, 0.4 Hz), 6.05 (1H, ddd, J 6.5, 1.3, 0.5 Hz); m/z (MH$^+$) 304.11.

2-(3-(3-Fluoro-2-hydroxyphenyl)imidazo[1,5-a]pyridin-1-yl)pyridin-3-ol (81)

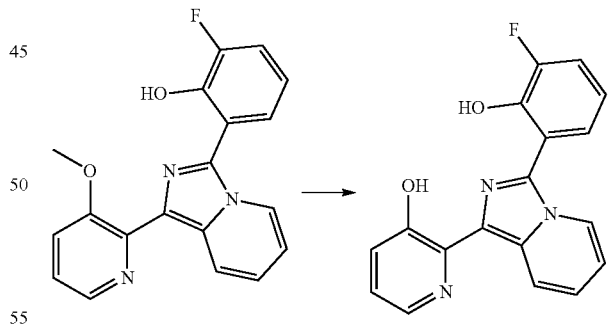

2-Fluoro-6-(5-(3-methoxypyridin-2-yl)imidazo[1,5-b]pyridazin-7-yl)phenol (16 mg) was dissolved in 48% HBr$_{(aq)}$ and heated to 110° C. for 36 h then for a further 16 h at 130° C. before cooling and diluting with water. The mixture was neutralised with conc. NH$_{3(aq)}$ and re-buffered with AcOH to ~pH4-5. The result solid was filtered and pumped dry to yield the crude product. The sample was further purified on C18 SiO$_2$ using ACN/water containing 0.1% formic acid in both phases and a gradient of 0-0% SCV, 0-100% 30 CV, 100-100% 10 CV. The desired fractions were combined and evaporated to yield the title compound (9.6 mg) as a dark yellow solid. $t_R$ 5.52 min (HPLC1); $^1$H NMR (d$_6$-Acetone, 600 MHz) δ 11.4 (1H, bs), 10.0 (1H, bs), 9.09 (1H, d, J 8.9 Hz), 8.53 (1H, s), 8.23 (1H, s), 7.93 (1H, d, J 7.5 Hz), 7.35 (1H, d, J 8.1 Hz), 7.32 (1H, t, J 9.9 Hz), 7.25-7.19 (1H, m), 7.11-7.03 (2H, m); m/z (MH$^+$) 323.09.

2-(7-(2-Hydroxyphenyl)imidazo[1,5-b]pyridazin-5-yl)pyridin-3-ol (120)

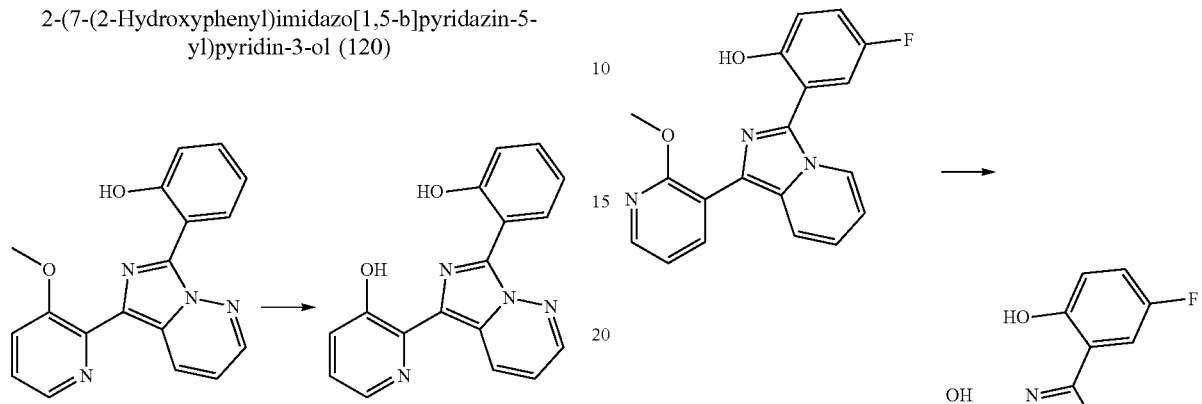

2-(5-(3-Methoxypyridin-2-yl)imidazo[1,5-b]pyridazin-7-yl)phenol (17.7 mg) was deprotected using general method Di) at 110° C. for 36 h and 130° C. for 16 h. The sample was worked up with NH$_{3(aq)}$ and extracted with CHCl$_3$ (4×) to yield the crude product which was further purified on 4 g C18 SiO$_2$ using ACN/water gradient containing 0.1% formic acid in both phases employing a gradient of 0-0% 5 CV, 0-100% 30 CV, 100-100% 10 CV. The desired fractions were combined and evaporated to yield the title compound (7.4 mg) as a dark yellow solid. $t_R$ 5.22 min (>95%, HPLC1); $^1$H NMR (d$_6$-DMSO, 600 MHz) δ 11.99 (1H, s), 9.91 (1H, s), 9.23 (1H, d, J 9.9 Hz), 8.94 (1H, d, J 4.2 Hz), 8.67 (1H, d, J 4.5 Hz), 8.52 (1H, dd, J 7.8, 1.5 Hz), 7.87 (1H, t, J 7.7 Hz), 7.78 (1H, d, J 8.2 Hz), 7.66 (1H, dd, J 8.2, 4.7 Hz), 7.57-7.47 (3H, m); m/z (MH$^+$) 305.10.

3-(3-(2-Hydroxyphenyl)imidazo[1,5-a]pyridin-1-yl)pyridin-2-ol (141)

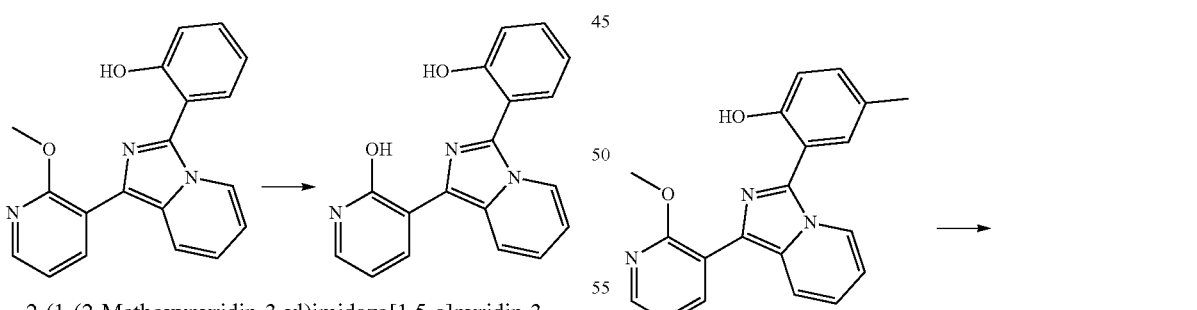

2-(1-(2-Methoxypyridin-3-yl)imidazo[1,5-a]pyridin-3-yl)phenol (62 mg) was heated in a 48% HBr$_{(aq)}$ (0.5 mL) at 120° C. for 17 h. The reaction was cooled then concentrated under reduced pressure to afford a solid. The solid was treated with sat. NaHCO$_{3(aq)}$ (10 mL) and sonicated to gain a uniform suspension, then filtered and the residue was washed with water (2×), triturated in EtOH and air dried to yield the title compound (26 mg), isolated as a mustard coloured solid. $t_R$ 7.04 min (91%, HPLC2); $^1$H NMR (CDCl$_3$, 600 MHz) δ 11.87 (1H, s), 10.48 (1H, s), 8.17 (1H, d, J 11.4 Hz), 8.01 (1H, d, J 8.4 Hz), 7.82 (1H, d, J 8.4 Hz), 7.54 (1H, d, J 8.4 Hz), 7.41-7.38 (2H, m), 7.06 (1H, d, J 9.6 Hz), 7.00 (1H, t, J 8.4 Hz), 6.89 (1H, bt, J 8.4 Hz), 6.74 (1H, bt, J 8.4 Hz), 6.36 (1H, t, J 7.8 Hz); m/z (MH$^+$) 340.11.

3-(3-(5-Fluoro-2-hydroxyphenyl)imidazo[1,5-a]pyridin-1-yl)pyridin-2-ol (144)

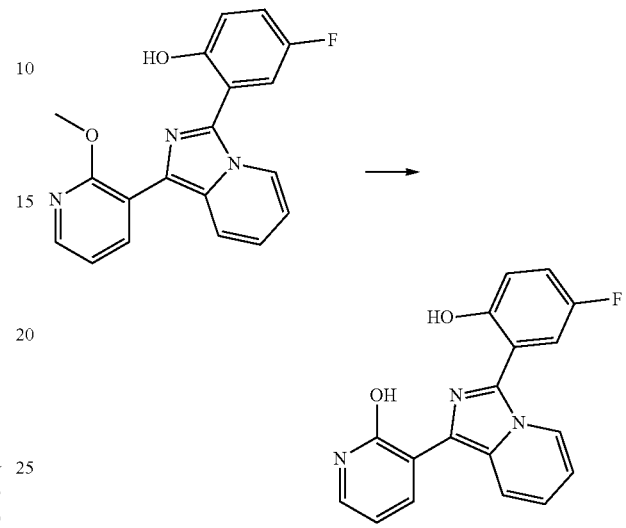

4-Fluoro-2-(1-(2-methoxypyridin-3-yl)imidazo[1,5-a]pyridin-3-yl)phenol (150 mg) was heated in 48% HBr$_{(aq)}$ (0.5 mL) at 120° C. for 17 h. The reaction was cooled then concentrated under reduced pressure to afford a solid. The solid was treated with a sat. NaHCO$_{3(aq)}$ (10 mL) and sonicated to gain a uniform suspension, then filtered and the residue was washed with water (2×), and air dried to yield the title compound (127 mg) as a yellow coloured solid. $t_R$ 7.14 min (100%, HPLC2); $^1$H NMR (CDCl$_3$, 600 MHz) δ 11.75 (1H, s), 10.37 (1H, s), 8.17 (1H, d, J 9.0 Hz), 7.99 (1H, d, J 6.0 Hz), 7.79 (1H, d, J 7.2 Hz), 7.33 (1H, d, J 5.4 Hz), 7.31 (1H, dd, J 9.0, 3.0 Hz), 7.19 (1H, td, J 11.4, 2.4 Hz), 7.01 (1H, dd, J 9.0, 4.2 Hz), 6.82 (1H, dd, J 9.0, 6.0 Hz), 6.68 (1H, t, J 6.6 Hz), 6.32 (1H, t, J 6.6 Hz); m/z (MH$^+$) 322.10.

3-(3-(2-Hydroxy-5-methylphenyl)imidazo[1,5-a]pyridin-1-yl)pyridin-2-ol (147)

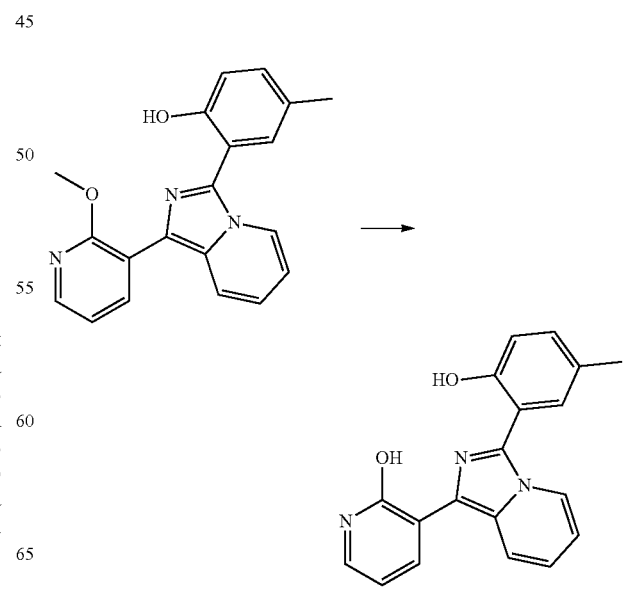

2-(1-(2-Methoxypyridin-3-yl)imidazo[1,5-a]pyridin-3-yl)-4-methylphenol (130 mg) was heated in a 48% HBr$_{(aq)}$ (0.5 mL) at 120° C. for 17 h. The reaction was cooled then concentrated under reduced pressure to afford a solid. The solid was treated with sat. NaHCO$_{3(aq)}$ (10 mL) and sonicated to gain a uniform suspension, then filtered and the residue was washed with water (2×), hexane (1×), ether (1×) and air dried to yield the title compound (108 mg) as a yellow coloured solid. t$_R$ 7.66 min (98%, HPLC2); $^1$H NMR (CDCl$_3$, 600 MHz) δ 12.21 (1H, s), 10.59 (1H, s), 8.06 (1H, d, J 9.6 Hz), 7.99 (1H, d, J 6.6 Hz), 7.95 (1H, d, J 7.2 Hz), 7.54 (1H, d, J 6.0 Hz), 7.40 (1H, s), 7.32 (1H, d, J 7.8 Hz), 7.16 (1H, t, J 7.2 Hz), 7.01-7.05 (2H, m), 6.43 (1H, t, J 6.6 Hz), 2.29 (3H, s); m/z (MH$^+$) 318.12.

2-(1-(3-Methoxypyridin-2-yl)imidazo[1,5-a]pyridin-3-yl)phenol (3)

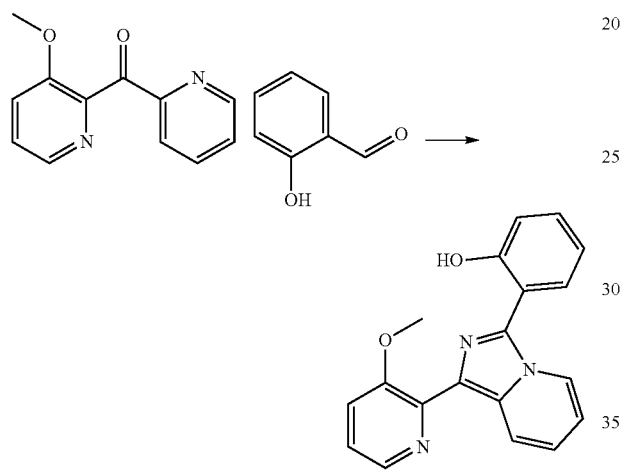

The title compound was prepared employing the general Method H using (3-methoxypyridin-2-yl)(pyridin-2-yl)methanone (150 mg), salicylaldeyde (225 μL) and ammonium acetate (540 mg) suspended in AcOH (3 mL) with heating at 60° C. for 18 h. The product was extracted with DCM to yield the crude product which was further purified on SiO$_2$ using MeOH/DCM gradient 0-0% 5CV, 0-10% 20 CV. The desired fractions were combined and evaporated to yield the title compound (165 mg) as a pale yellow solid. $^1$H NMR (CDCl$_3$, 600 MHz) δ 12.77 (1H, bs), 8.58 (1H, dt, J 7.4, 1.1 Hz), 8.49 (1H, dt, J 9.3, 1.3 Hz), 8.30 (1H, dd, J 4.7, 1.4 Hz), 7.81 (1H, dd, J 7.9, 1.7 Hz), 7.32 (1H, dd, J 8.3, 1.3 Hz), 7.30 (1H, ddd, J 8.2, 7.3, 1.6 Hz), 7.18 (1H, dd, J 8.4, 4.6 Hz), 7.17 (1H, dd, J 8.3, 1.3 Hz), 6.99 (1H, dt, J 7.4, 1.3 Hz), 6.94 (1H, ddd, J 9.3, 6.4, 0.9 Hz), 6.76 (1H, ddd, J 7.5, 6.3, 1.3 Hz), 3.99 (3H, s); m/z (MH$^+$) 318.13.

3-Fluoro-2-(1-(2-hydroxyphenyl)imidazo[1,5-a]pyridin-3-yl)phenol (18)

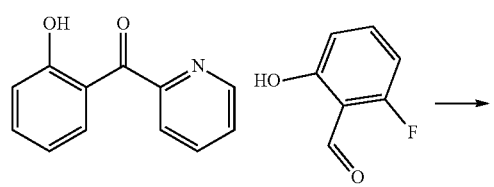

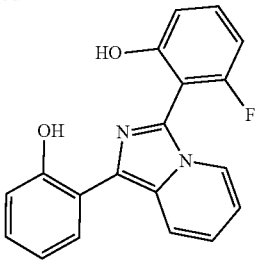

The title compound was prepared employing the general Method H using (2-hydroxyphenyl)(pyridin-2-yl)methanone (60 mg), 2-fluoro-6-hydroxybenzaldehyde (127 mg), ammonium acetate (232 mg) dissolved in AcOH (2 mL). The reaction was heated 110° C. for 18 h. The sample was diluted into water and extracted with EtOAc (3×) to yield the crude product which was adsorbed onto SiO$_2$ and the solvent evaporated. The sample was purified by flash chromatography on 12 g SiO$_2$ using an EtOAc/hexanes gradient 0-0% 3 CV, 0-50% 20 CV and the target fraction collected to yield the title compound (42.5 mg) as a pale orange solid. $^1$H NMR (CDCl$_3$, 600 MHz) δ 9.52 (1H, bs), 7.99 (1H, d, J 9.5 Hz), 7.87 (1H t, J 6.4 Hz), 7.74 (1H, dd, J 7.7, 1.3 Hz), 7.38 (1H, td, J 8.3, 6.7 Hz), 7.27 (1H, ddd, J 8.1, 7.2, 1.5 Hz), 7.11 (1H, dd, J 8.2, 1.3 Hz), 7.03-7.00 (2H, m), 6.99 (1H, dt, J 8.3, 0.9 Hz), 6.86-6.80 (2H, m), One phenol not observed; m/z (MH$^+$) 321.10.

2-Chloro-6-(1-(3-fluoro-2-hydroxyphenyl)imidazo[1,5-a]pyridin-3-yl)phenol (41)

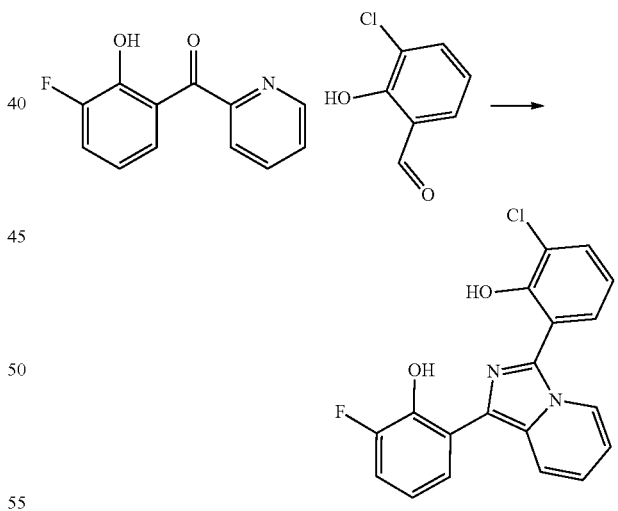

The title compound was prepared employing the general Method H using 2-Fluoro-6-(hydroxyl(pyridine-2-yl)methyl)phenol (110 mg), 3-chloro-2-hydroxybenzaldehyde (220 mg) and ammonium acetate (180 mg) suspended in acetic acid (4.0 mL) with the reaction being heated at 110° C. for 18 h. The isolated gum was purified by flash chromatography using an EtOAc/hexanes gradient 0-50% 33 CVs to afford the title compounds as a pale brown solid (13 mg, 8%). t$_R$ 9.31 min (89%, HPLC2); $^1$H NMR (d$_6$-DMSO, 600 MHz) δ 12.10 (1H, s), 10.44 (1H, bs), 8.10 (1H, d, J 9.6 Hz), 7.98 (1H, d, J 6.6 Hz), 7.67 (1H, d, J 7.2 Hz), 7.58 (1H, d, J 7.8 Hz), 7.55 (1H, J 7.2 Hz), 7.04-7.11 (3H, m), 6.89-6.92 (2H, m); m/z (MH⁺) 355.07.

Methyl 4-hydroxy-3-(1-(2-hydroxyphenyl)imidazo[1,5-a]pyridin-3-yl)benzoate (22)

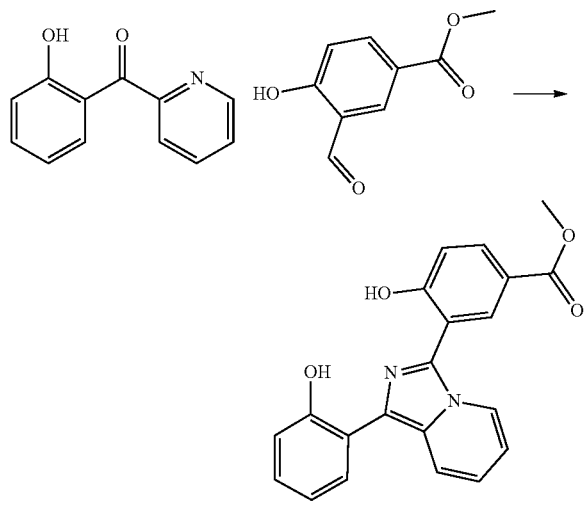

The title compound was prepared employing the general Method H using (2-hydroxyphenyl)(pyridin-2-yl)methanone (60 mg), methyl 3-formyl-4-hydroxybenzoate (127 mg), ammonium acetate (232 mg) dissolved in AcOH (2 mL) with the reaction being heated at 110° C. for 18 h. The sample was purified by flash chromatography on 12 g SiO$_2$ using an EtOAc/hexanes gradient 0-0% 3 CV, 0-50% 20 CV and the target fractions collected to yield the title compound (90 mg) as a pale tan solid. $^1$H NMR (CDCl$_3$, 600 MHz) δ 9.92 (2H, bs), 8.45 (1H, d, J 2.1 Hz), 8.44 (1H, dt, J 7.3, 0.9 Hz), 8.04 (1H, dd, J 8.6, 2.1 Hz), 7.93 (1H, dt, J 9.4, 1.2 Hz), 7.67 (1H, dd, J 7.7, 1.7 Hz), 7.28 (1H, ddd, J 8.2, 7.3, 1.6 Hz), 7.22 (1H, d, J 8.6 Hz), 7.11 (1H, dd, J 8.2, 1.3 Hz), 7.02 (1H, dt, J 7.5, 1.3 Hz), 6.96 (1H, ddd, J 9.3, 6.4, 1.0 Hz), 6.84 (1H, ddd, J 7.4, 6.4, 1.2 Hz), 3.94 (3H, s); m/z (MH⁺) 361.12.

4-Fluoro-2-(1-(3-methoxypyridin-2-yl)imidazo[1,5-a]pyridin-3-yl)phenol (56)

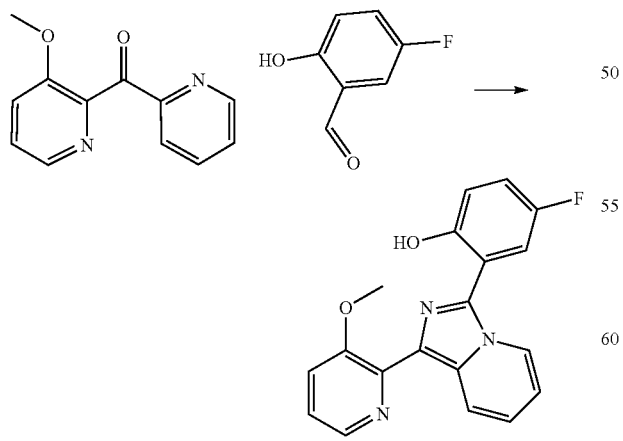

The title compound was prepared employing the general Method H using (3-methoxypyridin-2-yl)(pyridin-2-yl)methanone (50 mg), 5-fluoro-2-hydroxybenzaldehyde (72 mg) and ammonium acetate (180 mg) suspended in AcOH (1 mL) with the reaction being heated for 22 h at 60° C. The product was was purified by flash chromatography on 4 g SiO$_2$ using EtOAc/hexanes gradient 0-0% 3 CV, 0-100%, 30 CV to yield the title compound (62 mg) as a yellow solid. t$_R$ 5.66 min (>95%, HPLC1); $^1$H NMR (CDCl$_3$, 600 MHz) δ 8.55-8.52 (2H, m), 8.32 (1H, d, J 4.7 Hz), 7.51 (1H, d, J 9.6 Hz), 7.35 (1H, d, J 8.2 Hz), 7.22 (1H, dd, J 8.2, 4.7 Hz), 7.12 (1H, dd, J 9.0, 5.1 Hz), 7.04-6.99 (2H, m), 6.85 (1H, t, J 6.6 Hz), 4.00 (3H, s), Phenol proton not observed; m/z (MH⁺) 336.11.

2,2'-(Imidazo[1,5-a]pyrimidine-6,8-diyl)diphenol (107)

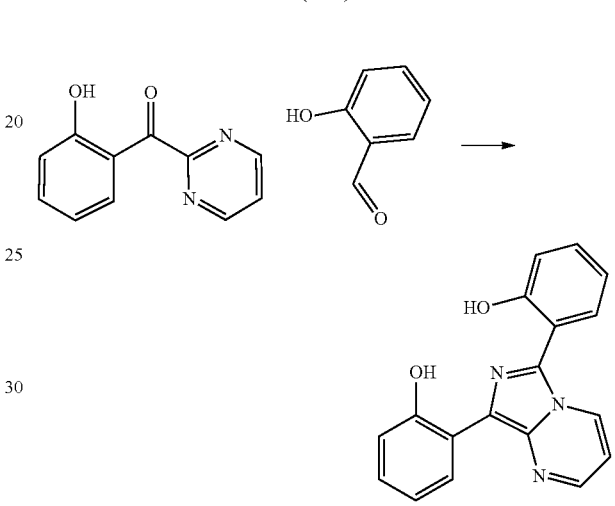

The title compound was prepared employing the general Method H using (2-hydroxyphenyl)(pyrimidin-2-yl)methanone (40 mg), 2-hydroxybenzaldehyde (54 mg) and ammonium acetate (155 mg) suspended in AcOH (0.5 mL) with the reaction being heated at 90° C. for 22 h. The product was purified by flash chromatography on 4 g SiO$_2$ using EtOAc/hexanes gradient 0-0% 3 CV, 0-100%, 30 CV and the desired fractions were combined and evaporated to yield an impure solid. The sample was recrystallised from MeOH$_{(aq)}$ to yield the title compound (4.7 mg) as a pale yellow solid. t$_R$ 8.58 min (92%, HPLC1); $^1$H NMR (d$_6$-DMSO, 600 MHz) δ 12.31 (1H, s), 10.46 (1H, s), 8.67 (1H, d, J 7.8 Hz), 8.45-8.43 (1H, m), 8.31 (1H, d, J 7.6 Hz), 7.59 (1H, d, J 7.5 Hz), 7.44 (1H, t, J 7.8 Hz), 7.17 (1H, t, J 7.8 Hz), 7.10 (1H, d, J 8.2 Hz), 7.05 (1H, t, J 6.9 Hz), 6.99-6.94 (2H, m), 6.93 (1H, d, J 8.2 Hz); m/z (MH⁺) 304.11.

2-Fluoro-6-(1-(2-hydroxyphenyl)imidazo[1,5-a]pyridin-3-yl)phenol (10)

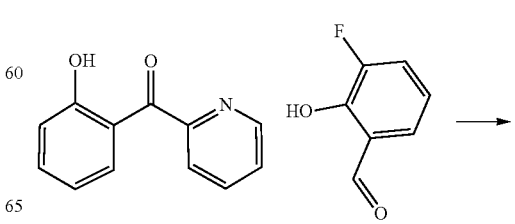

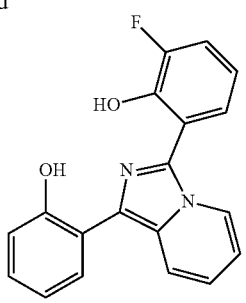

The title compound was prepared employing the general Method H using 3-fluoro-2-hydroxybenazaldehyde (260 mg), (2-hydroxyphenyl)(pyridine-2-yl)methanone (120 mg) and ammonium acetate (240 mg) suspended in acetic acid (6.2 mL) with the reaction being heated at 110° C. for 18 h. The extracted crude product was adsorbed onto $SiO_2$ and purified by flash chromatography using an EtOAc/hexanes gradient 0-50% 35 CV. The desired fractions were combined and evaporated yielding a solid which was sonicated in ethanol, filtered, washed with ethanol and air dried to yield the title compound (20 mg) as a yellow solid $t_R$ 6.12 min (99%, HPLC2); $^1$H NMR ($d_6$-DMSO, 600 MHz) δ 11.77 (1H, s), 10.60 (1H, bs), 8.07 (1H, d, J 9.6 Hz), 7.94 (1H, d, J 7.2 Hz), 7.83 (1H, d, J 7.8 Hz), 7.35-7.38 (2H, m), 7.13 (1H, t, J 7.2 Hz), 7.03-6.98 (2H, m), 6.93-6.90 (2H, m), 6.84 (1H, t, J 6.6 Hz); m/z (MH$^+$) 321.11.

2-(3-(2-Fluorophenyl)imidazo[1,5-a]pyridin-1-yl)pyridin-3-ol (13)

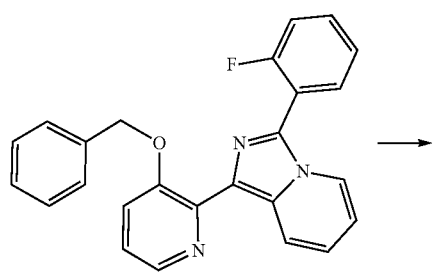

1-(3-(Benzyloxy)pyridin-2-yl)-3-(2-fluorophenyl)imidazo[1,5-a]pyridine (18 mg) was dissolved in 48% HBr (1 mL) and heated at 70° C. for 3 h after which time the reaction cooled and extracted with hexanes (3×) to removed BnBr before being made basic with conc. $NH_{3(aq)}$ and re-buffered to pH 4-5 by addition of AcOH. The product was extracted with EtOAc (3×) to yield the crude product which was adsorbed onto $SiO_2$ for purification. Purification was carried out on 4 g $SiO_2$ using an EtOAc/hexanes gradient 0-0% 3 CV, 0-100% 30 CV. The desired fractions were collected and evaporated to yield the title compound (11 mg) as a yellow solid. $t_R$ 5.56 min (>95%, HPLC1); $^1$H NMR (CDCl$_3$, 600 MHz) δ 12.3 (1H, bs), 8.87 (1H, d, J 9.5 Hz), 8.22 (1H, dd, J 4.7, 1.3 Hz), 7.91-7.88 (1H, m), 7.77 (1H, dt, J 7.6, 1.6 Hz), 7.56-7.51 (1H, m), 7.37 (1H, dt, J 7.5, 1.1 Hz), 7.32-7.27 (2H, m), 7.09 (1H, dd, J 8.1, 4.5 Hz), 7.04 (1H, dd, J 9.0, 6.5 Hz), 6.81 (1H, t, J 6.8 Hz); m/z (MH$^+$) 306.10.

2,2'-(Imidazo[1,5-b]pyridazine-5,7-diyl)diphenol (102)

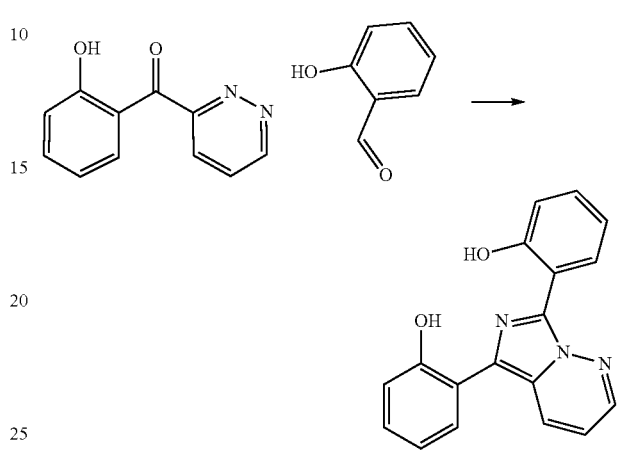

The title compound was prepared employing the general Method H using (2-hydroxyphenyl)(pyridazin-3-yl)methanone (26 mg), 2-hydroxybenzaldehyde (35 mg) and ammonium acetate (100 mg) suspended in acetic acid (0.5 mL) with the reaction being heated initially at 80° C. for 17 h then further at 90° C. for 6 h. The resultant mixture was triturated with hexanes (3×) before the residue was crystallised from EtOH/water to yield the title compound (25 mg) as a bright yellow solid. $t_R$ 5.48 min (>95%, HPLC1); $^1$H NMR ($d_6$-DMSO, 600 MHz) δ 12.33 (1H, s), 10.46 (1H, s), 8.65 (1H, d, J 8.0 Hz), 8.53 (1H, d, J 4.4 Hz), 8.42 (1H, d, J 9.3 Hz), 7.69 (1H, d, J 7.7 Hz), 7.36 (1H, t, J 7.5 Hz), 7.45 (1H, t, J 7.7 Hz), 7.07-7.00 (3H, m), 6.99 (1H, t, J 7.5 Hz), 6.93 (1H, ddd, J 9.3, 4.1, 1.4 Hz); m/z (MH$^+$) 304.11.

2-(1-(2-Hydroxyphenyl)imidazo[1,5-a]pyridin-3-yl)benzonitrile (16)

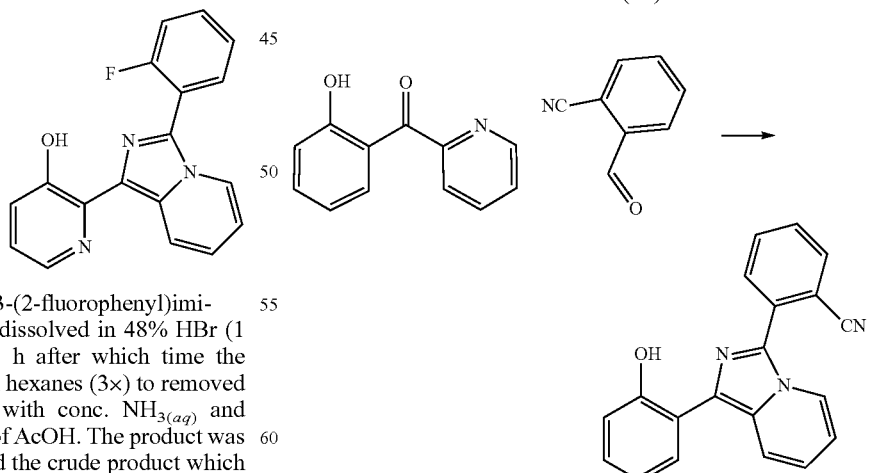

The title compound was prepared employing the general Method H using (2-hydroxyphenyl)(pyridin-2-yl)methanone (60 mg), 2-formylbenzonitrile (118 mg) and ammonium acetate (232 mg) suspended in acetic acid (1.5 mL) with the reaction being heated at 110° C. for 18 h. The extracted crude product was adsorbed onto SiO$_2$ and purified by flash chromatography using an EtOAc/hexanes gradient 0-0% 3 CV, 0-60% 35 CV. The desired fractions were combined and evaporated to yield the title compound (20 mg) as a dark yellow solid. $^1$H NMR (CDCl$_3$, 600 MHz) δ 11.68 (1H, s), 8.09 (1H, dt, J 7.2, 1.1 Hz), 8.05 (1H, dt, J 9.3, 1.2 Hz), 7.91 (1H, ddd, J 7.8, 1.3, 0.6 Hz), 7.84 (1H, ddd, J 7.9, 1.3, 0.7 Hz), 7.80-7.75 (2H, m), 7.60 (1H, dt, J 7.6, 1.3 Hz) 7.22 (1H, ddd, J 8.9, 7.3, 1.6 Hz), 7.10 (1H, dd, J 8.1, 1.3 Hz), 6.99-6.95 (2H, m), 6.79 (1H, ddd, J 7.2, 6.5, 1.2 Hz); m/z (MH$^+$) 312.11.

2-(3-(3-Fluoro-2-hydroxyphenyl)imidazo[1,5-a]pyridin-1-yl)-5-(trifluoromethyl)phenol (98)

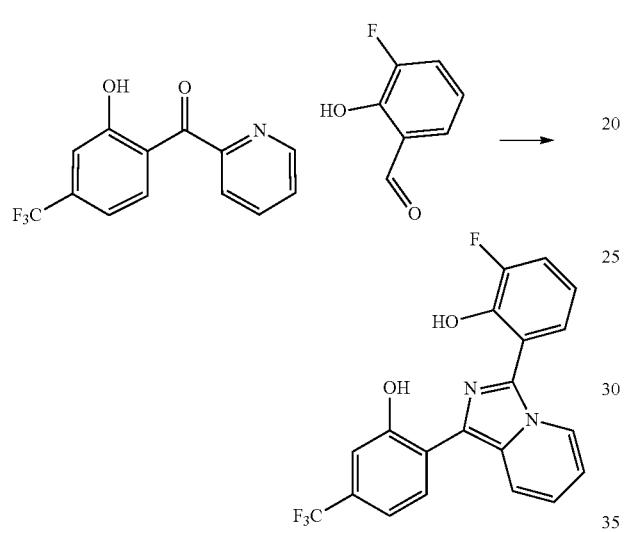

The title compound was prepared employing the general Method H using (2-hydroxy-4-(trifluoromethyl)phenyl)(pyridin-2-yl)methanone (60 mg), 3-fluoro-2-hydroxybenzaldehyde (100 mg) and ammonium acetate (90 mg) suspended in acetic acid (2.5 mL) with the reaction being heated at 110° C. for 18 h. The sample was adsorbed onto SiO$_2$ and purified by flash chromatography using an EtOAc/hexanes gradient 0-40% 33 CV. The desired fractions were combined and evaporated to yield the title compound (54 mg) as a yellow solid. t$_R$ 10.86 min (98%, HPLC2). $^1$H NMR (d$_6$-DMSO, 600 MHz) δ 12.26 (1H, bs), 10.56 (1H, bs), 8.13 (1H, d, J 9.0 Hz), 8.05 (1H, d, J 8.4 Hz), 7.97 (1H, d, J 7.2 Hz), 7.23-7.39 (2H, m), 7.19-7.23 (2H, m), 7.11 (1H, dd, J 9.6, 7.2 Hz), 7.00 (1H, m), 6.89 (1H, t, J 7.2 Hz); m/z (MH$^+$) 389.08.

5-Chloro-2-(1-(2-methoxyphenyl)-7-methylimidazo[1,5-a]pyridin-3-yl)phenol (100)

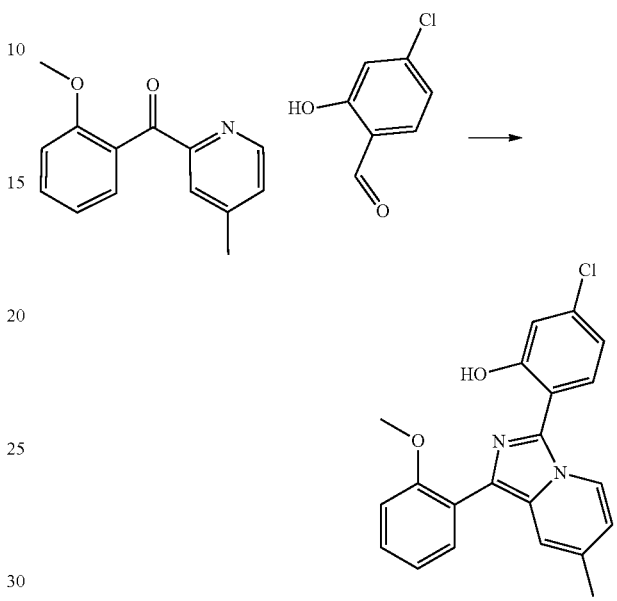

The title compound was prepared employing the general Method H using (2-methoxyphenyl)(4-methylpyridin-2-yl)methanone (50 mg), 4-chloro-2-hydroxybenzaldehyde (68 mg) and ammonium acetate (80 mg) suspended in acetic acid (2.5 mL) with the reaction being heated at 110° C. for 18 h. The sample was purified by flash chromatography using an EtOAc/hexanes gradient 0-25% 12 CV. The desired fractions were combined and evaporated to yield the title compound as an orange solid. $^1$H NMR (d$_6$-DMSO, 600 MHz) δ 11.24 (1H, bs), 7.90 (1H, d, J 7.2 Hz), 7.61-7.57 (2H, m), 7.34-7.28 (2H, m), 7.19 (1H, d, J 7.8 Hz), 7.08-7.02 (3H, m), 6.60 (1H, dd, J 7.2, 1.8 Hz), 3.82 (3H, s), 2.29 (3H, s); m/z (MH$^+$) 365.10.

2-(1-(2-Hydroxyphenyl)imidazo[1,5-a]pyridin-3-yl)pyridin-3-ol (95)

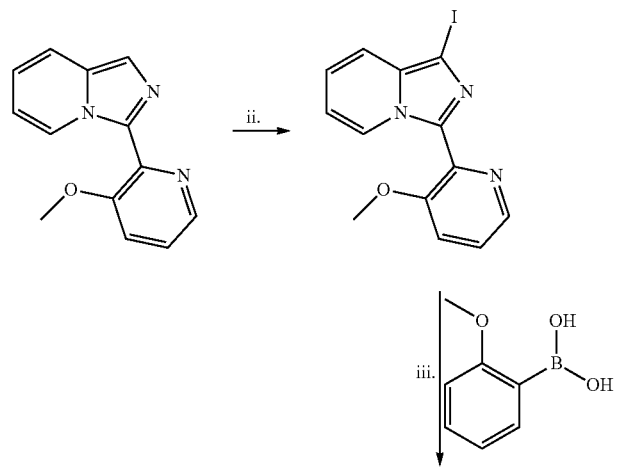

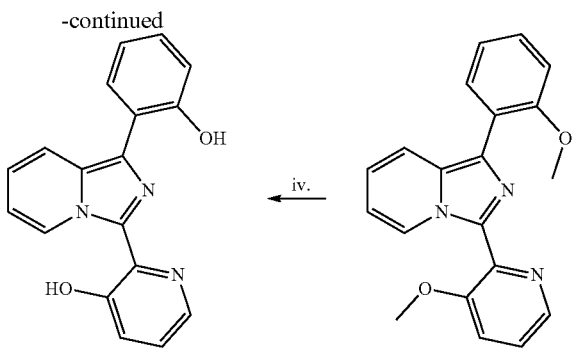

i) Pd (OAc)2, KOAc, PPh3, Bu4NBr; ii) I2; iii) Boronic acid, Pd(PPh3)4, K2CO3; iv) HBr$_{(aq)}$

3-(3-Methoxypyridin-2-yl)imidazo[1,5-a]pyridine

An adaption of method described by Huang, C. et al. Chem. Letts. 2011, 40, pp 1053-1054.

Imidazo[1,5-a]pyridine (260 mg), 2-iodo-3-methoxypyridine (520 mg), Pd(OAc)$_2$ (24 mg), PPh$_3$ (58 mg), KOAc (1.08 g) and Bu$_4$NBr (1.42 g) were suspended in toluene (6 mL) and placed under Ar. The mixture was heated to reflux and stirred for 19 h after which time the reaction was diluted with EtOAc and filtered through a Celite® plug. SiO$_2$ was added to the filtrate and the solvent evaporated to yield crude product adsorbed onto SiO$_2$. The SiO$_2$ was dry loaded onto a 12 g SiO$_2$ column and purified using MeOH/EtOAc gradient 0-0% 10 CV, 0-10% 40 CV. The fractions containing the desired product were combined and evaporated to yield the title compound (172 mg) which was used without further manipulation. $^1$H NMR (CDCl$_3$, 600 MHz) δ 8.88 (1H, d, J 7.3 Hz), 8.27 (1H, dd, J 4.5, 1.1 Hz), 7.61 (1H, s), 7.46 (1H, d, J 9.2 Hz), 7.33 (1H, d, J 8.5 Hz), 7.23 (1H, dd, J 8.4, 4.6 Hz), 6.75 (1H, dd, J 9.0, 6.3 Hz), 6.55 (1H, ddd, J 7.3, 6.5, 1.2 Hz), 3.89 (3H, s).

1-Iodo-3-(3-methoxypyridin-2-yl)imidazo[1,5-a]pyridine

The method of Shinahara, F. et al. Tetrahedron 2009, 65, pp 5062-5073 was employed.

Iodine (80 mg) was added to a solution of 3-(3-methoxypyridin-2-yl)imidazo[1,5-a]pyridine (48 mg) in THF under Ar and the resulting solution heated to reflux for 1.5 h. After this time the reaction was quenched by dilution with EtOAc and sat. Na$_2$S$_2$O$_{3(aq)}$. The EtOAc layer was separated and the aqueous layer extracted with further EtOAc (2×) before the combined extracts were dried and the solvent evaporated to yield the title product (46 mg) which was used without further manipulation. $^1$H NMR (CDCl$_3$, 600 MHz) δ 8.69 (1H, d, J 7.3 Hz), 8.31 (1H, dd, J 4.6, 1.3 Hz), 7.40-7.35 (2H, m), 7.30 (1H, dd, J 8.4, 4.6 Hz), 6.87 (1H, ddd, J 9.2, 6.6, 0.9 Hz), 6.64 (1H, ddd, J 7.3, 6.5, 1.2 Hz), 3.91 (3H, s).

1-(2-Methoxyphenyl)-3-(3-methoxypyridin-2-yl)imidazo[1,5-a]pyridine

1-Iodo-3-(pyridin-2-yl)imidazo[1,5-a]pyridine (120 mg) dissolved in 1,4-dioxane (2 mL) was added to 2-methoxyphenylboronic acid (65 mg), Pd(PPh$_3$)$_4$ (20 mg) and K$_2$CO$_{3(aq)}$ (120 mg) in a vial flushed with Ar before water (430 µL) was added. The reaction was stirred for 2 mins then placed into heating block at 95° C. and stirred for 6 h after which time the reaction was diluted with water and extracted with EtOAc (3×). The combined extracts were dried and the solvent evaporated to yield the crude product. The sample was initially purified on 4 g SiO$_2$ column using EtOAc/hexanes gradient 0-0% 3 CV, 0-100% 30 CV, 100-100% 10 CV which was contaminated with triphenylphosphine oxide (TPPO). The sample was further purified on 4 g SiO$_2$ eluting with 2% AcOH in DCM to selectively removed the TPPO. Once eluted, the solvent was switched to MeOH/DCM using a gradient 0-0% 3 CV, 0-5% 20 CV to yield the title product (49 mg) which was used without further manipulation. $^1$H NMR (CDCl$_3$, 600 MHz) δ 8.61 (1H, d, J 7.4 Hz), 8.35 (1H, dd, J 4.6, 1.3 Hz), 7.82 (1H, dd, J 7.6, 1.7 Hz), 7.61 (1H, d, J 9.2 Hz), 7.37 (1H, dd, J 8.4, 1.1 Hz), 7.34-7.28 (2H, m), 7.07 (1H, dt, J 7.4, 0.8 Hz), 7.01 (1H, d, J 8.2 Hz), 6.79 (1H, ddd, J 9.3, 6.4, 0.8 Hz), 6.60 (1H, ddd, J 7.4, 6.4, 1.2 Hz), 3.91 (3H, s), 3.86 (3H, s).

2-(1-(2-Hydroxyphenyl)imidazo[1,5-a]pyridin-3-yl)pyridin-3-ol 1-(2-Methoxyphenyl)-3-(3-methoxypyridin-2-yl)imidazo[1,5-a]pyridine (48 mg) was dissolved in 48% HBr$_{(aq)}$ (0.5 mL) and heated to 100° C. for 22 h after which time SM was still present. The reaction temperature was increase to 120° C. and heating continued for a further 24 h after which additional 48% HBr$_{(aq)}$ (0.5 mL) was added and heating continued till for a further 2 h after which time the reaction was allowed to cool 0/N before being quenched with conc. NH$_{3(aq)}$. The resultant sample was solubilised with a large volume of EtOAc and separated from the aqueous layer. The aqueous layer was further extracted with smaller portions of EtOAc (2×) before the combined extracts were dried and the solvent evaporated to yield the crude target. The sample was recrystallised from MeOH to yield the title compound (4.2 mg) as a tan solid. HPLC (230 nm) t$_R$ 5.93 min (86%), $^1$H NMR (d$_6$-DMSO, 600 MHz) δ 13.07 (1H, bs), 10.01 (1H, dt, J 7.3, 1.2 Hz), 10.00 (1H, bs), 8.28 (1H, dd, J 4.8, 1.6 Hz), 7.85 (1H, dt, J 9.2, 1.2 Hz), 7.58 (1H, dd, J 7.7, 1.9 Hz), 7.47 (1H, dd, J 8.0, 1.3 Hz), 7.33 (1H, dd, J 8.4, 4.8 Hz), 7.25 (1H, dt, J 7.6, 1.5 Hz), 7.12 (1H, ddd, J 9.1, 6.5, 1.1 Hz), 7.06 (1H, dt, J 7.6, 1.5 Hz), 7.03 (1H, dd, J 8.2 0.9 Hz), 6.97 (1H, dt, J 7.6, 1.3 Hz), m/z (MH$^+$) 304.11.

A combination of the general methods described above was used to prepare the compounds shown in Table 2. The table details the reference number (No.), structure, general method used (Mthd) and the observed molecular mass for the target (Obs m/z M+H+).

TABLE 2

| No. | Structure | Mthd | Obs m/z M + H⁺ |
|---|---|---|---|
| 1 | 1-(2-methoxyphenyl)-3-(2-hydroxyphenyl)imidazo[1,5-a]pyridine | H | 317.13 |
| 2 | 1,3-bis(2-hydroxyphenyl)imidazo[1,5-a]pyridine | D | 303.12 |
| 3 | 1-(3-methoxypyridin-2-yl)-3-(2-hydroxyphenyl)imidazo[1,5-a]pyridine | H | 318.13 |
| 4 | 1-(3-hydroxypyridin-2-yl)-3-(2-hydroxyphenyl)imidazo[1,5-a]pyridine | D | 304.11 |
| 5 | 1-(2-hydroxyphenyl)-3-phenylimidazo[1,5-a]pyridine | D | 287.12 |
| 6 | 1-(5-bromo-2-hydroxyphenyl)-3-phenylimidazo[1,5-a]pyridine | D | 365.03 |
| 7 | 1-(2-hydroxyphenyl)-3-(3,5-dichloro-2-hydroxyphenyl)imidazo[1,5-a]pyridine | H | 371.04 |
| 8 | 1-(2-hydroxyphenyl)-3-(5-chloro-2-hydroxyphenyl)imidazo[1,5-a]pyridine | H | 337.07 |

TABLE 2-continued

Compounds of formula (I)

| No. | Structure | Mthd | Obs m/z M + H+ |
|---|---|---|---|
| 9 | 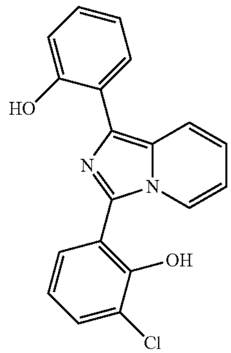 [SMILES: Oc1ccccc1-c1nc(-c2cccc(Cl)c2O)n2ccccc12] | H | 337.07 |
| 10 | 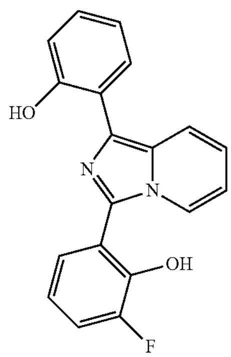 [SMILES: Oc1ccccc1-c1nc(-c2cccc(F)c2O)n2ccccc12] | H | 321.11 |
| 11 | 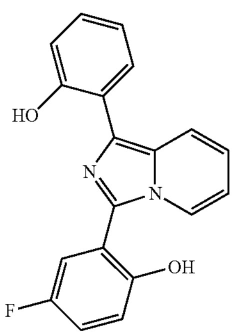 [SMILES: Oc1ccccc1-c1nc(-c2cc(F)ccc2O)n2ccccc12] | H | 321.10 |
| 12 | 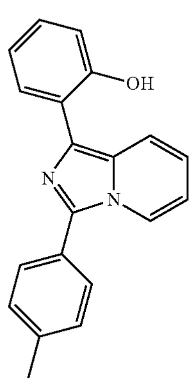 [SMILES: Cc1ccc(-c2nc(-c3ccccc3O)c3ccccn23)cc1] | H | 301.04 |
| 13 |  | H | 305.11 |
| 14 |  | H | 312.11 |
| 15 |  | H | 312.11 |
| 16 |  | H | 312.11 |

TABLE 2-continued

Compounds of formula (I)

| No. | Structure | Mthd | Obs m/z M + H+ |
|---|---|---|---|
| 17 | 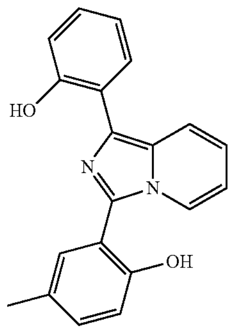 [SMILES: Cc1ccc(O)c(-c2nc(-c3ccccc3O)c3ccccn23)c1] | H | 317.13 |
| 18 | 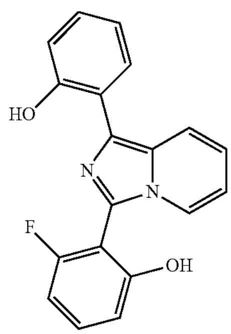 [SMILES: Oc1ccccc1-c1nc(-c2c(O)cccc2F)n2ccccc12] | H | 321.10 |
| 19 | 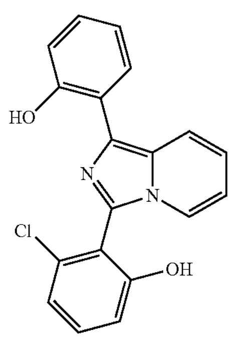 [SMILES: Oc1ccccc1-c1nc(-c2c(O)cccc2Cl)n2ccccc12] | H | 337.07 |
| 20 | 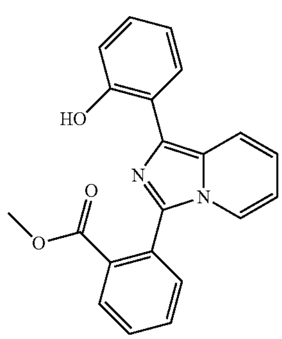 [SMILES: COC(=O)c1ccccc1-c1nc(-c2ccccc2O)c2ccccn12] | H | 345.12 |
| 21 | | H | 355.04 |
| 22 | | H | 361.12 |
| 23 | | H | 339.09 |
| 24 | | H | 355.04 |

TABLE 2-continued
Compounds of formula (I)
| No. | Structure | Mthd | Obs m/z M + H+ |
|---|---|---|---|
| 25 | 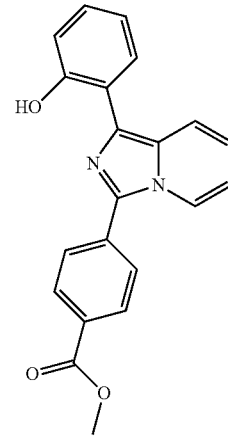 [SMILES: COC(=O)c1ccc(-c2nc(-c3ccccc3O)c3ccccn23)cc1] | H | 345.12 |
| 26 | 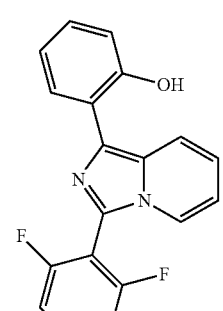 | H | 323.10 |
| 27 | 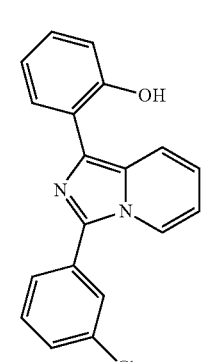 | H | 321.08 |
| 28 | 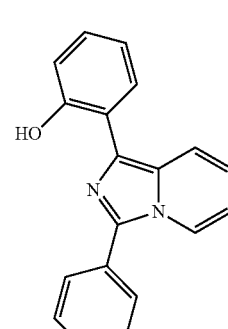 | H | 301.13 |
| 29 | 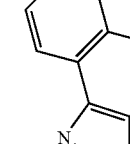 | H | 321.08 |
| 30 | 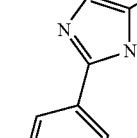 | H | 381.02 |
| 31 | 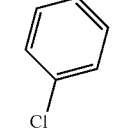 | H | 399.01 |
| 32 | 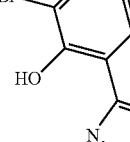 | H | 414.99 |

TABLE 2-continued

Compounds of formula (I)

| No. | Structure | Mthd | Obs m/z M + H+ |
|---|---|---|---|
| 33 | (Br, HO-phenyl)-imidazo[1,5-a]pyridine-(OH, F, F-phenyl) | H | 417.01 |
| 34 | (Br, HO-phenyl)-imidazo[1,5-a]pyridine-(F, OH-phenyl) | H | 399.01 |
| 35 | (Br, HO-phenyl)-imidazo[1,5-a]pyridine-(Cl, OH-phenyl) | H | 414.99 |
| 36 | (Br, HO-phenyl)-imidazo[1,5-a]pyridine-(OH, F-phenyl) | H | 399.01 |
| 37 | (F, HO-phenyl)-imidazo[1,5-a]pyridine-(OH-phenyl) | H | 321.10 |
| 38 | (F, HO-phenyl)-imidazo[1,5-a]pyridine-(F, OH-phenyl) | H | 339.09 |
| 39 | (F, HO-phenyl)-imidazo[1,5-a]pyridine-(Cl, OH-phenyl) | H | 355.06 |
| 40 | (F, HO-phenyl)-imidazo[1,5-a]pyridine-(OH, F-phenyl) | H | 339.09 |

TABLE 2-continued

Compounds of formula (I)

| No. | Structure | Mthd | Obs m/z M + H+ |
|---|---|---|---|
| 41 | 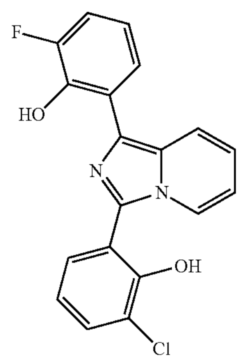 [SMILES: Oc1c(F)cccc1-c1nc(-c2cccc(Cl)c2O)n2ccccc12] | H | 355.07 |
| 42 | 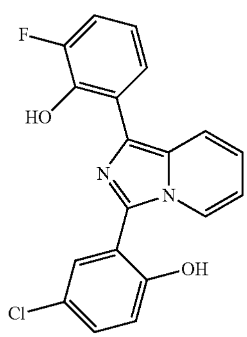 [SMILES: Oc1ccc(Cl)cc1-c1nc(-c2cccc(F)c2O)c2ccccn12] | H | 355.06 |
| 43 | 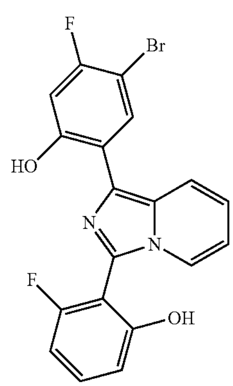 | H | 432.98 |
| 44 | 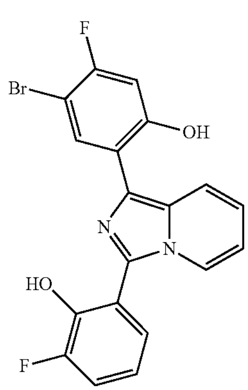 [SMILES: Oc1cc(F)c(Br)cc1-c1nc(-c2cccc(F)c2O)n2ccccc12] | H | 417.01 |
| 45 | 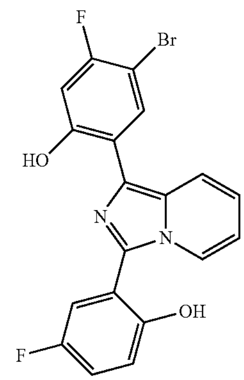 [SMILES: Oc1cc(F)c(Br)cc1-c1nc(-c2cc(F)ccc2O)n2ccccc12] | H | 417.01 |
| 46 | 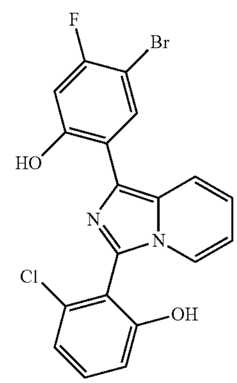 [SMILES: Oc1cc(F)c(Br)cc1-c1nc(-c2c(O)cccc2Cl)n2ccccc12] | H | 432.98 |
| 47 | 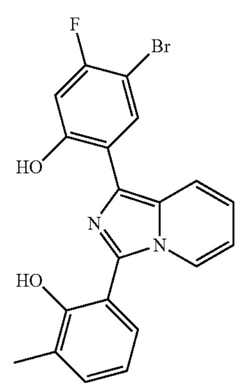 [SMILES: Cc1cccc(-c2nc(-c3cc(Br)c(F)cc3O)c3ccccn23)c1O] | H | 413.03 |
| 48 | 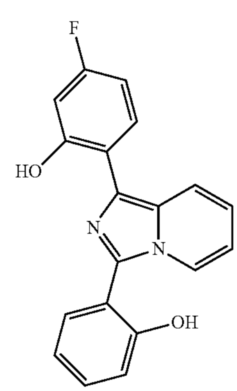 [SMILES: Oc1cc(F)ccc1-c1nc(-c2ccccc2O)n2ccccc12] | H | 321.30 |

TABLE 2-continued

Compounds of formula (I)

| No. | Structure | Mthd | Obs m/z M + H+ |
|---|---|---|---|
| 49 | 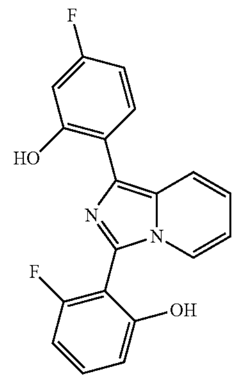 [SMILES: Oc1cc(F)ccc1-c1nc(-c2c(O)cccc2F)n2ccccc12] | H | 339/09 |
| 50 | 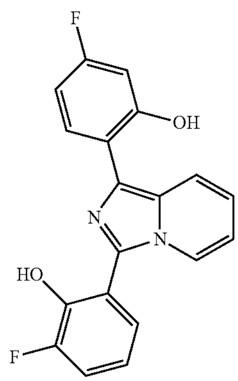 [SMILES: Oc1cc(F)ccc1-c1nc(-c2cccc(F)c2O)n2ccccc12] | H | 339.09 |
| 51 | 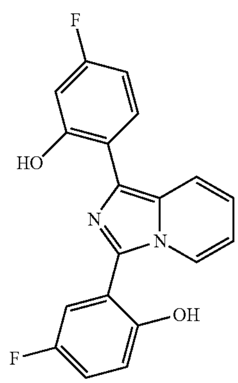 [SMILES: Oc1cc(F)ccc1-c1nc(-c2cc(F)ccc2O)n2ccccc12] | H | 339.09 |
| 52 | 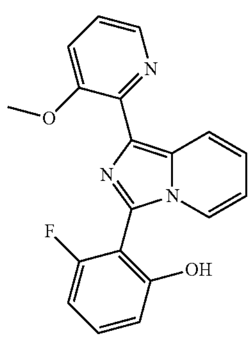 [SMILES: COc1cccnc1-c1nc(-c2c(O)cccc2F)n2ccccc12] | H | 336.11 |
| 53 | | H | 352.08 |
| 54 | | H | 336.11 |
| 55 | | H | 352.08 |
| 56 | | H | 336.11 |

TABLE 2-continued

Compounds of formula (I)

| No. | Structure | Mthd | Obs m/z M + H+ |
|---|---|---|---|
| 57 | 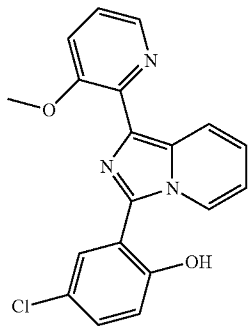 | H | 352.08 |
| 58 | 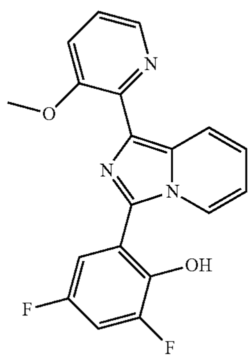 [SMILES: COc1cccnc1-c1nc(-c2cc(F)cc(F)c2O)n2ccccc12] | H | 354.10 |
| 59 | 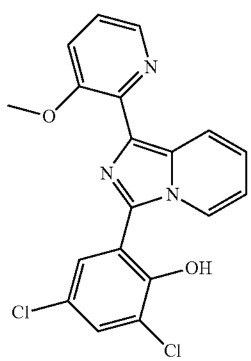 [SMILES: COc1cccnc1-c1nc(-c2cc(Cl)cc(Cl)c2O)n2ccccc12] | H | 386.05 |
| 60 | 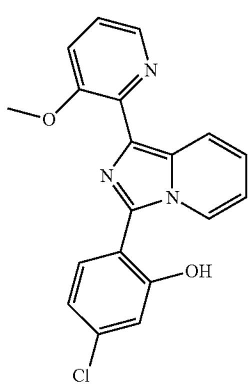 [SMILES: COc1cccnc1-c1nc(-c2ccc(Cl)cc2O)n2ccccc12] | H | 352.08 |
| 61 | | H | 332.14 |
| 62 | | H | 355.06 |
| 63 | | H | 355.06 |
| 64 | | H | 355.06 |

TABLE 2-continued
Compounds of formula (I)
| No. | Structure | Mthd | Obs m/z M + H+ |
|---|---|---|---|
| 65 | 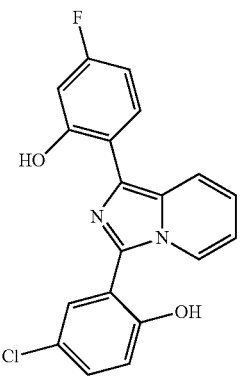 [SMILES: Oc1cc(F)ccc1-c1nc(-c2cc(Cl)ccc2O)n2ccccc12] | H | 355.06 |
| 66 | 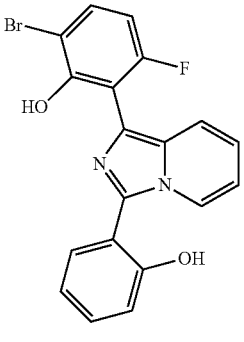 | H | 399.01 |
| 67 | 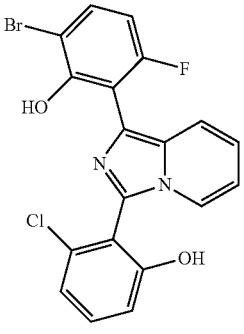 | H | 432.97 |
| 68 | 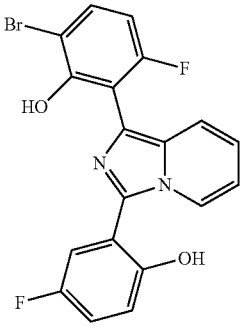 | H | 417.01 |
| 69 | 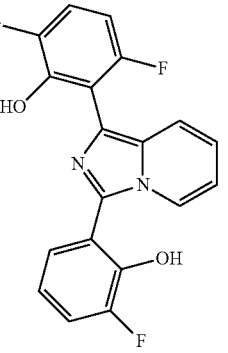 | H | 417.01 |
| 70 | 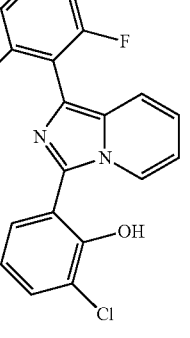 | H | 432.97 |
| 71 | 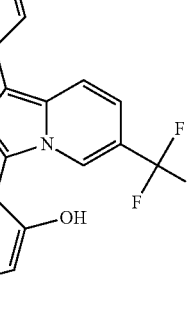 | H | 371.10 |
| 72 | 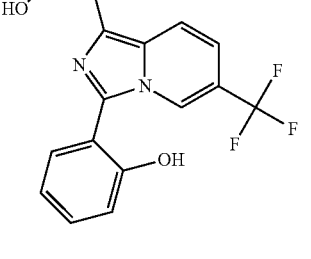 | H | 405.06 |

TABLE 2-continued

Compounds of formula (I)

| No. | Structure | Mthd | Obs m/z M + H⁺ |
|---|---|---|---|
| 73 | 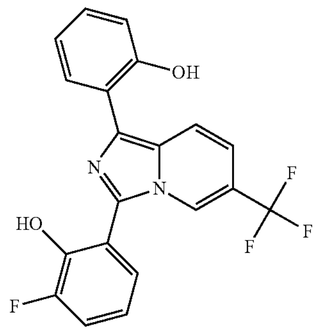 [SMILES: Oc1ccccc1-c1nc(-c2cccc(F)c2O)n2cc(C(F)(F)F)ccc12] | H | 389.09 |
| 74 | 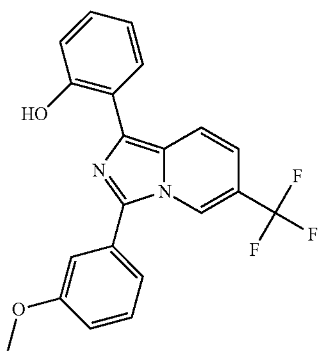 [SMILES: COc1cccc(-c2nc(-c3ccccc3O)c3ccc(C(F)(F)F)cn23)c1] | H | 385.12 |
| 75 | 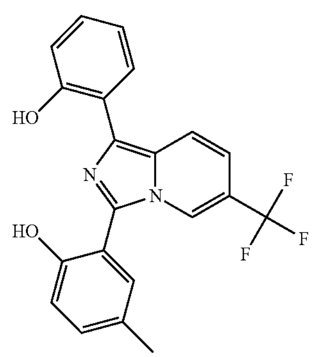 [SMILES: Cc1ccc(O)c(-c2nc(-c3ccccc3O)c3ccc(C(F)(F)F)cn23)c1] | H | 385.12 |
| 76 | 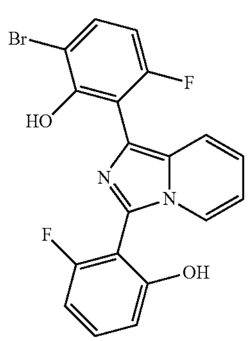 [SMILES: Oc1cccc(F)c1-c1nc(-c2c(F)ccc(Br)c2O)c2ccccn12] | H | 417.00 |
| 77 | | H | 332.10 |
| 78 | | H | 330.16 |
| 79 | | D | 322.10 |
| 80 | | D | 338.07 |

TABLE 2-continued
Compounds of formula (I)
| No. | Structure | Mthd | Obs m/z M + H+ |
|---|---|---|---|
| 81 | 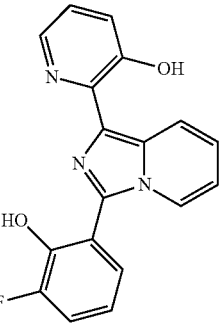 | D | 322.10 |
| 82 | 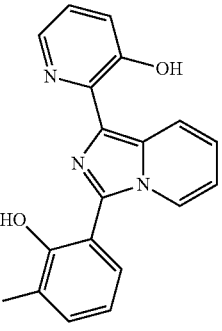 | D | 338.07 |
| 83 | 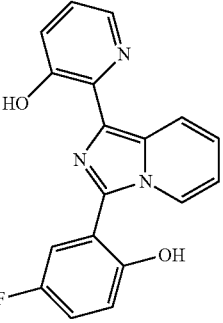 | D | 322.10 |
| 84 | 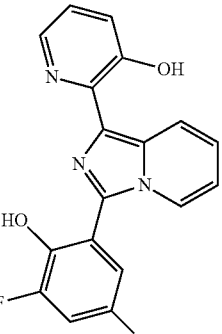 | D | 340.09 |
| 85 | 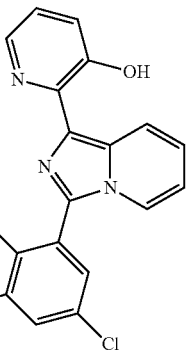 | D | 372.03 |
| 86 | 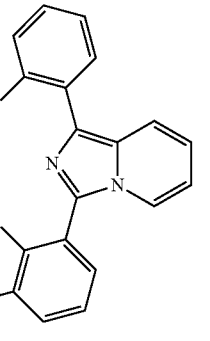 | H | 317.13 |
| 87 | 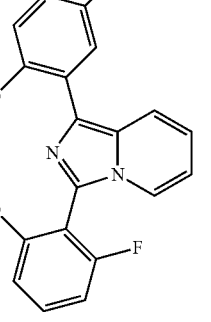 | H | 335.12 |
| 88 | 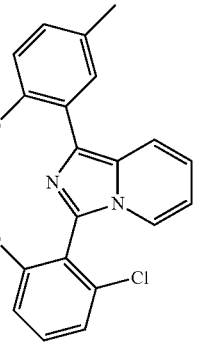 | H | 351.09 |

TABLE 2-continued

Compounds of formula (I)

| No. | Structure | Mthd | Obs m/z M + H+ |
|---|---|---|---|
| 89 | 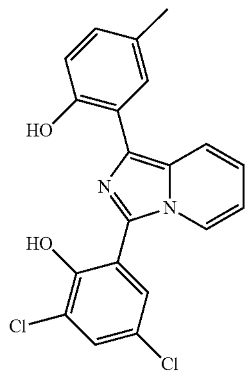 [SMILES: Cc1ccc(O)c(-c2nc(-c3cc(Cl)cc(Cl)c3O)n3ccccc23)c1] | H | 385.05 |
| 90 | 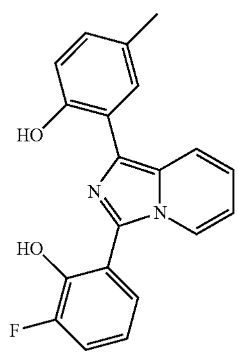 [SMILES: Cc1ccc(O)c(-c2nc(-c3cccc(F)c3O)n3ccccc23)c1] | H | 335.12 |
| 91 | 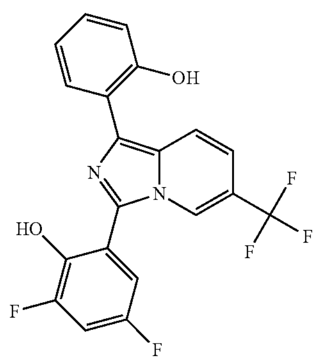 [SMILES: Oc1ccccc1-c1nc(-c2cc(F)cc(F)c2O)n2cc(C(F)(F)F)ccc12] | H | 407.08 |
| 92 | 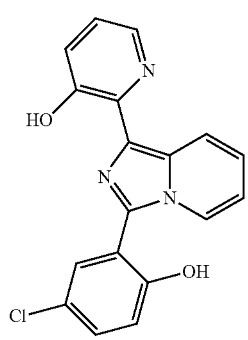 [SMILES: Oc1ccc(Cl)cc1-c1nc(-c2ncccc2O)c2ccccn12] | D | 338.07 |
| 93 | | D | 338.07 |
| 94 | | D | 318.12 |
| 95 | | D | 304.11 |
| 96 | | H | 405.06 |

TABLE 2-continued

Compounds of formula (I)

| No. | Structure | Mthd | Obs m/z M + H+ |
|-----|-----------|------|----------------|
| 97  |           | H    | 389.08         |
| 98  |           | H    | 389.08         |
| 99  |           | H    | 389.08         |
| 100 | 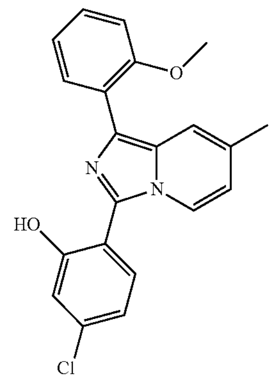 [SMILES: COc1ccccc1-c1nc(-c2ccc(Cl)cc2O)n2ccc(C)cc12]          | H    | 365.10         |
| 101 | 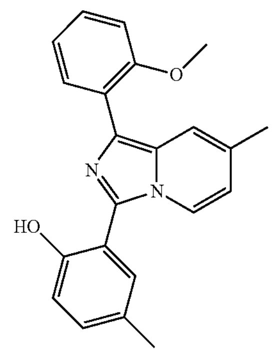 [SMILES: COc1ccccc1-c1nc(-c2cc(C)ccc2O)n2ccc(C)cc12]          | H    | 345.16         |
| 102 | 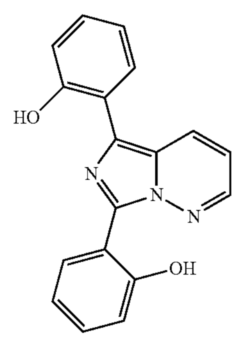 [SMILES: Oc1ccccc1-c1nc(-c2ccccc2O)n2ncccc12]          | H    | 304.11         |
| 103 | 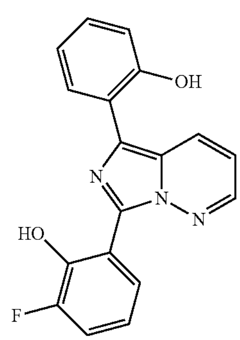 [SMILES: Oc1ccccc1-c1nc(-c2cccc(F)c2O)n2ncccc12]          | H    | 322.10         |

TABLE 2-continued

Compounds of formula (I)

| No. | Structure | Mthd | Obs m/z M + H+ |
|---|---|---|---|
| 104 | 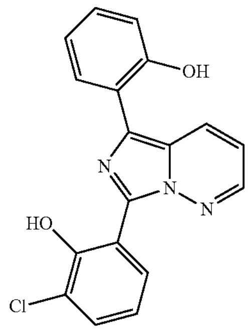 [SMILES: Oc1ccccc1-c1nc(-c2cccc(Cl)c2O)n2ncccc12] | H | 338.07 |
| 105 | 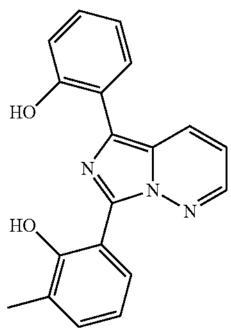 [SMILES: Cc1cccc(-c2nc(-c3ccccc3O)c3cccnn23)c1O] | H | 318.12 |
| 106 | 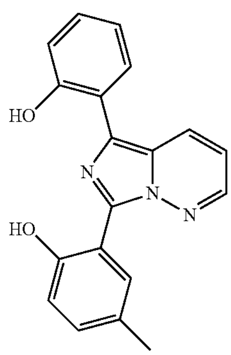 [SMILES: Cc1ccc(O)c(-c2nc(-c3ccccc3O)c3cccnn23)c1] | H | 318.12 |
| 107 | 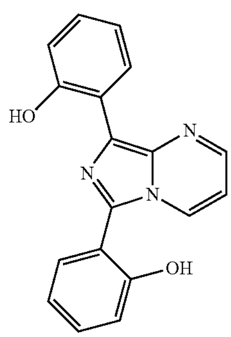 [SMILES: Oc1ccccc1-c1nc(-c2ccccc2O)n2cccnc12] | H | 304.11 |
| 108 | | H | 318.12 |
| 109 | | D | 331.15 |
| 110 | | H | 304.11 |
| 111 | | H | 322.10 |

TABLE 2-continued

Compounds of formula (I)

| No. | Structure | Mthd | Obs m/z M + H+ |
|---|---|---|---|
| 112 | 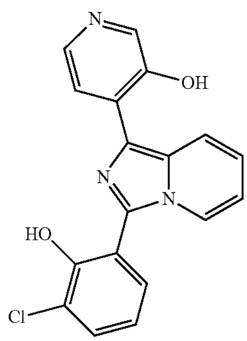 [SMILES: Oc1cnccc1-c1nc(-c2cccc(Cl)c2O)n2ccccc12] | H | 338.07 |
| 113 | 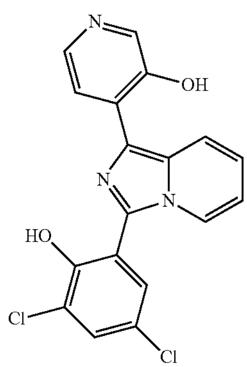 [SMILES: Oc1cnccc1-c1nc(-c2cc(Cl)cc(Cl)c2O)n2ccccc12] | H | 372.03 |
| 114 | 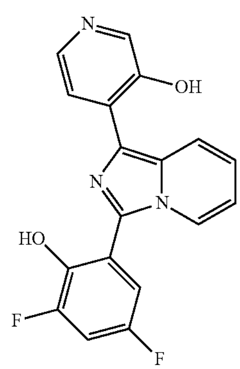 [SMILES: Oc1cnccc1-c1nc(-c2cc(F)cc(F)c2O)n2ccccc12] | H | 340.09 |
| 115 | 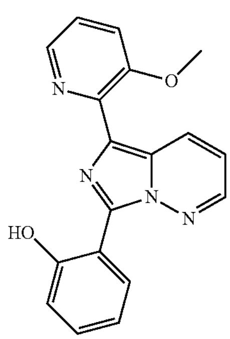 [SMILES: COc1cccnc1-c1nc(-c2ccccc2O)n2ncccc12] | H | 319.12 |
| 116 | | H | 337.11 |
| 117 | | H | 353.08 |
| 118 | | H | 333.13 |
| 119 | | H | 333.13 |

TABLE 2-continued

Compounds of formula (I)

| No. | Structure | Mthd | Obs m/z M + H+ |
|---|---|---|---|
| 120 | 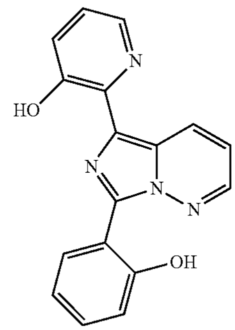 [SMILES: Oc1ccccc1-c1nc(-c2ncccc2O)c2cccnn12] | D | 305.10 |
| 121 | 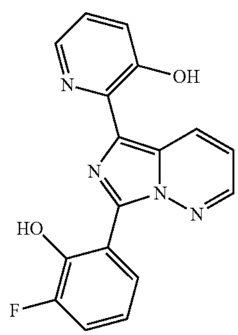 [SMILES: Oc1cccnc1-c1nc(-c2cccc(F)c2O)n2ncccc12] | D | 323.09 |
| 122 | 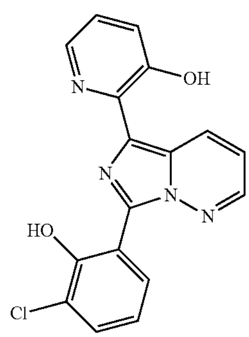 | D | 339.06 |
| 123 | 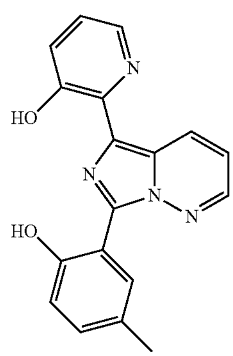 [SMILES: Cc1ccc(O)c(-c2nc(-c3ncccc3O)c3cccnn23)c1] | D | 319.12 |
| 124 | | H | 360.17 |
| 125 | | H | 318.13 |
| 126 | | D | 346.12 |
| 127 | | D | 322.07 |

TABLE 2-continued

Compounds of formula (I)

| No. | Structure | Mthd | Obs m/z M + H+ |
|---|---|---|---|
| 128 | 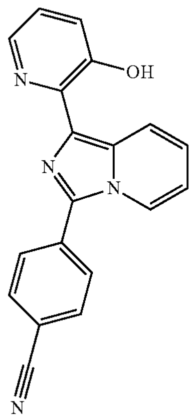 [SMILES: N#Cc1ccc(-c2nc(-c3ncccc3O)c3ccccn23)cc1] | D | 313.11 |
| 129 | 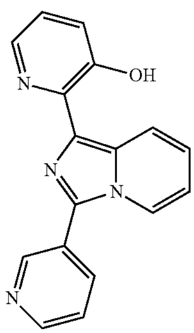 [SMILES: Oc1cccnc1-c1nc(-c2cccnc2)n2ccccc12] | D | 289.11 |
| 130 | 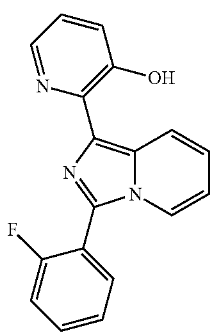 [SMILES: Oc1cccnc1-c1nc(-c2ccccc2F)n2ccccc12] | D | 306.10 |
| 131 | 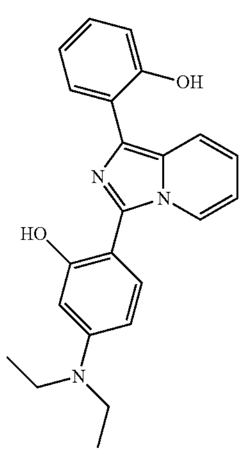 [SMILES: CCN(CC)c1ccc(-c2nc(-c3ccccc3O)c3ccccn23)c(O)c1] | H | 374.19 |
| 132 | | H | 318.12 |
| 133 | | H | 332.14 |
| 134 | | H | 352.08 |
| 135 | | H | 336.11 |

TABLE 2-continued

Compounds of formula (I)

| No. | Structure | Mthd | Obs m/z M + H+ |
|---|---|---|---|
| 136 | 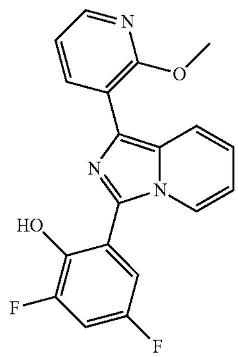 [SMILES: COc1ncccc1-c1nc(-c2cc(F)cc(F)c2O)n2ccccc12] | H | 354.10 |
| 137 | 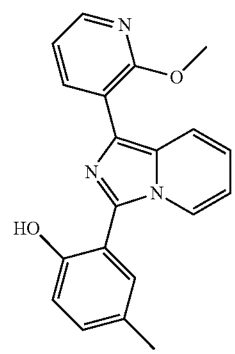 [SMILES: COc1ncccc1-c1nc(-c2cc(C)ccc2O)n2ccccc12] | H | 332.14 |
| 138 | 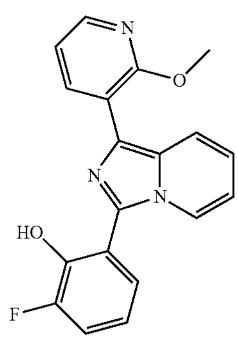 [SMILES: COc1ncccc1-c1nc(-c2cccc(F)c2O)n2ccccc12] | H | 336.11 |
| 139 | 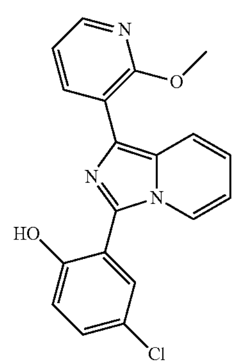 [SMILES: COc1ncccc1-c1nc(-c2cc(Cl)ccc2O)n2ccccc12] | H | 352.08 |
| 140 | | H | 352.08 |
| 141 | | D | 304.11 |
| 142 | | D | 318.12 |
| 143 | | D | 338.07 |

TABLE 2-continued

Compounds of formula (I)

| No. | Structure | Mthd | Obs m/z M + H+ |
|---|---|---|---|
| 144 | 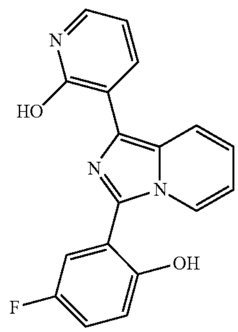 [SMILES: Oc1ccc(F)cc1-c1nc(-c2cccnc2O)c2ccccn12] | D | 322.10 |
| 145 | 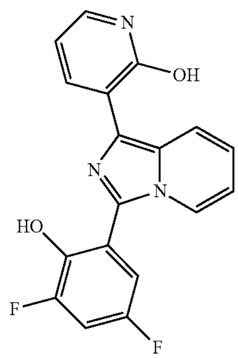 [SMILES: Oc1ncccc1-c1nc(-c2cc(F)cc(F)c2O)n2ccccc12] | D | 340.09 |
| 146 | 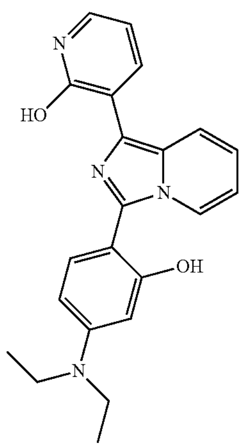 [SMILES: CCN(CC)c1ccc(-c2nc(-c3cccnc3O)c3ccccn23)c(O)c1] | D | 375.18 |
| 147 | 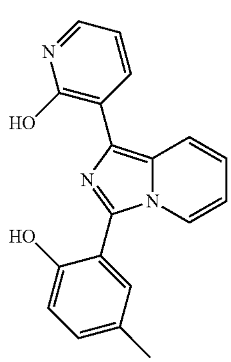 [SMILES: Cc1ccc(O)c(-c2nc(-c3cccnc3O)c3ccccn23)c1] | D | 318.12 |
| 148 | | D | 322.10 |
| 149 | | D | 338.07 |
| 150 | | D | 338.07 |
| 151 | | H | 336.11 |

TABLE 2-continued

Compounds of formula (I)

| No. | Structure | Mthd | Obs m/z M + H+ |
|---|---|---|---|
| 152 | 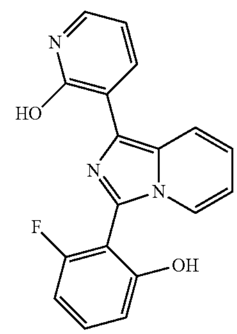 [SMILES: Oc1cccc(F)c1-c1nc(-c2cccnc2O)c2ccccn12] | D | 322.10 |
| 153 | 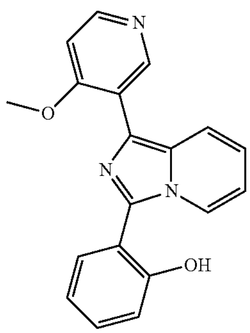 [SMILES: COc1ccncc1-c1nc(-c2ccccc2O)n2ccccc12] | H | 318.12 |
| 154 | 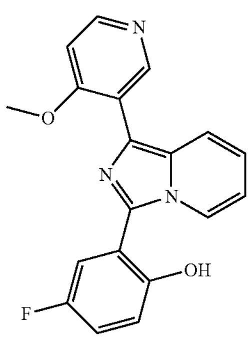 | H | 336.11 |
| 155 | 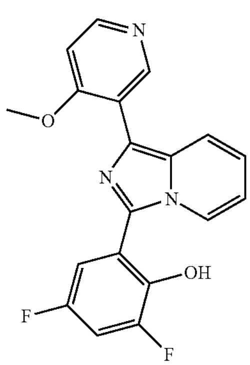 [SMILES: COc1ccncc1-c1nc(-c2cc(F)cc(F)c2O)n2ccccc12] | H | 354.11 |
| 156 | 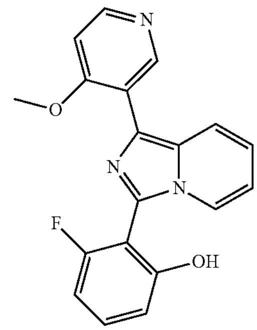 [SMILES: COc1ccncc1-c1nc(-c2c(O)cccc2F)n2ccccc12] | H | 336.11 |
| 157 | 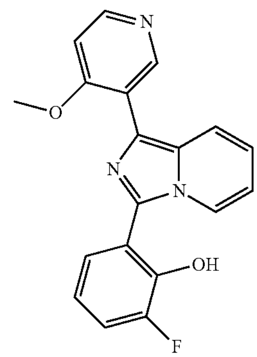 [SMILES: COc1ccncc1-c1nc(-c2cccc(F)c2O)n2ccccc12] | H | 336.11 |
| 158 | 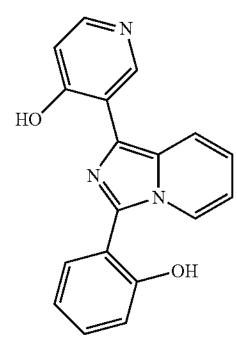 [SMILES: Oc1ccncc1-c1nc(-c2ccccc2O)n2ccccc12] | D | 304.11 |
| 159 | 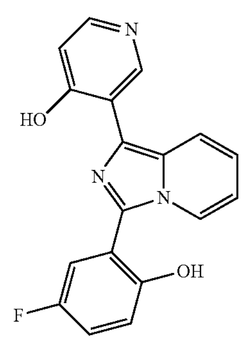 [SMILES: Oc1ccncc1-c1nc(-c2cc(F)ccc2O)n2ccccc12] | D | 322.10 |

TABLE 2-continued

Compounds of formula (I)

| No. | Structure | Mthd | Obs m/z M + H+ |
|---|---|---|---|
| 160 | 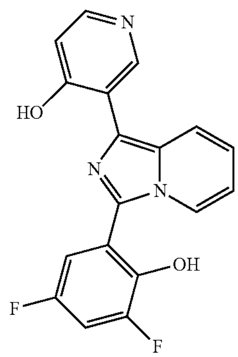 [SMILES: Oc1ccncc1-c1nc(-c2cc(F)cc(F)c2O)n2ccccc12] | D | 340.09 |
| 161 | 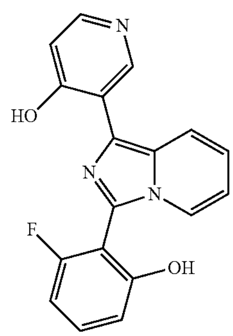 [SMILES: Oc1ccncc1-c1nc(-c2c(O)cccc2F)n2ccccc12] | D | 322.10 |
| 162 | 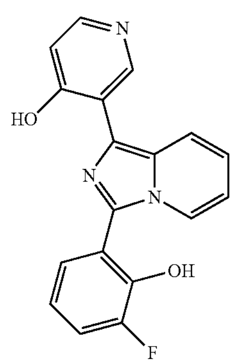 [SMILES: Oc1ccncc1-c1nc(-c2cccc(F)c2O)n2ccccc12] | D | 322.10 |
| 163 | 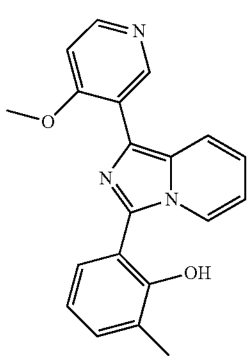 [SMILES: COc1ccncc1-c1nc(-c2cccc(C)c2O)n2ccccc12] | H | 332.14 |
| 164 | | H | 332.14 |
| 165 | | H | 352.08 |
| 166 | | H | 352.08 |
| 167 | | H | 386.05 |

TABLE 2-continued
Compounds of formula (I)
| No. | Structure | Mthd | Obs m/z M + H⁺ |
|---|---|---|---|
| 168 | 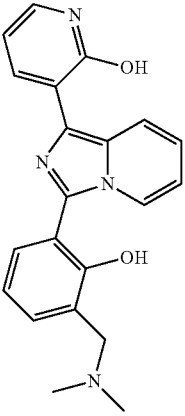 [SMILES: CN(C)Cc1cccc(-c2nc(-c3cccnc3O)c3ccccn23)c1O] | D | 361.17 |
| 169 | 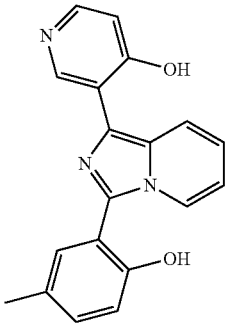 [SMILES: Cc1ccc(O)c(-c2nc(-c3cnccc3O)c3ccccn23)c1] | D | 318.12 |
| 170 | 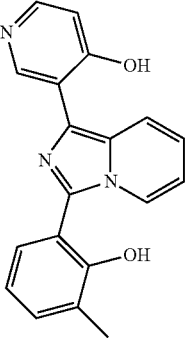 [SMILES: Cc1cccc(-c2nc(-c3cnccc3O)c3ccccn23)c1O] | D | 318.12 |
| 171 | 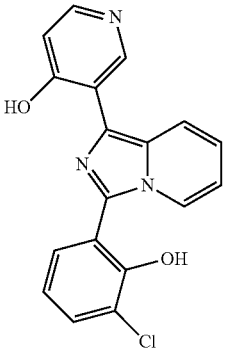 [SMILES: Oc1ccncc1-c1nc(-c2cccc(Cl)c2O)n2ccccc12] | D | 338.07 |
| 172 | 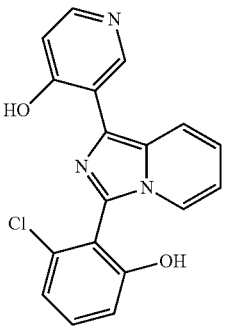 | D | 338.07 |
| 173 | 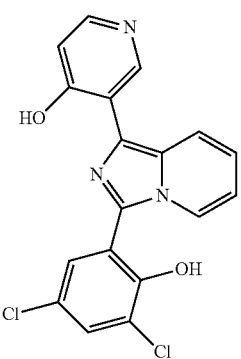 [SMILES: Oc1ccncc1-c1nc(-c2cc(Cl)cc(Cl)c2O)n2ccccc12] | D | 372.03 |
| 174 | 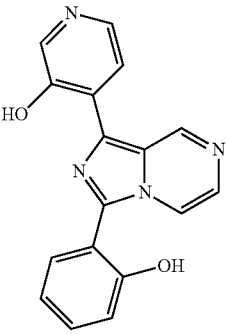 [SMILES: Oc1cnccc1-c1nc(-c2ccccc2O)n2ccncc12] | H | 305.10 |
| 175 | 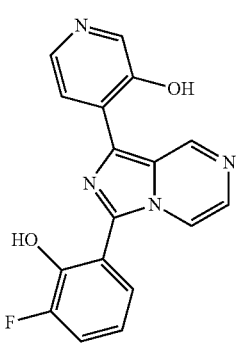 [SMILES: Oc1cnccc1-c1nc(-c2cccc(F)c2O)n2ccncc12] | H | 323.09 |

TABLE 2-continued

Compounds of formula (I)

| No. | Structure | Mthd | Obs m/z M + H+ |
|---|---|---|---|
| 176 | 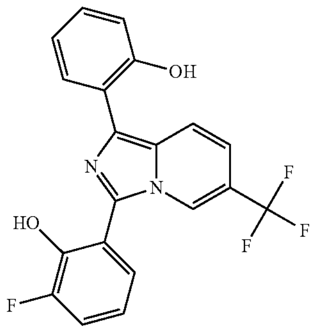 [SMILES: Oc1ccccc1-c1nc(-c2cccc(F)c2O)n2cc(C(F)(F)F)ccc12] | H | 339.06 |
| 177 | 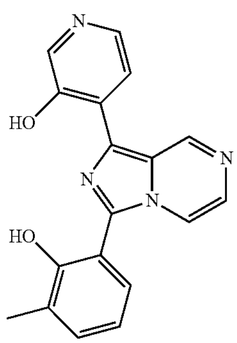 [SMILES: Cc1cccc(-c2nc(-c3ccncc3O)c3cnccn23)c1O] | H | 319.12 |
| 178 | 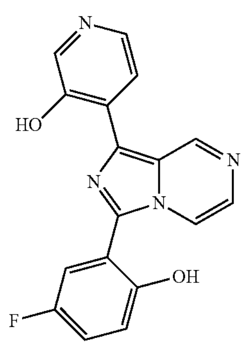 [SMILES: Oc1cnccc1-c1nc(-c2cc(F)ccc2O)n2ccncc12] | H | 323.09 |
| 179 | 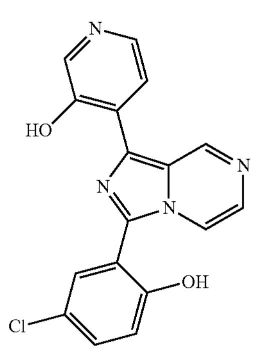 [SMILES: Oc1cnccc1-c1nc(-c2cc(Cl)ccc2O)n2ccncc12] | H | 339.06 |
| 180 | | H | 319.12 |
| 181 | | H | 305.10 |
| 182 | | H | 319.12 |
| 183 | | H | 323.09 |

TABLE 2-continued

Compounds of formula (I)

| No. | Structure | Mthd | Obs m/z M + H+ |
|---|---|---|---|
| 184 | (structure with pyridine, imidazopyridazine, chlorophenol, OH) | H | 339.06 |
| 185 | (structure with pyridine, imidazopyrimidine, phenol) | H | 305.10 |
| 186 | (structure with pyridine, imidazopyrimidine, methylphenol) | H | 319.12 |

Biological Assays

Method I: Measurement of Fe Efflux from Cells

Compounds of the current invention were assessed for their ability to efflux iron (Fe) from a cell using the following protocol.

The human neuroblastoma line BE(2)-M17 (M17) cell cultures were acquired from Sigma Aldrich (Catalogue #: 95011816). M17 Cells were maintained in Opti-MEM reduced serum media supplemented with 10% fetal bovine serum (Bovogen, SFBSF) and passaged twice weekly. Cells were cultured at 37° C. in the presence of 5% $CO_2$. Culture supplies were sourced from Thermo Fisher unless otherwise stated.

A solution of $^{57}$Fe cold isotope was prepared by dissolving $^{57}$Fe metal (>95% enrichment, Trace Sciences International) in concentrated HCl to give a final concentration of 573 mM. From this master solution, a 10 mM working solution was prepared in sterile water. The working solution was used within two months of preparation.

M17 cells were loaded with iron initially by seeding into 48-well plates at a density of $0.15 \times 10^6$ cells per well in 0.5 mL media. After 48 h, old media was discarded. Fresh media was supplemented with 20 µM $^{57}$Fe isotope, from the 10 mM $^{57}$Fe working solution. Cells received 0.2 mL of this $^{57}$Fe enriched media and were returned to the incubator for 20 h. The ability of experimental compounds to efflux iron was determined by the dissolution of compounds in DMSO and diluted in Hanks' Balanced Salt Solution (HBSS) for treatment of M17 cells. After $^{57}$Fe incubation, cells were rinsed twice with HBSS and treated with 0.15 mL trial compound for 2 h at a concentration of 20 µM. All assays included a relevant vehicle (0.4%-0.8% DMSO) as well as a positive control (20 µM). Following the treatment period, 0.1 mL of media was collected from cells and the extracellular $^{57}$Fe content was analysed via inductively coupled mass spectrometry (ICP-MS, Agilent 7700x series instrument).

To perform this protocol the following supplies were purchased from Sigma Aldrich: anhydrous dimethyl sulfoxide (DMSO, Catalogue #: 276855), Hanks' Balanced Salt Solution supplemented with 20 mM HEPES and 4.2 mM Sodium Bicarbonate (HBSS, pH: 7.4, Catalogue #: H1387).

The ability of the compounds of the invention to efflux Fe from a cell was determined using the above protocol hence cells having been pre-treated with Fe in the media for 24 h were subsequently washed and treated with fresh, Fe free media either with or without the compound (20 µM). After 2 h the Fe levels in the media were measured and the increase determined as a percentage increase relative to the cell media in the absence of the compound.

$$\% \text{ Fe efflux} = \frac{([\text{Fe in media}]_{Compound} - [\text{Fe in media}]_{No\ Compound})}{[\text{Fe in media}]_{No\ Compound}} \times 100$$

Representative data is provided in Table 3 where the % Fe efflux for the specified compounds of the invention lie in the following ranges: A<30%, B 30-100%, C 100-150%; D>150%

TABLE 3

% Fe efflux of selected compounds from Table 2

| No. | % Fe Efflux Range |
|---|---|
| 3 | B |
| 4 | D |
| 6 | A |
| 7 | A |
| 10 | B |
| 16 | A |
| 17 | A |
| 18 | B |
| 20 | A |
| 21 | A |
| 22 | B |
| 23 | A |
| 24 | A |
| 25 | A |
| 27 | A |
| 29 | A |
| 31 | A |
| 32 | B |
| 33 | A |
| 34 | B |
| 35 | A |
| 37 | A |
| 38 | B |

TABLE 3-continued

% Fe efflux of selected compounds from Table 2

| No. | % Fe Efflux Range |
|---|---|
| 39 | B |
| 40 | B |
| 41 | B |
| 42 | B |
| 43 | B |
| 44 | B |
| 46 | A |
| 49 | A |
| 50 | B |
| 51 | A |
| 52 | A |
| 56 | B |
| 59 | A |
| 61 | B |
| 63 | A |
| 77 | A |
| 79 | C |
| 80 | B |
| 81 | D |
| 82 | B |
| 83 | C |
| 84 | D |
| 85 | B |
| 87 | A |
| 92 | C |
| 93 | B |
| 94 | B |
| 95 | B |
| 98 | A |
| 100 | A |
| 102 | A |
| 103 | B |
| 104 | A |
| 107 | B |
| 108 | A |
| 110 | D |
| 111 | C |
| 112 | C |
| 114 | C |
| 120 | C |
| 121 | D |
| 122 | D |
| 123 | D |
| 124 | D |
| 125 | A |
| 126 | A |
| 127 | A |
| 130 | A |
| 141 | C |
| 142 | B |
| 143 | A |
| 144 | C |
| 145 | C |
| 146 | B |
| 147 | C |
| 148 | B |
| 149 | B |
| 150 | B |
| 152 | B |
| 153 | A |
| 154 | A |
| 155 | A |
| 156 | A |
| 157 | A |
| 158 | B |
| 159 | B |
| 160 | B |
| 161 | B |
| 162 | B |
| 163 | A |
| 168 | A |
| 169 | B |
| 171 | B |
| 172 | B |
| 174 | D |

TABLE 3-continued

% Fe efflux of selected compounds from Table 2

| No. | % Fe Efflux Range |
|---|---|
| 175 | D |
| 176 | D |
| 177 | D |
| 178 | D |
| 179 | D |
| 180 | D |
| 181 | C |
| 182 | B |
| 185 | C |
| 186 | B |

The present invention includes embodiments outlined in the following clauses:

1. A compound of formula (I):

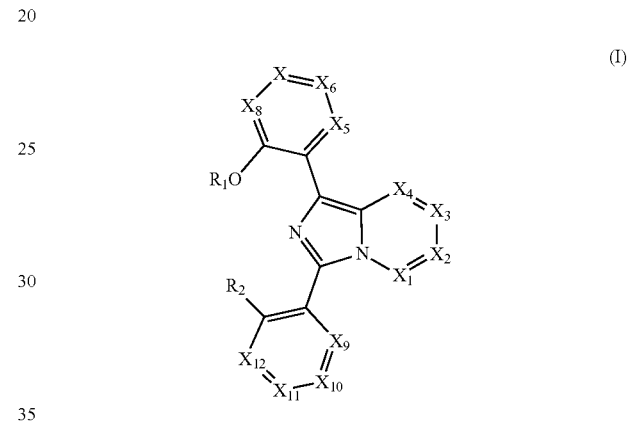

wherein each of $X_1$ to $X_{12}$ are independently N or $CR_3$, wherein 0, 1, 2 or 3 of $X_1$ to $X_{12}$ are N;

$R_1$ is selected from the group consisting of hydrogen, alkyl, alkenyl, alkynyl, $C(O)R_4$ and $C(S)R_4$;

$R_2$ is selected from the group consisting of hydrogen, OH, SH, halo, $OR_5$, $SR_5$, $C(O)R_4$, $C(S)R_4$, $NO_2$, CN, $N(R_6)_2$, $OS(O)_mN(R_6)_2$ and $OS(O)_nR_4$;

each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OH, $(C(R_7)_2)_m$SH, $(C(R_7)_2)_m$OR_5$, $(C(R_7)_2)_m$SR_5$, $(C(R_7)_2)_m$C(O)R_4$, $(C(R_7)_2)_m$C(S)R_4$, $(C(R_7)_2)_m$OC(O)R_4$, $(C(R_7)_2)_m$SC(S)R_4$, $(C(R_7)_2)_m$OC(S)R_4$, $(C(R_7)_2)_m$SC(O)R_4$, $(C(R_7)_2)_m$CN, $(C(R_7)_2)_m$NO_2$, $(C(R_7)_2)_m$N(R_6)_2$, $(C(R_7)_2)_m$S(O)_nR_4$, $(C(R_7)_2)_m$N(R_6)C(O)N(R_6)_2$ and $(C(R_7)_2)_m$N(R_6)C(S)N(R_6)_2$;

$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;

$R_5$ is selected from the group consisting of hydrogen, alkyl, alkenyl, alkynyl, haloalkyl, cycloalkyl, cycloalkenyl, aryl, heterocyclyl, heteroaryl C(O)alkyl, C(O)alkenyl, C(O)alkynyl, $S(O)_nR_4$ and $S(O)_nN(R_6)_2$;

$R_6$ is selected from the group consisting of hydrogen, alkyl, alkenyl, alkynyl, haloalkyl, cycloalkyl, cycloalkenyl, aryl, heterocyclyl and heteroaryl; each $R_7$ is selected from the group consisting of hydrogen, alkyl, alkenyl, alkynyl and haloalkyl;

m is 0 or an integer from 1 to 6;

n is 1 or 2;

wherein each alkyl, alkenyl, alkynyl, cycloalkyl, cycloalkenyl, aryl, heterocyclyl and heteroaryl is optionally substituted;

or a pharmaceutically acceptable salt or solvate thereof with the proviso that when $R_1$ is methyl, $X_1$, $X_2$, $X_3$, $X_4$, $X_5$, $X_6$, $X_8$, $X_9$, $X_{10}$, $X_{11}$ and $X_{12}$ are each $CR_3$ where $R_3$ is hydrogen and $X_7$ is $CR_3$ where $R_3$ is $OCH_3$, $R_2$ is not hydrogen.

2. A compound according to clause 1 wherein $X_1$ to $X_{12}$ are independently selected from $CR_3$.

3. A compound according to clause 1 wherein one of $X_1$ to $X_{12}$ is N and the remainder are $CR_3$.

4. A compound according to clause 1 wherein two of $X_1$ to $X_{12}$ are N and the remainder are $CR_3$.

5. A compound according to clause 1 wherein three of $X_1$ to $X_{12}$ are N and the remainder are $CR_3$.

6. A compound according to any one of clauses 1 and 3 to 5 wherein one of the following applies:

i) one of $X_1$ to $X_4$ is N;

ii) one of $X_5$ to $X_8$ is N;

iii) one of $X_9$ to $X_{12}$ is N;

iv) one of $X_1$, $X_4$, $X_5$, $X_6$, $X_7$, $X_8$, $X_9$ and $X_{11}$ is N;

v) two of $X_1$, $X_3$, $X_4$, $X_5$, $X_9$ and $X_{10}$ are N;

vi) one of $X_1$ to $X_4$ and one of $X_5$ to $X_8$ are N;

vii) one of $X_1$ to $X_4$ and one of $X_9$ to $X_{12}$ are N;

viii) one of $X_5$ to $X_8$ and one of $X_9$ to $X_{12}$ are N;

ix) $X_1$ and $X_5$, $X_1$ and $X_7$, $X_3$ and $X_7$, $X_4$ and $X_7$ or $X_5$ and $X_{10}$ are N;

x) one of $X_1$ to $X_4$, one of $X_5$ to $X_8$ and one of $X_9$ to $X_{12}$ are N;

xi) one of $X_1$ to $X_4$ and two of $X_5$ to $X_8$ are N;

xii) two of $X_5$ to $X_8$ are N and one of $X_9$ to $X_{12}$ are N; or xiii) three of $X_1$, $X_5$, $X_7$ and $X_9$ are N.

7. A compound according to any one of clauses 1 to 6 wherein $R_1$ is selected from the group consisting of hydrogen, $C_{1-6}$alkyl, $C_{2-6}$ alkenyl, $C(O)C_{1-6}$ alkyl and $C(O)OC_{1-6}$ alkyl.

8. A compound according to any one of clauses 1 to 7 wherein $R_2$ is selected from hydrogen, OH, SH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$ alkyl), $OS(O)_2N(C_{1-6}$alkyl$)_2$ and $OS(O)_nC_{1-6}$alkyl.

9. A compound according to any one of clauses 1 to 8 wherein each $R_3$ is independently selected from the group consisting of hydrogen, halo, $C_{1-6}$ alkyl, $C_{2-6}$ alkenyl, $C_{1-6}$ haloalkyl, cycloalkyl, cycloalkenyl, aryl, heterocyclyl, heteroaryl, OH, SH, $CH_2OH$, $CH_2SH$, $OC_{1-6}$ alkyl, $SC_{1-6}$ alkyl, $CH_2OC_{1-6}$ alkyl, $CH_2SC_{1-6}$ alkyl, $OC(O)C_{1-6}$ alkyl, $CH_2OC(O)C_{1-6}$ alkyl, $C(O)C_{1-6}$ alkyl, $CO_2H$, $CH_2CO_2H$, $CH_2C(O)C_{1-6}$ alkyl, $C(O)OC_{1-6}$ alkyl, $CH_2C(O)OC_{1-6}$ alkyl, $CONH_2$, $CH_2CONH_2$, CN, $CH_2CN$, $NO_2$, $CH_2NO_2$, $NH_2$, $NH(C_{1-6}$ alkyl), $N(C_{1-6}$ alkyl$)_2$, $CH_2NH_2$, $CH_2NH(C_{1-6}$ alkyl), $CH_2N(C_{1-6}$ alkyl$)_2$, $SO_2H$, $CH_2S(O)_2H$, $SO_3H$, $CH_2SO_3H$, $S(O)_2C_{1-6}$ alkyl, $CH_2S(O)_2C_{1-6}$ alkyl, $S(O)_2OC_{1-6}$ alkyl, $CH_2S(O)_2OC_{1-6}$ alkyl, $S(O)_2NH_2$, $S(O)_nNH(C_{1-6}$ alkyl), $S(O)_2N(C_{1-6}$ alkyl$)_2$, $CH_2S(O)_2NH_2$, $CH_2S(O)_nNH(C_{1-6}$alkyl), $CH_2S(O)_2N(C_{1-6}$alkyl$)_2$, $NHC(O)NH_2$, $NHC(O)NH(C_{1-6}$ alkyl), $NHC(O)N(C_{1-6}$ alkyl$)_2$ $CH_2NHC(O)NH_2$, $CH_2NHC(O)NH(C_{1-6}$ alkyl) and $CH_2NHC(O)N(C_{1-6}$ alkyl$)_2$.

10. The compound according to clause 1 which is a compound of formula (II):

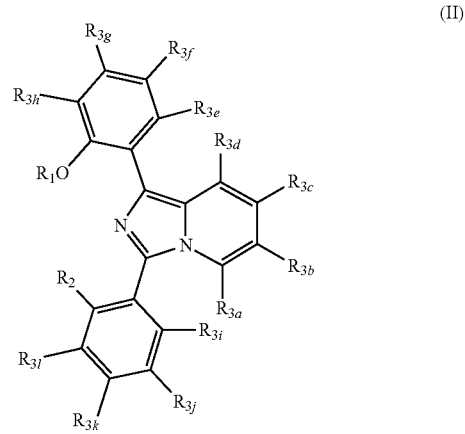

(II)

wherein $R_1$ and $R_2$ are as defined for formula (I) in claim 1 and $R_{3a}$ to $R_{3l}$ are each independently selected from the group consisting hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$, wherein $R_4$, $R_5$, $R_6$, $R_7$ and m are as defined for formula (I) in claim 1;

or a pharmaceutically acceptable salt or solvate thereof;

with the proviso that when $R_1$ is methyl, $R_{3a}$, $R_{3b}$, $R_{3c}$, $R_{3d}$, $R_{3e}$, $R_{3f}$, $R_{3h}$, $R_{3i}$, $R_{3j}$, $R_{3k}$ and $R_{3l}$ are each hydrogen and $R_{3g}$ is $OCH_3$, $R_2$ is not hydrogen.

11. The compound according to clause 1 which is a compound of formula (III):

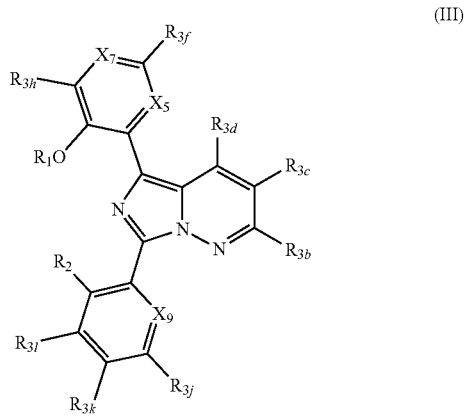

(III)

wherein $X_5$ is N or $CR_{3e}$; $X_7$ is N or $CR_{3g}$; $X_9$ is N or $CR_{3i}$; wherein none, one or two of $X_5$, $X_7$ and $X_9$ is N;

$R_1$ and $R_2$ are as defined for formula (I) in claim 1 and $R_{3b}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)$ $R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

12. The compound according to clause 1 which is a compound of formula (IV):

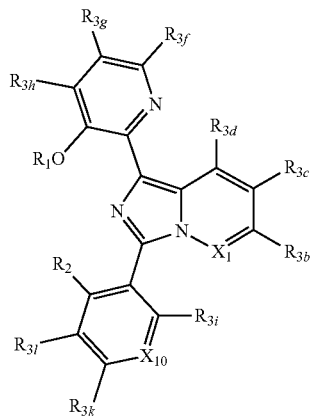

(IV)

wherein $X_1$ is N or $CR_{3a}$; $X_{10}$ is N or $CR_{3j}$;

$R_1$ and $R_2$ are as defined for formula (I) in claim 1 and $R_{3a}$ to $R_{3d}$ and $R_{3f}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_5$, $R_6$, $R_7$ and m are as defined for formula (I) in claim 1; or a pharmaceutically acceptable salt or solvate thereof.

13. The compound according to clause 1 which is a compound of formula (V):

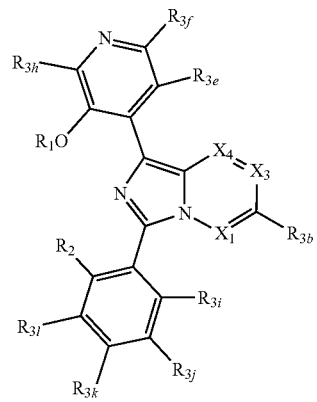

(V)

wherein $X_1$ is N or $CR_{3a}$; $X_3$ is N or $CR_{3c}$; $X_4$ is N or $CR_{3d}$; wherein none, one or two of $X_1$, $X_3$ and $X_4$ is N;

$R_1$ and $R_2$ are as defined for formula (I) in claim 1 and $R_{3a}$ to $R_{3f}$ and $R_{3h}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

14. The compound according to clause 1 which is a compound of formula (VI):

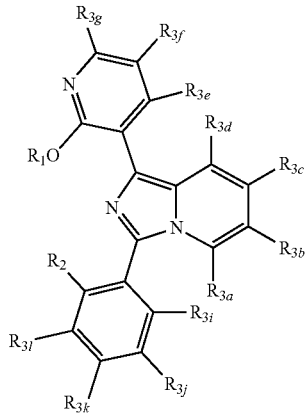

(VI)

wherein $R_1$ and $R_2$ are as defined for formula (I) in claim 1 and $R_{3a}$ to $R_{3g}$ and $R_{3i}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

15. The compound according to clause 1 which is a compound of formula (VII):

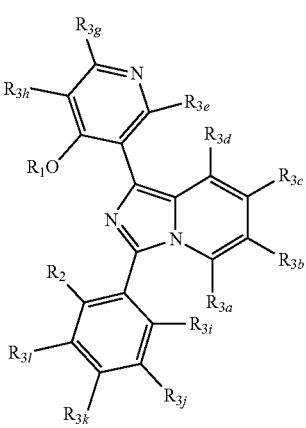

(VII)

wherein $R_1$ and $R_2$ are as defined for formula (I) in claim 1 and $R_{3a}$ to $R_{3e}$ and $R_{3g}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$, wherein $R_4$, $R_5$, $R_6$, $R_7$ and m are as defined for formula (I) in claim 1;

or a pharmaceutically acceptable salt or solvate thereof.

16. The compound according to clause 1 which is a compound of formula (VIII):

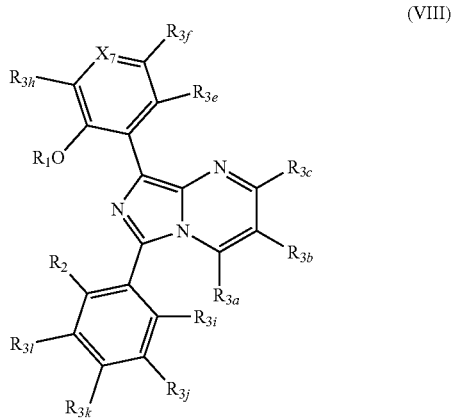

(VIII)

wherein $X_7$ is N or CR$_{3g}$, $R_1$ and $R_2$ are as defined for formula (I) in claim 1 and $R_{3a}$ to $R_{3c}$ and $R_{3e}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$, wherein $R_4$, $R_5$, $R_6$, $R_7$ and m are as defined for formula (I) in claim 1;

or a pharmaceutically acceptable salt or solvate thereof.

17. The compound according to clause 1 which is a compound of formula (IX):

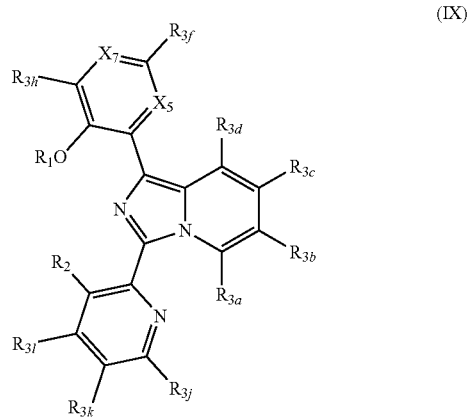

(IX)

Wherein $X_5$ is N or CR$_{3e}$; $X_7$ is N or CR$_{3g}$; $R_1$ and $R_2$ are as defined for formula (I) in claim 1 and $R_{3a}$ to $R_{3h}$ and $R_{3j}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$, wherein $R_4$, $R_5$, $R_6$, $R_7$ and m are as defined for formula (I) in claim 1;

or a pharmaceutically acceptable salt or solvate thereof.

18. The compound according to clause 1 which is a compound of formula (X):

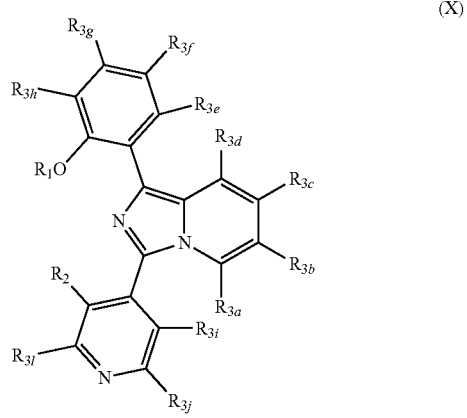

(X)

wherein $R_1$ and $R_2$ are as defined for formula (I) in claim 1 and $R_{3a}$ to $R_{3j}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$, wherein $R_4$, $R_5$, $R_6$, $R_7$ and m are as defined for formula (I) in claim 1;

or a pharmaceutically acceptable salt or solvate thereof.

19. The compound according to clause 1 which is a compound of formula (XI):

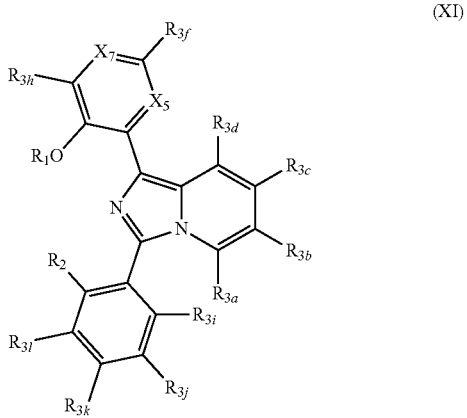

(XI)

wherein $X_5$ is N and $X_7$ is $CR_{3g}$; or $X_5$ is $CR_{3e}$ and $X_7$ is N; $R_1$ and $R_2$ are as defined for formula (I) in claim 1 and $R_{3a}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

20. A compound according to clause 19 wherein $X_5$ is N.

21. A compound according to clause 19 wherein $X_7$ is N.

22. A pharmaceutical composition comprising a compound of formula (I) according to any one of clauses 1 to 21 or a pharmaceutically acceptable salt or solvate thereof and a pharmaceutically acceptable carrier and/or excipient.

23. A method of treating or preventing a metal ion associated disorder comprising administering to a subject a compound of formula (I) according to any one of clauses 1 to 21 or a pharmaceutically acceptable salt or solvate thereof.

24. The method according to clause 23 wherein the metal ion associated disorder is an iron ion associated disorder.

25. A method according to clause 23 or clause 24 wherein the disorder is a neurological disorder.

26. A compound of formula (I) according to any one of clauses 1 to 21 or a pharmaceutically acceptable salt or solvate thereof for use in treating or preventing a metal ion associated disorder.

27. A compound of formula (I) for use according to clause 26 wherein the metal ion associated disorder is an iron ion associated disorder.

28. A compound of formula (I) for use according to clause 26 or clause 27 wherein the disorder is a neurological disorder.

29. Use of a compound of formula (I) according to any one of clauses 1 to 21 or a pharmaceutically acceptable salt or solvate thereof in the manufacture of a medicament for treating or preventing metal ion associated disorder.

30. Use of a compound of formula (I) according to clause 29 wherein the metal ion associated disorder is an iron ion associated disorder.

31. Use according to clause 29 or clause 30 wherein the disorder is a neurological disorder.

The claims defining the invention are as follows:

1. A compound of formula (I):

wherein
each of $X_1$, $X_2$, $X_3$, $X_4$, $X_5$, $X_6$, $X_7$, $X_8$, $X_9$, $X_{10}$, $X_{11}$ and $X_{12}$ are independently N or $CR_3$, wherein 0, 1, 2 or 3 of $X_1$, $X_2$, $X_3$, $X_4$, $X_5$, $X_6$, $X_7$, $X_8$, $X_9$, $X_{10}$, $X_{11}$ and $X_{12}$ are N;

$R_1$ is selected from the group consisting of hydrogen, alkyl, alkenyl, alkynyl, $C(O)R_4$ and $C(S)R_4$;

$R_2$ is selected from the group consisting of OH, SH, halo, $OR_5$, $SR_5$, $C(O)R_4$, $C(S)R_4$, $NO_2$, CN, $N(R_6)_2$, $OS(O)_n N(R_6)_2$ and $OS(O)_n R_4$;

each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R)_2)_m$aryl, $(C(R_7)_2)_m$heterocyclyl, $(C(R_7)_2)_m$heteroaryl, $(C(R_7)_2)_m OH$, $(C(R_7)_2)_m SH$, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$;

$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;

$R_5$ is selected from the group consisting of hydrogen, alkyl, alkenyl, alkynyl, haloalkyl, cycloalkyl, cycloalkenyl, aryl, heterocyclyl, heteroaryl C(O)alkyl, C(O)alkenyl, C(O)alkynyl, $S(O)_n R_4$ and $S(O)_n N(R_6)_2$;

$R_6$ is selected from the group consisting of hydrogen, alkyl, alkenyl, alkynyl, haloalkyl, cycloalkyl, cycloalkenyl, aryl, heterocyclyl and heteroaryl; each $R_7$ is selected from the group consisting of hydrogen, alkyl, alkenyl, alkynyl and haloalkyl;

m is 0 or an integer from 1 to 6;

n is 1 or 2;

wherein each alkyl, alkenyl, alkynyl, cycloalkyl, cycloalkenyl, aryl, heterocyclyl and heteroaryl is optionally substituted;

or a pharmaceutically acceptable salt or solvate thereof.

2. A compound according to claim 1 wherein $X_1$, $X_2$, $X_3$, $X_4$, $X_5$, $X_6$, $X_7$, $X_8$, $X_9$, $X_{10}$, $X_{11}$ and $X_{12}$ are independently selected from $CR_3$.

3. A compound according to claim 1 wherein one of $X_1$, $X_2$, $X_3$, $X_4$, $X_5$, $X_6$, $X_7$, $X_8$, $X_9$, $X_{10}$, $X_{11}$ and $X_{12}$ is N and the remainder are $CR_3$.

4. A compound according to claim 1 wherein two of $X_1$, $X_2$, $X_3$, $X_4$, $X_5$, $X_6$, $X_7$, $X_8$, $X_9$, $X_{10}$, $X_{11}$ and $X_{12}$ are N and the remainder are $CR_3$.

5. A compound according to claim 1 wherein three of $X_1$, $X_2$, $X_3$, $X_4$, $X_5$, $X_6$, $X_7$, $X_8$, $X_9$, $X_{10}$, $X_{11}$ and $X_{12}$ are N and the remainder are $CR_3$.

6. A compound according to claim 1 wherein one of the following applies:
   i) one of $X_1$, $X_2$, $X_3$ and $X_4$ is N;
   ii) one of $X_5$, $X_6$, $X_7$ and $X_8$ is N;
   iii) one of $X_9$, $X_{10}$, $X_{11}$ and $X_{12}$ is N;
   iv) one of $X_1$, $X_4$, $X_5$, $X_6$, $X_7$, $X_8$, $X_9$ and $X_{10}$ is N;
   v) two of $X_1$, $X_3$, $X_4$, $X_5$, $X_9$ and $X_{10}$ are N;
   vi) one of $X_1$, $X_2$, $X_3$ and $X_4$ and one of $X_5$, $X_6$, $X_7$ and $X_8$ are N;
   vii) one of $X_1$, $X_2$, $X_3$ and $X_4$ and one of $X_9$, $X_{10}$, $X_{11}$ and $X_{12}$ are N;
   viii) one of $X_5$, $X_6$, $X_7$ and $X_8$ and one of $X_e$, $X_{10}$, $X_{11}$ and $X_{12}$ are N;
   ix) $X_1$ and $X_5$, $X_1$ and $X_7$, $X_3$ and $X_7$, $X_4$ and $X_7$ or $X_5$ and $X_{10}$ are N;
   x) one of $X_1$, $X_2$, $X_3$ and $X_4$, one of $X_5$, $X_6$, $X_7$ and $X_8$ and one of $X_9$, $X_{10}$, $X_{11}$ and $X_{12}$ are N;
   xi) one of $X_1$, $X_2$, $X_3$ and $X_4$ and two of $X_5$, $X_6$, $X_7$ and $X_8$ are N;

xii) two of $X_5$, $X_6$, $X_7$ and $X_8$ are N and one of $X_9$, $X_{10}$, $X_{11}$ and $X_{12}$ are N; or xiii) three of $X_1$, $X_5$, $X_7$ and $X_9$ are N.

7. A compound according to claim 1 wherein $R_1$ is selected from the group consisting of hydrogen, $C_{1-6}$alkyl, $C_{2-6}$alkenyl, $C(O)C_{1-6}$alkyl and $C(O)OC_{1-6}$alkyl.

8. A compound according to claim 1 wherein $R_2$ is selected from OH, SH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl)$_2$ and $OS(O)_n$ $C_{1-6}$alkyl.

9. A compound according to claim 1 wherein each $R_3$ is independently selected from the group consisting of hydrogen, halo, $C_{1-6}$alkyl, $C_{2-6}$alkenyl, $C_{1-6}$ haloalkyl, cycloalkyl, cycloalkenyl, aryl, heterocyclyl, heteroaryl, OH, SH, $CH_2OH$, $CH_2SH$, $OC_{1-6}$ alkyl, $SC_{1-6}$alkyl, $CH_2OC_{1-6}$alkyl, $CH_2SC_{1-6}$alkyl, $OC(O)C_{1-6}$alkyl, $CH_2OC(O)C_{1-6}$alkyl, $C(O)C_{1-6}$ alkyl, $CO_2H$, $CH_2CO_2H$, $CH_2C(O)C_{1-6}$alkyl, $C(O)OC_{1-6}$alkyl, $CH_2C(O)OC_{1-6}$alkyl, $CONH_2$, $CH_2CONH_2$, CN, $CH_2CN$, $NO_2$, $CH_2NO_2$, $NH_2$, $NH(C_{1-6}$ alkyl), $N(C_{1-6}$alkyl)$_2$, $CH_2NH_2$, $CH_2NH(C_{1-6}$ alkyl), $CH_2N(C_{1-6}$alkyl)$_2$, $SO_2H$, $CH_2S(O)_2H$, $SO_3H$, $CH_2SO_3H$, $S(O)_2C_{1-6}$alkyl, $CH_2S(O)_2C_{1-6}$alkyl, $S(O)_2OC_{1-6}$alkyl, $CH_2S(O)_2OC_{1-6}$alkyl, $S(O)_2NH_2$, $S(O)_nNH(C_{1-6}$alkyl), $S(O)_2N(C_{1-6}$alkyl)$_2$, $CH_2S(O)_2NH_2$, $CH_2S(O)_nNH(C_{1-6}$alkyl), $CH_2S(O)_2N(C_{1-6}$alkyl)$_2$, $NHC(O)NH_2$, $NHC(O)NH(C_{1-6}$ alkyl), $NHC(O)N(C_{1-6}$alkyl)$_2$ $CH_2NHC(O)NH_2$, $CH_2NHC(O)NH(C_{1-6}$alkyl) and $CH_2NHC(O)N(C_{1-6}$alkyl)$_2$.

10. The compound according to claim 1 which is a compound of formula (II):

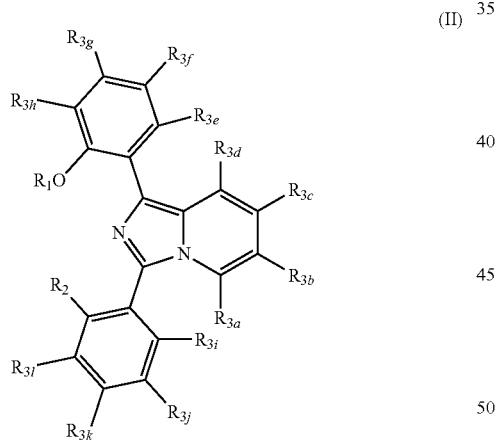

(II)

wherein $R_1$ and $R_2$ are as defined for formula (I) in claim 1 and $R_{3a}$, $R_{3b}$, $R_{3c}$, $R_{3d}$, $R_{3e}$, $R_{3f}$, $R_{3g}$, $R_{3h}$, $R_{3i}$, $R_{3j}$, $R_{3k}$ and $R_{3l}$ are each independently selected from the group consisting hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

11. The compound according to claim 1 which is a compound of formula (III):

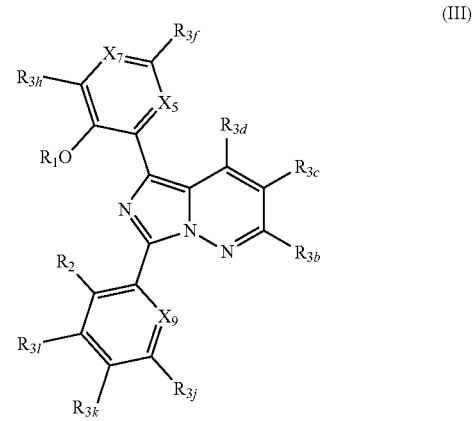

(III)

wherein $X_5$ is N or $CR_{3e}$; $X_7$ is N or $CR_{3g}$; $X_9$ is N or $CR_{3i}$; wherein none, one or two of $X_5$, $X_7$ and $X_9$ is N; $R_1$ and $R_2$ are as defined for formula (I) in claim 1 and $R_{3b}$, $R_{3c}$, $R_{3d}$, $R_{3e}$, $R_{3f}$, $R_{3g}$, $R_{3h}$, $R_{3i}$, $R_{3j}$, $R_{3k}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R)_2)_m$aryl, $(C(R_7)_2)_m$heterocyclyl, $(C(R_7)_2)_m$heteroaryl, $(C(R_7)_2)_m OR$, $(C(R)_2)_m SR$, $(C(R)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

12. The compound according to claim 1 which is a compound of formula (IV):

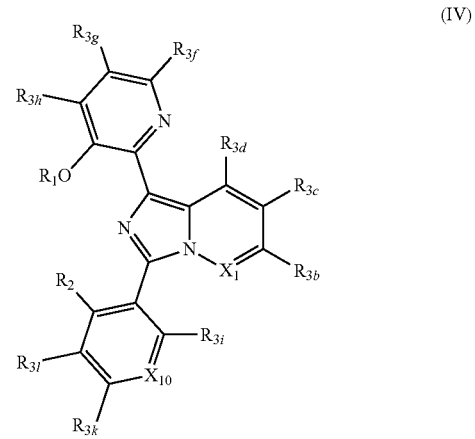

(IV)

wherein $X_1$ is N or $CR_{3a}$; $X_{10}$ is N or $CR_{3j}$;

$R_1$ and $R_2$ are as defined for formula (I) in claim 1 and $R_{3a}$, $R_{3b}$, $R_{3c}$, $R_{3d}$, $R_{3f}$, $R_{3h}$, $R_{3i}$, $R_{3j}$, $R_{3k}$ and $R_{3l}$ are each independently selected from the group consisting of hydrogen, halo, alkyl, alkenyl, alkynyl, haloalkyl, $(C(R)_2)_m$cycloalkyl, $(C(R)_2)_m$cycloalkenyl, $(C(R)_2)_m$aryl, $(C(R_7)_2)_m$heterocyclyl, $(C(R)_2)_m$heteroaryl, (C(R)$_2$)$_m$OR$_5$, (C(R)$_2$)$_m$SR$_5$, (C(R)$_2$)$_m$C(O)R$_4$, (C(R$_7$)$_2$)$_m$C(S)R$_4$, (C(R$_7$)$_2$)$_m$OC(O)R$_4$, (C(R$_7$)$_2$)$_m$SC(S)R$_4$, (C(R$_7$)$_2$)$_m$OC(S)R$_4$, (C(R$_7$)$_2$)$_m$SC(O)R$_4$, (C(R$_7$)$_2$)$_m$CN, (C(R$_7$)$_2$)$_m$NO$_2$, (C(R$_7$)$_2$)$_m$N(R$_6$)$_2$, (C(R$_7$)$_2$)$_m$S(O)$_n$R$_4$, (C(R$_7$)$_2$)$_m$N(R$_6$)C(O)N(R$_6$)$_2$ and (C(R$_7$)$_2$)$_m$N(R$_6$)C(S)N(R$_6$)$_2$, wherein R$_5$, R$_6$, R$_7$ and m are as defined for formula (I) in claim 1;

or a pharmaceutically acceptable salt or solvate thereof.

13. The compound according to claim 1 which is a compound of formula (V):

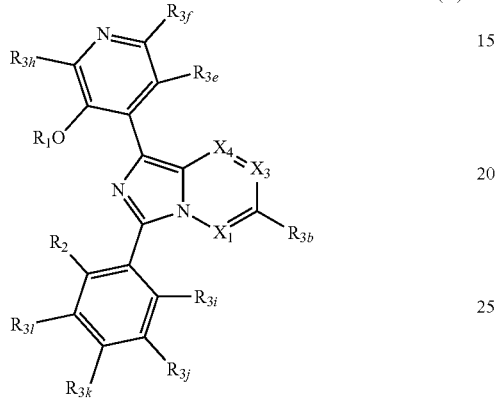

(V)

wherein X$_1$ is N or CR$_{3a}$; X$_3$ is N or CR$_{3c}$; X$_4$ is N or CR$_{3d}$; wherein none, one or two of X$_1$, X$_3$ and X$_4$ is N; R$_1$ and R$_2$ are as defined for formula (I) in claim 1 and R$_{3a}$, R$_{3b}$, R$_{3c}$, R$_{3d}$, R$_{3e}$, R$_{3f}$, R$_{3h}$, R$_{3i}$, R$_{3j}$, R$_{3k}$ and R$_{3l}$ are each independently selected from the group consisting of hydrogen, halo, alkyl, alkenyl, alkynyl, haloalkyl, (C(R$_7$)$_2$)$_m$cycloalkyl, (C(R$_7$)$_2$)$_m$cycloalkenyl, (C(R)$_2$)$_m$aryl, (C(R$_7$)$_2$)$_m$heterocyclyl, (C(R$_7$)$_2$)$_m$heteroaryl, (C(R$_7$)$_2$)$_m$OR, (C(R)$_2$)$_m$SR, (C(R$_7$)$_2$)$_m$C(O)R$_4$, (C(R$_7$)$_2$)$_m$C(S)R$_4$, (C(R$_7$)$_2$)$_m$OC(O)R$_4$, (C(R$_7$)$_2$)$_m$SC(S)R$_4$, (C(R$_7$)$_2$)$_m$OC(S)R$_4$, (C(R$_7$)$_2$)$_m$SC(O)R$_4$, (C(R$_7$)$_2$)$_m$CN, (C(R$_7$)$_2$)$_m$NO$_2$, (C(R$_7$)$_2$)$_m$N(R$_6$)$_2$, (C(R$_7$)$_2$)$_m$S(O)$_n$R$_4$, (C(R$_7$)$_2$)$_m$N(R$_6$)C(O)N(R$_6$)$_2$ and (C(R$_7$)$_2$)$_m$N(R$_6$)C(S)N(R$_6$)$_2$, wherein R$_4$, R$_5$, R$_6$, R$_7$ and m are as defined for formula (I) in claim 1;

or a pharmaceutically acceptable salt or solvate thereof.

14. The compound according to claim 1 which is a compound of formula (VI):

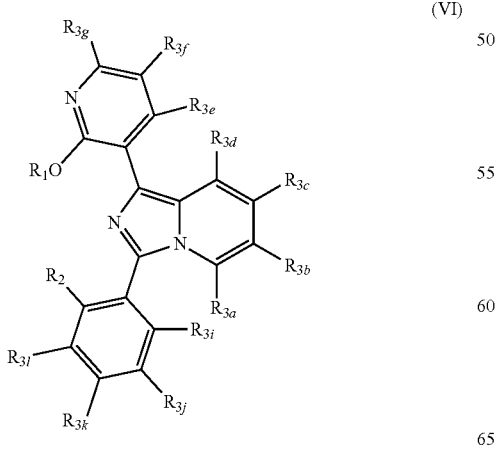

(VI)

wherein R$_1$ and R$_2$ are as defined for formula ( ) in claim 1 and R$_{3a}$, R$_{3b}$, R$_{3c}$, R$_{3d}$, R$_{3e}$, R$_{3f}$, R$_{3g}$, R$_{3h}$, R$_{3i}$, R$_{3j}$, R$_{3k}$ and R$_{3l}$ are each independently selected from the group consisting of hydrogen, halo, alkyl, alkenyl, alkynyl, haloalkyl, (C(R$_7$)$_2$)$_m$cycloalkyl, (C(R$_7$)$_2$)$_m$cycloalkenyl, (C(R$_7$)$_2$)$_m$aryl, (C(R$_7$)$_2$)$_m$heterocyclyl, (C(R)$_2$)$_m$heteroaryl, (C(R)$_2$)$_m$OR$_5$, (C(R)$_2$)$_m$SR$_5$, (C(R)$_2$)$_m$C(O)R$_4$, (C(R$_7$)$_2$)$_m$C(S)R$_4$, (C(R$_7$)$_2$)$_m$OC(O)R$_4$, (C(R$_7$)$_2$)$_m$SC(S)R$_4$, (C(R$_7$)$_2$)$_m$OC(S)R$_4$, (C(R$_7$)$_2$)$_m$SC(O)R$_4$, (C(R$_7$)$_2$)$_m$CN, (C(R$_7$)$_2$)$_m$NO$_2$, (C(R$_7$)$_2$)$_m$N(R$_6$)$_2$, (C(R$_7$)$_2$)$_m$S(O)$_n$R$_4$, (C(R$_7$)$_2$)$_m$N(R$_6$)C(O)N(R$_6$)$_2$ and (C(R$_7$)$_2$)$_m$N(R$_6$)C(S)N(R$_6$)$_2$, wherein R$_4$, R$_5$, R$_6$, R$_7$ and m are as defined for formula (I) in claim 1;

or a pharmaceutically acceptable salt or solvate thereof.

15. The compound according to claim 1 which is a compound of formula (VII):

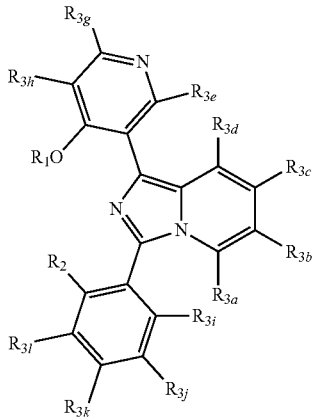

(VII)

wherein R$_1$ and R$_2$ are as defined for formula (I) in claim 1 and R$_{3a}$, R$_{3b}$, R$_{3c}$, R$_{3d}$, R$_{3e}$, R$_{3g}$, R$_{3h}$, R$_{3i}$, R$_{3j}$, R$_{3k}$ and R$_{3l}$ are each independently selected from the group consisting of hydrogen, halo, alkyl, alkenyl, alkynyl, haloalkyl, (C(R$_7$)$_2$)$_m$cycloalkyl, (C(R$_7$)$_2$)$_m$cycloalkenyl, (C(R$_7$)$_2$)$_m$aryl, (C(R$_7$)$_2$)$_m$heterocyclyl, (C(R$_7$)$_2$)$_m$heteroaryl, (C(R$_7$)$_2$)$_m$OR$_5$, (C(R$_7$)$_2$)$_m$SR$_5$, (C(R$_7$)$_2$)$_m$C(O)R$_4$, (C(R$_7$)$_2$)$_m$C(S)R$_4$, (C(R$_7$)$_2$)$_m$OC(O)R$_4$, (C(R$_7$)$_2$)$_m$SC(S)R$_4$, (C(R$_7$)$_2$)$_m$OC(S)R$_4$, (C(R$_7$)$_2$)$_m$SC(O)R$_4$, (C(R$_7$)$_2$)$_m$CN, (C(R$_7$)$_2$)$_m$NO$_2$, (C(R$_7$)$_2$)$_m$N(R$_6$)$_2$, (C(R$_7$)$_2$)$_m$S(O)$_n$R$_4$, (C(R$_7$)$_2$)$_m$N(R$_6$)C(O)N(R$_6$)$_2$ and (C(R)$_2$)$_m$N(R$_6$)C(S)N(R$_6$)$_2$, wherein R$_4$, R$_5$, R$_6$, R$_7$ and m are as defined for formula (I) in claim 1;

or a pharmaceutically acceptable salt or solvate thereof.

16. The compound according to claim 1 which is a compound of formula (VII):

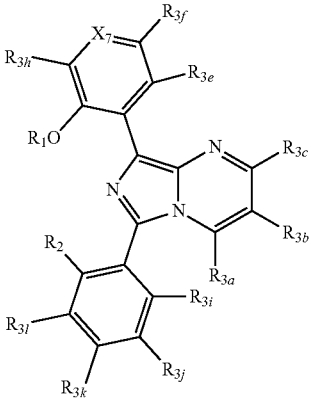

(VIII)

wherein $X_7$ is N or $CR_{3g}$, $R_1$ and $R_2$ are as defined for formula (I) in claim 1 and $R_{3a}$, $R_{3b}$, $R_{3c}$, $R_{3e}$, $R_{3f}$, $R_{3g}$, $R_{3h}$, $R_{3i}$, $R_{3j}$, $R_{3k}$ and $R_3$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

17. The compound according to claim 1 which is a compound of formula (IX):

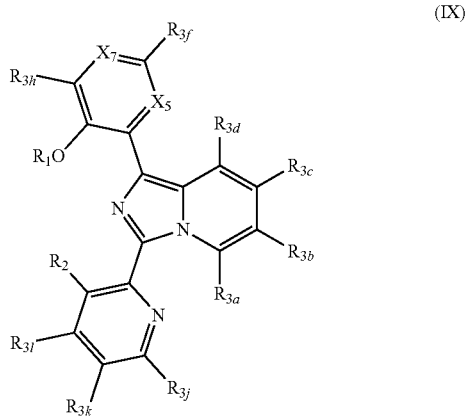

(IX)

Wherein $X_5$ is N or $CR_{3e}$; $X_7$ is N or $CR_{3g}$; $R_1$ and $R_2$ are as defined for formula (I) in claim 1 and $R_{3a}$, $R_{3b}$, $R_{3c}$, $R_{3d}$, $R_{3e}$, $R_{3f}$, $R_{3g}$, $R_{3h}$, $R_{3j}$, $R_{3k}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R)_2)_m CN$, $(C(R)_2)_m NO_2$, $(C(R_7)_2)_m N(R_6)_2$, $(C(R_7)_2)_m S(O)_n R_4$, $(C(R)_2)_m N(R_6)C(O)N(R_6)_2$ and $(C(R_7)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

18. The compound according to claim 1 which is a compound of formula (X):

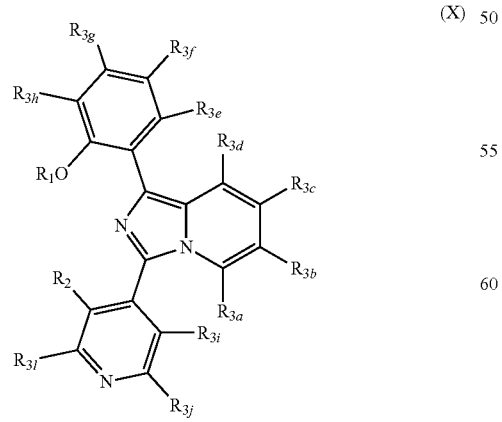

(X)

wherein $R_1$ and $R_2$ are as defined for formula (I) in claim 1 and $R_{3a}$, $R_{3b}$, $R_{3c}$, $R_{3d}$, $R_{3e}$, $R_{3f}$, $R_{3g}$, $R_{3h}$, $R_{3i}$, $R_{3j}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R)_2)_m OR_5$, $(C(R)_2)_m SR_5$, $(C(R)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R)_2)_m N(R_6)C(S)N(R_6)_2$, wherein $R_4$, $R_5$, $R_6$, $R_7$ and m are as defined for formula (I) in claim 1;

or a pharmaceutically acceptable salt or solvate thereof.

19. The compound according to claim 1 which is a compound of formula (XI):

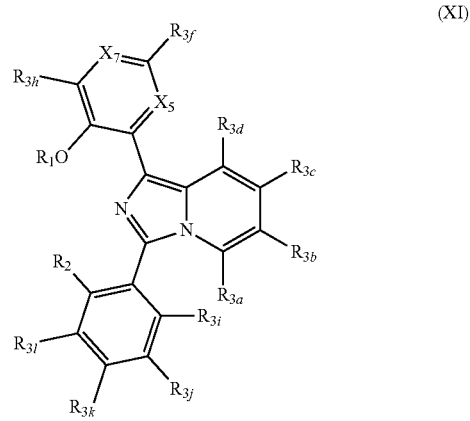

(XI)

wherein $X_5$ is N and $X_7$ is $CR_{3g}$; or $X_5$ is $CR_{3e}$ and $X_7$ is N; $R_1$ and $R_2$ are as defined for formula (I) in claim 1 and $R_{3a}$, $R_{3b}$, $R_{3c}$, $R_{3d}$, $R_{3e}$, $R_{3f}$, $R_{3g}$, $R_{3h}$, $R_{3i}$, $R_{3j}$, $R_{3k}$ and $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R)_2)_m$aryl, $(C(R)_2)_m$heterocyclyl, $(C(R_7)_2)_m$heteroaryl, $(C(R_7)_2)_m OR_5$, $(C(R)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R)_2)_m SC(O)R_4$, $(C(R)_2)_m CN$, $(C(R_7)_2)_m NO_2$, $(C(R_7)_2)_m N(R)_2$, $(C(R_7)_2)_m S(O)_n R_4$, $(C(R_7)_2)_m N(R)C(O)N(R_6)_2$ and $(C(R_7)_2)_m N(R)C(S)N(R_6)_2$, wherein $R_4$, $R_5$, $R_6$, $R_7$ and m are as defined for formula (I) in claim 1;

or a pharmaceutically acceptable salt or solvate thereof.

20. A compound according to claim 19 wherein $X_5$ is N.

21. A compound according to claim 19 wherein $X_7$ is N.

22. A pharmaceutical composition comprising a compound of formula (I) according to claim 1 or a pharmaceutically acceptable salt or solvate thereof and a pharmaceutically acceptable carrier and/or excipient.

* * * * *